(12) United States Patent
Baker et al.

(10) Patent No.: US 7,582,621 B2
(45) Date of Patent: Sep. 1, 2009

(54) BORON-CONTAINING SMALL MOLECULES

(75) Inventors: Stephen J. Baker, Mountain View, CA (US); Tsutomu Akama, Sunnyvale, CA (US); Carolyn Bellinger-Kawahara, Redwood City, CA (US); Vincent S. Hernandez, Watsonville, CA (US); Karin M. Hold, Belmont, CA (US); James J. Leyden, Malvern, PA (US); Kirk R. Maples, San Jose, CA (US); Jacob J. Plattner, Berkeley, CA (US); Virginia Sanders, San Francisco, CA (US); Yong-Kang Zhang, San Jose, CA (US)

(73) Assignee: Anacor Pharmaceuticals, Inc., Palo Alto, CA (US)

( * ) Notice: Subject to any disclaimer, the term of this patent is extended or adjusted under 35 U.S.C. 154(b) by 267 days.

(21) Appl. No.: 11/357,687

(22) Filed: Feb. 16, 2006

(65) Prior Publication Data
US 2006/0234981 A1    Oct. 19, 2006

Related U.S. Application Data

(60) Provisional application No. 60/654,060, filed on Feb. 16, 2005.

(51) Int. Cl.
*A61K 31/69* (2006.01)
*C07F 5/04* (2006.01)

(52) U.S. Cl. ........................................ 514/64; 558/288

(58) Field of Classification Search ................... 514/64; 558/288
See application file for complete search history.

(56) References Cited

U.S. PATENT DOCUMENTS 5,880,188 A * 3/1999 Austin et al. ................. 524/109
6,083,903 A * 7/2000 Adams et al. .................. 514/2

FOREIGN PATENT DOCUMENTS

WO    WO 2005/013892 A3    2/2005

OTHER PUBLICATIONS

Austin et al., 1996, CAS: 124:234024.*
fungicide: definition from Answre.com, 1998.*
Sudaxshina Murdan, "Drug Delivery to the Nail Following Topical Application," *International Journal of Pharmaceutics*, 236:1-26 (2002).
S. J. Baker, et al., "Progress on New Therapeutics for Fungal Nail Infections,"*Annual Reports in Medicinal Chemistry*, 40:323-335 (2005).

* cited by examiner

*Primary Examiner*—Rei-tsang Shiao
(74) *Attorney, Agent, or Firm*—Morgan, Lewis & Bockius, LLP

(57) ABSTRACT

This invention relates to compounds useful for treating fungal infections, more specifically topical treatment of onychomycosis and/or cutaneous fungal infections. This invention is directed to compounds that are active against fungi and have properties that allow the compound, when placed in contact with a patient, to reach the particular part of the skin, nail, hair, claw or hoof infected by the fungus. In particular the present compounds have physiochemical properties that facilitate penetration of the nail plate.

12 Claims, 12 Drawing Sheets

FIGURE 1A

| | MIC (ug/mL) | | | | | | | |
|---|---|---|---|---|---|---|---|---|
| | C. albicans ATCC 90028 | C. albicans F56 | C. neoformans F285 | A. fumigatus ATCC 13073 | T. mentagrophytes F311 | S. cerevisiae ANA309 | T. rubrum F296 | T. rubrum F296 w/ 5% keratin |
| C1 | 1 | 2 | 2 | 1 | 2 | 0.5 | 1 | 1 |
| C2 | 2 | 0.5 | 1 | 2 | 4 | | 8 | 8 |
| C3 | 16 | 32 | 32 | 16 | 16 | 4 | 32 | |
| C4 | 64 | 64 | > 64 | 32 | 32 | 8 | 32 | |
| C5 | 4 | 8 | 2 | 2 | 4 | 0.25 | 4 | |
| C6 | 8 | 16 | 8 | 16 | 16 | 64 | 16 | |
| C7 | > 64 | > 64 | > 64 | > 64 | 32 | 4 | 64 | |
| C8 | 2 | 2 | 8 | 2 | 4 | 2 | 8 | |
| C9 | > 64 | > 64 | > 64 | > 64 | 64 | >64 | 64 | |

FIGURE 1B

|  |  |  |  |  |  |  |  |  |
|---|---|---|---|---|---|---|---|---|
| C10 | 0.5 | 0.5 | 0.25 | 0.25 | ≤0.5 | <0.06 | 1 | 2 |
| C11 | 32 | 32 | 32 | 32 | 2 | 2 | 4 |  |
| C12 | 256 |  |  |  |  | >64 |  |  |
| C13 | 16 |  |  |  |  | 2 | 16 |  |
| C16 | 32 |  |  |  |  | 8 | 16 |  |
| C17 | 64 | 64 | 64 | 16 | 4 | 16 | 8 |  |
| C18 |  |  |  |  |  | 2 |  |  |
| C19 |  |  |  |  |  | 0.5 | 8 |  |
| C20 |  |  |  |  |  | 8 |  |  |
| C21 |  |  |  |  |  | 4 |  |  |
| C22 |  |  |  |  |  | >64 |  |  |
| C23 |  |  |  |  |  | >64 |  |  |

FIGURE 1C

| | | | | | | | | |
|---|---|---|---|---|---|---|---|---|
| C24 | | | | | | 16 | | |
| C25 | | | | | | >64 | | |
| C26 | | | | | | >64 | | |
| C27 | | | | | | >64 | | |
| C28 | | | | | | <0.06 | 4 | |
| C31 | | | | | | 8 | | |

EXAMPLE 2A

| Fungus | Broth used | MIC (µg/mL) | | | | |
|---|---|---|---|---|---|---|
| | | (C10) | Ciclopirox | Terbinafine | Fluconazole | Itraconazole |
| *A. fumigatus* ATCC 13073 | RPMI | 0.25 | nt | nt | >64 | 0.25 |
| *C. albicans* ATCC 90028 | RPMI | 1 | 0.5 | nt | 0.25 | ≤0.12 |
| *C. albicans* F56 | RPMI | 0.5 | nt | nt | >64 | 0.25 |
| *C. glabrata* ATCC 90030 | RPMI + MOPs | ≤0.5 | ≤0.5 | 64 | nt | ≤0.5 |
| *C. krusei* ATCC 44507 | RPMI + MOPs | 1 | ≤0.5 | 64 | nt | ≤0.5 |
| *C. neoformans* F285 | RPMI | 0.25 | nt | nt | 2 | ≤0.12 |
| *C. parapsilosis* ATCC 22019 | RPMI + MOPs | ≤0.5 | ≤0.5 | ≤0.5 | nt | ≤0.5 |
| *C. tropicalis* ATCC 13803 | RPMI + MOPs | ≤0.5 | ≤0.5 | 256 | nt | 1 |
| *E. floccosum* ATCC 52066 | RPMI + MOPs | ≤0.5 | ≤0.5 | ≤0.5 | nt | ≤0.5 |
| *F. solani* ATCC 36031 | RPMI + MOPs | ≤0.5 | 4 | 64 | nt | >256 |
| *M. furfur* ATCC 44344 | Urea | 1 | ≤0.5 | 2 | nt | ≤0.5 |
| *M. pachydermatis* ATCC 96746 | Urea | 1 | ≤0.5 | ≤0.5 | nt | ≤0.5 |
| *M. sympodialis* ATCC 44031 | Urea | 1 | ≤0.5 | ≤0.5 | nt | ≤0.5 |
| *M. audouinii* ATCC 42558 | RPMI + MOPs | 2 | 1 | ≤0.5 | nt | ≤0.5 |
| *M. canis* ATCC 10214 | RPMI + MOPs | 2 | ≤0.5 | ≤0.5 | nt | ≤0.5 |
| *M. gypseum* ATCC 24103 | RPMI + MOPs | 2 | ≤0.5 | ≤0.5 | nt | ≤0.5 |
| *T. mentagrophytes* F311 | RPMI + MOPs | 1 | 0.5 | ≤0.5 | 32 | ≤0.12 |
| *T. rubrum* F296 | RPMI + MOPs | 1 | 1 | ≤0.5 | 1 | ≤0.12 |
| *T. rubrum* F296 | RPMI + MOPS + 5% keratin powder | 2 | 1 | nt | 1 | nt |
| *T. tonsurans* ATCC 28942 | RPMI + MOPs | 2 | ≤0.5 | ≤0.5 | nt | ≤0.5 | nt = not tested

EXAMPLE 2B

| Fungus | Broth used* | MFC (μg/mL) | | | |
|---|---|---|---|---|---|
| | | (C10) | Ciclopirox | Terbinafine | Itraconazole |
| *T. mentagrophytes* F311 | RPMI + MOPs | 16 | 1 | ≤ 0.5 | 4 |
| *T. rubrum* F296 | RPMI + MOPs | 8 | 2 | ≤ 0.5 | 4 |

FIGURE 3

| Nail Samples | Radioactivity as mg Equivalent/g Nail Samples | | P value (t-test) |
|---|---|---|---|
| | Group A (C10) | Group C (Ciclopirox) | |
| Dorsal/intermediate center | 25.65 ± 8.80 | 7.40 ± 3.47 | 0.0008 |
| Ventral/intermediate center | 20.46 ± 4.72 | 3.09 ± 2.07 | 0.0001 |
| Remainder nail | 26.06 ± 12.41 | 4.38 ± 2.73 | 0.0022 |

* The data represents the mean ± S.D. of each group (n = 6).

FIGURE 4

| Sampling day | Radioactivity as mg Equivalent/Samples* | | P-value (t-test) |
| --- | --- | --- | --- |
| | Group A (C10) | Group C (Ciclopirox) | |
| Day 3 | 0.0609 ± 0.0605 | 0.0011 ± 0.0020 | 0.0043 |
| Day 6 | 0.1551 ± 0.1314 | 0.0013 ± 0.0027 | 0.0022 |
| Day 9 | 0.3892 ± 0.3714 | 0.0018 ± 0.0030 | 0.0022 |
| Day 12 | 0.6775 ± 0.6663 | 0.0014 ± 0.0019 | 0.0022 |
| Day 15 | 0.9578 ± 0.6106 | 0.0033 ± 0.0041 | 0.0022 |
| Total | 2.2405 ± 1.7325 | 0.0089 ± 0.0131 | 0.0022 |

* The data represents the mean ± S.D. of each group (n = 6).

BORON-CONTAINING SMALL MOLECULES

CROSS-REFERENCE TO RELATED APPLICATIONS

The present application is related to U.S. Provisional Patent Application 60/654,060 filed Feb. 16, 2005, which is incorporated by reference in its entirety for all purposes.

BACKGROUND FOR THE INVENTION

Infections of the nail and hoof, known as ungual and/or periungual infections, pose serious problems in dermatology. These ungual and/or periungual can be caused by sources such as fungi, viruses, yeast, bacteria and parasites. Onychomycosis is an example of these serious ungual and/or periungual infections and is caused by at least one fungus. Current treatment for ungual and/or periungual infections generally falls into three categories: systemic administration of medicine; surgical removal of all or part of the nail or hoof followed by topical treatment of the exposed tissue; or topical application of conventional creams, lotions, gels or solutions, frequently including the use of bandages to keep these dosage forms in place on the nail or hoof. All of these approaches have major drawbacks. The following discussion is particularly directed to drawbacks associated with current treatment of ungual and/or periungual antifungal infections.

Long term systemic (oral) administration of an antifungal agent for the treatment of onychomycosis is often required to produce a therapeutic effect in the nail bed. For example, oral treatment with the antifungal compound ketoconozole typically requires administration of 200 to 400 mg/day for 6 months before any significant therapeutic benefit is realized. Such long term, high dose systemic therapy can have significant adverse effects. For example, ketoconozole has been reported to have liver toxicity effects and reduces testosterone levels in blood due to adverse effects on the testes. Patient compliance is a problem with such long term therapies especially those which involve serious adverse effects. Moreover, this type of long term oral therapy is inconvenient in the treatment of a horse or other ruminants afflicted with fungal infections of the hoof. Accordingly, the risks associated with parenteral treatments generate significant disincentive against their use and considerable patient non-compliance.

Surgical removal of all or part of the nail followed by topical treatment also has severe drawbacks. The pain and discomfort associated with the surgery and the undesirable cosmetic appearance of the nail or nail bed represent significant problems, particularly for female patients or those more sensitive to physical appearance. Generally, this type of treatment is not realistic for ruminants such as horses.

Topical therapy has significant problems too. Topical dosage forms such as creams, lotions, gels etc., can not keep the drug in intimate contact with the infected area for therapeutically effective periods of time. Bandages have been used to hold drug reservoirs in place in an attempt to enhance absorption of the pharmaceutical agent. However the bandages are thick, awkward, troublesome and generally lead to poor patient compliance.

Hydrophilic and hydrophobic film forming topical antifungal solutions have also been developed. These dosage forms provide improved contact between the drug and the nail, but the films are not occlusive. Topical formulations for fungal infection treatment have largely tried to deliver the drug to the target site (an infected nail bed) by diffusion across or through the nail.

Nail is more like hair than stratum corneum with respect to chemical composition and permeability. Nitrogen is the major component of the nail attesting to the nail's proteinaceous nature. The total lipid content of mature nail is 0.1-1.0%, while the stratum corneum lipid is about 10% w/w. The nail is 100-200 times thicker than the stratum corneum and has a very high affinity and capacity for binding and retaining antifungal drugs. Consequently little if any drug penetrates through the nail to reach the target site. Because of these reasons topical therapy for fungal infections have generally been ineffective.

Compounds known as penetration or permeation enhancers are well known in the art to produce an increase in the permeability of skin or other body membranes to a pharmacologically active agent. The increased permeability allows an increase in the rate at which the drug permeates through the skin and enters the blood stream. Penetration enhancers have been successful in overcoming the impermeability of pharmaceutical agents through the skin. However, the thin stratum corneum layer of the skin, which is about 10 to 15 cells thick and is formed naturally by cells migrating toward the skin surface from the basal layer, has been easier to penetrate than nails. Moreover, known penetration enhancers have not proven to be useful in facilitating drug migration through the nail tissue.

Antimicrobial compositions for controlling bacterial and fungal infections comprising a metal chelate of 8-hydroxyquinoline and an alkyl benzene sulfonic acid have been shown to be efficacious due to the increased ability of the oleophilic group to penetrate the lipoid layers of micro-cells. The compounds however, do not effectively increase the ability to carry the pharmaceutically active antifungal through the cornified layer or stratum corneum of the skin. U.S. Pat. No. 4,602,011, West et al., Jul. 22, 1986; U.S. Pat. No. 4,766,113, West et al., Aug. 23, 1988.

Therefore, there is a need in the art for compounds which can effectively penetrate the nail. There is also need in the art for compounds which can effectively treat ungual and/or periungual infections. These and other needs are addressed by the current invention.

SUMMARY OF THE INVENTION

In a first aspect, the invention provides a compound having a structure according to Formula I:

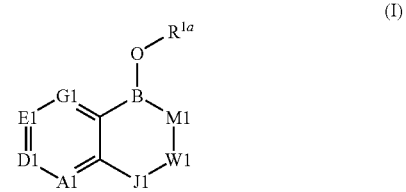

wherein B is boron. $R^{1a}$ is a member selected from a negative charge, a salt counterion, H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. M1 is a member selected from oxygen, sulfur and $NR^{2a}$. $R^{2a}$ is a member selected from H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. J1 is a member selected from $(CR^{3a}R^{4a})_{n1}$ and $CR^{5a}$. $R^{3a}$, $R^{4a}$, and $R^{5a}$ are members independently selected from H, OH, $NH_2$, SH, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. The index n1 is an integer selected from 0 to 2. W1 is a member selected from C=O (carbonyl), $(CR^{6a}R^{7a})_{m1}$ and $CR^{8a}$. $R^{6a}$, $R^{7a}$, and $R^{8a}$ are members independently selected from H, OH, $NH_2$, SH, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. The index m1 is an integer selected from 0 and 1. A1 is a member selected from $CR^{9a}$ and N. D1 is a member selected from $CR^{10a}$ and N. E1 is a member selected from $CR^{11a}$ and N. G1 is a member selected from $CR^{12a}$ and N. $R^{9a}$, $R^{10a}$, $R^{11a}$ and $R^{12a}$ are members independently selected from H, OH, $NH_2$, SH, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. The combination of nitrogens (A1+D1+E1+G1) is an integer selected from 0 to 3. A member selected from $R^{3a}$, $R^{4a}$ and $R^{5a}$ and a member selected from $R^{6a}$, $R^{7a}$ and $R^{8a}$, together with the atoms to which they are attached, are optionally joined to form a 4 to 7 membered ring. $R^{3a}$ and $R^{4a}$, together with the atoms to which they are attached, are optionally joined to form a 4 to 7 membered ring. $R^{6a}$ and $R^{7a}$, together with the atoms to which they are attached, are optionally joined to form a 4 to 7 membered ring. $R^{9a}$ and $R^{10a}$, together with the atoms to which they are attached, are optionally joined to form a 4 to 7 membered ring. $R^{10a}$ and $R^{11a}$, together with the atoms to which they are attached, are optionally joined to form a 4 to 7 membered ring. $R^{11a}$ and $R^{12a}$, together with the atoms to which they are attached, are optionally joined to form a 4 to 7 membered ring. The aspect has the proviso that when M1 is oxygen, W1 is a member selected from $(CR^{3a}R^{4a})_{n1}$, wherein n1 is 0, J1 is a member selected from $(CR^{6a}R^{7a})_{m1}$, wherein m1 is 1, A1 is $CR^{9a}$, D1 is $CR^{10a}$, E1 is $CR^{11a}$, G1 is $CR^{12a}$, then $R^{9a}$ is not halogen, methyl, ethyl, or optionally joined with $R^{10a}$ to a form phenyl ring; $R^{10a}$ is not unsubstituted phenoxy, $C(CH_3)_3$, halogen, $CF_3$, methoxy, ethoxy, or optionally joined with $R^{9a}$ to form a phenyl ring; $R^{11a}$ is not halogen or optionally joined with $R^{10a}$ to form a phenyl ring; and $R^{12a}$ is not halogen. The aspect has the further proviso that when M1 is oxygen, W1 is a member selected from $(CR^{3a}R^{4a})_{n1}$, wherein n1 is 0, J1 is a member selected from $(CR^{6a}R^{7a})_{m1}$, wherein m1 is 1, A1 is $CR^{9a}$, D1 is $CR^{10a}$, E1 is $CR^{11a}$, G1 is $CR^{12a}$, then neither $R^{6a}$ nor $R^{7a}$ are halophenyl. The aspect has the further proviso that when M1 is oxygen, W1 is a member selected from $(CR^{3a}R^{4a})_{n1}$, wherein n1 is 0, J1 is a member selected from $(CR^{6a}R^{7a})_{m1}$, wherein m1 is 1, A1 is $CR^{9a}$, D1 is $CR^{10a}$, E1 is $CR^{11a}$, G is $CR^{12a}$, and $R^{9a}$, $R^{10a}$ and $R^{11a}$ are H, then $R^{6a}$, $R^{7a}$ and $R^{12a}$ are not H. The aspect has the further proviso that when M1 is oxygen wherein n1 is 1, J1 is a member selected from $(CR^{6a}R^{7a})_{m1}$, wherein m1 is 0, A1 is $CR^{9a}$, D1 is $CR^{1a}$, E1 is $CR^{11a}$, G1 is $CR^{12a}$, $R^{9a}$ is H, $R^{10a}$ is H, $R^{11a}$ is H, $R^{6a}$ is H, $R^{7a}$ is H, $R^{12a}$ is H, then W1 is not C=O (carbonyl). The aspect has the further proviso that when M1 is oxygen, W1 is $CR^{5a}$, J1 is $CR^{8a}$, A1 is $CR^{9a}$, D1 is $CR^{10a}$, E1 is $CR^{11a}$, G1 is $CR^{2a}$, $R^{6a}$, $R^{7a}$, $R^{9a}$, $R^{10a}$, $R^{11a}$ and $R^{12a}$ are H, then $R^{5a}$ and $R^{8a}$, together with the atoms to which they are attached, do not form a phenyl ring.

In a second aspect, the invention provides a pharmaceutical formulation comprising (a) a pharmaceutically acceptable excipient; and (b) a compound having a structure according to Formula II:

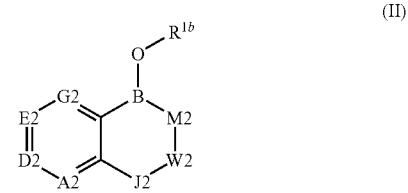

(II)

wherein B is boron. $R^{1b}$ is a member selected from a negative charge, a salt counterion, H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. M2 is a member selected from oxygen, sulfur and $NR^{2b}$. $R^{2b}$ is a member selected from H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. J2 is a member selected from $(CR^{3b}R^{4b})_{n2}$ and $CR^{5b}$. $R^{3b}$, $R^{4b}$, and $R^{5b}$ are members independently selected from H, OH, $NH_2$, SH, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. The index n2 is an integer selected from 0 to 2. W2 is a member selected from C=O (carbonyl), $(CR^{6b}R^{7b})_{m2}$ and $CR^{8b}$. $R^{6b}$, $R^{7b}$, and $R^{8b}$ are members independently selected from H, OH, $NH_2$, SH, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. The index m2 is an integer selected from 0 and 1. A2 is a member selected from $CR^{9b}$ and N. D2 is a member selected from $CR^{10b}$ and N. E2 is a member selected from $CR^{11b}$ and N. G2 is a member selected from $CR^{12b}$ and N. $R^{9b}$, $R^{10b}$, $R^{11b}$ and $R^{12b}$ are members independently selected from H, OH, $NH_2$, SH, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. The combination of nitrogens (A2+D2+E2+G2) is an integer selected from 0 to 3. A member selected from $R^{3b}$, $R^{4b}$ and $R^{5b}$ and a member selected from $R^{6b}$, $R^{7b}$ and $R^{8b}$, together with the atoms to which they are attached, are optionally joined to form a 4 to 7 membered ring. $R^{3b}$ and $R^{4b}$, together with the atoms to which they are attached, are optionally joined to form a 4 to 7 membered ring. $R^{6b}$ and $R^{7b}$, together with the atoms to which they are attached, are optionally joined to form a 4 to 7 membered ring. $R^{9b}$ and $R^{10b}$, together with the atoms to which they are attached, are optionally joined to form a 4 to 7 membered ring. $R^{10b}$ and $R^{11b}$, together with the atoms to which they are attached, are optionally joined to form a 4 to 7 membered ring. $R^{11b}$ and $R^{12b}$, together with the atoms to which they are attached, are optionally joined to form a 4 to 7 membered ring.

In another aspect, the invention provides a method of killing a microorganism, comprising contacting the microorganism with a therapeutically effective amount of a compound of the invention.

In another aspect, the invention provides a method of inhibiting microorganism growth, comprising contacting the microorganism with a therapeutically effective amount of a compound of the invention.

In another aspect, the invention provides a method of treating an infection in an animal, comprising administering to the animal a therapeutically effective amount of a compound of the invention.

In another aspect, the invention provides a method of preventing an infection in an animal, comprising administering to the animal a therapeutically effective amount of a compound of the invention.

In another aspect, the invention provides a method of treating a systemic infection or an ungual or periungual infection in a human, comprising administering to the animal a therapeutically effective amount of a compound of the invention.

In another aspect, the invention provides a method of treating onychomycosis in a human, comprising administering to the animal a therapeutically effective amount of a compound of the invention.

In another aspect, the invention provides a method of synthesizing a compound of the invention.

In another aspect, the invention provides a method of delivering a compound from the dorsal layer of the nail plate to the nail bed. The method comprises contacting said cell with a compound capable of penetrating the nail plate, under conditions sufficient to penetrate said nail plate, and thereby delivering the compound. The compound has a molecular weight of between about 100 and about 200 Da. The compound also has a log P value of between about 1.0 and about 2.6. The compound has a water solubility between about 0.1 mg/mL and 1.0 g/mL octanol/saturated water.

BRIEF DESCRIPTION OF THE DRAWINGS

Figure 1C:
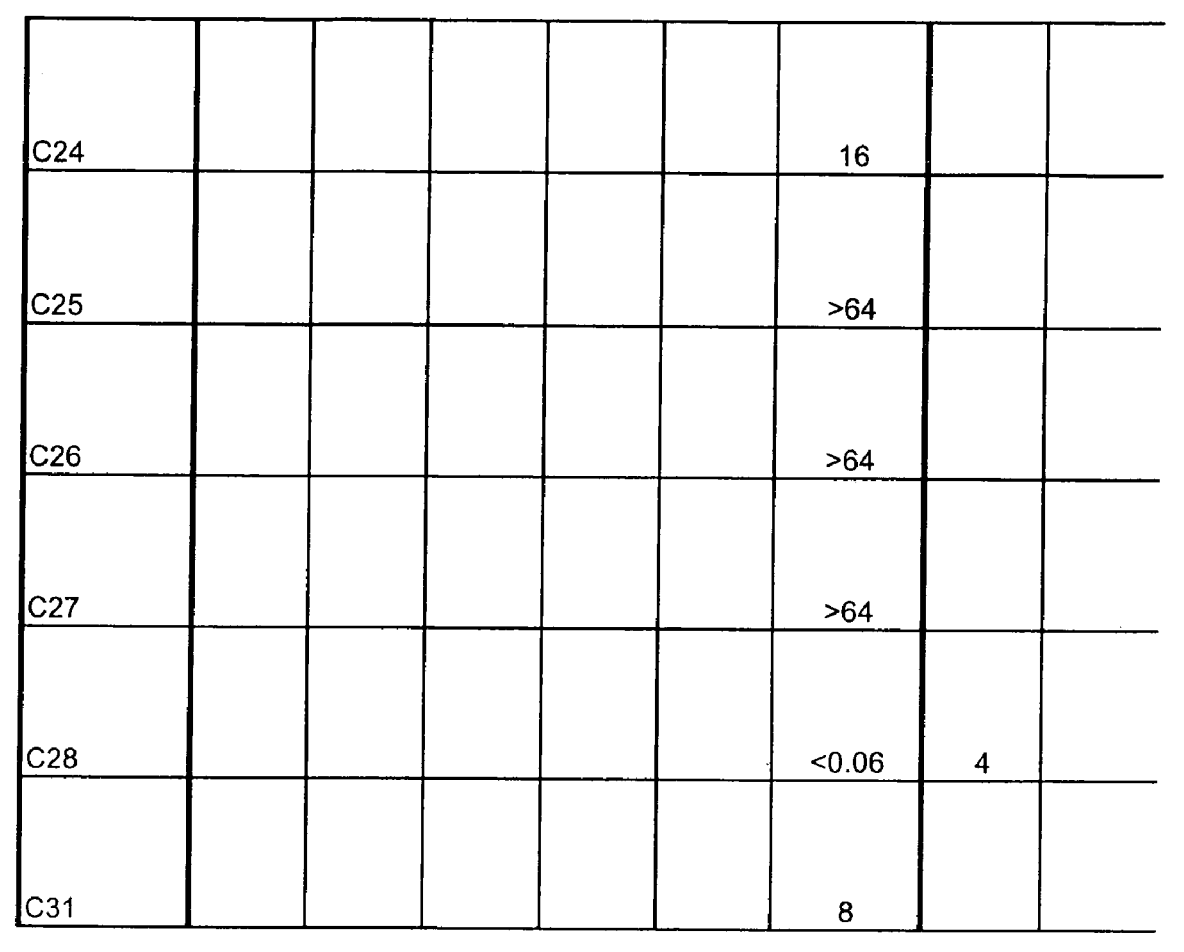

FIG. 1 is a table of minimum inhibitory concentration (MIC) data of CBO against various fungi.

FIG. 2A displays minimum inhibitory concentration (MIC) for C10, ciclopirox, terbinafine, fluconazole and itraconazole (comparator drugs) against 19 test strains of fungi.

FIG. 2B displays minimum fungicidal concentration (MFC) for C10, ciclopirox, terbinafine and itraconazole (comparator drugs) against 2 test strains of fungi.

FIG. 3 displays a comparison of Normalized C10 and Ciclopirox Equivalent in Each Part of Nail Plate Samples after 14-day Treatment.

FIG. 4 displays a comparison of C10 and Ciclopirox Equivalent in Cotton Ball Supporting Bed Samples after 14-day Treatment.

DETAILED DESCRIPTION OF THE INVENTION

I. Definitions and Abbreviations

Figure 5:
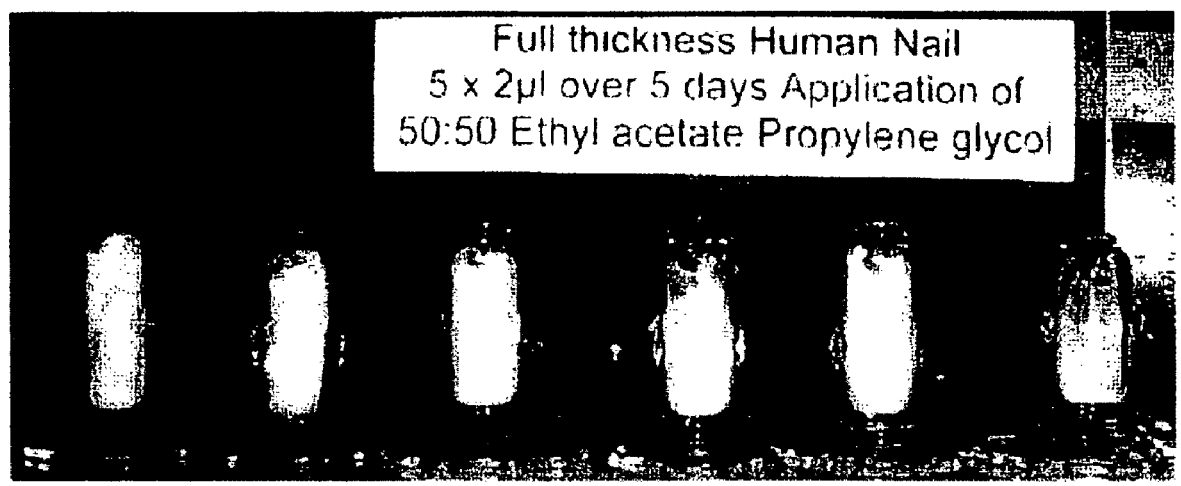
FIG. 5 displays the results of a placebo for C10 (50:50 propylene glycol and ethyl acetate) applied per day over five days. Full carpet growth of the organism T. rubrum was observed.

The abbreviations used herein generally have their conventional meaning within the chemical and biological arts.

"Compound of the invention," as used herein refers to the compounds discussed herein, pharmaceutically acceptable salts and prodrugs of these compounds.

MIC, or minimum inhibitory concentration, is the point where compound stops more than 90% of cell growth relative to an untreated control.

Where substituent groups are specified by their conventional chemical formulae, written from left to right, they equally encompass the chemically identical substituents, which would result from writing the structure from right to left, e.g., —CH$_2$O— is intended to also recite —OCH$_2$—.

The term "poly" as used herein means at least 2. For example, a polyvalent metal ion is a metal ion having a valency of at least 2.

"Moiety" refers to the radical of a molecule that is attached to another moiety.

The symbol , whether utilized as a bond or displayed perpendicular to a bond, indicates the point at which the displayed moiety is attached to the remainder of the molecule.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl." Alkyl groups that are limited to hydrocarbon groups are termed "homoalkyl".

The term "alkylene" by itself or as part of another substituent means a divalent radical derived from an alkane, as exemplified, but not limited, by —CH$_2$CH$_2$CH$_2$CH$_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom. In an exemplary embodiment, the heteroatoms can be selected from the group consisting of B, O, N and S, and wherein the nitrogen and sulfur atoms may optionally be oxidized and the nitrogen heteroatom may optionally be quaternized. The heteroatom(s) B, O, N and S may be placed at any interior position of the heteroalkyl group or at the position at which the alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —$CH_2$—CH=N—$OCH_3$, and —CH=CH—N($CH_3$)—$CH_3$. Up to two heteroatoms may be consecutive, such as, for example, —$CH_2$—NH—$OCH_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, substituent that can be a single ring or multiple rings (preferably from 1 to 3 rings), which are fused together or linked covalently. The term "heteroaryl" refers to aryl groups (or rings) that contain from one to four heteroatoms. In an exemplary embodiment, the heteroatom is selected from B, N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: —OR', =O, =NR', =N—OR', —NR'R", —SR', —halogen, —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R'" and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —C(O)$CH_3$, —C(O)$CF_3$, —C(O)$CH_2OCH_3$, and the like).

Similar to the substituents described for the alkyl radical, substituents for the aryl and heteroaryl groups are generically referred to as "aryl group substituents." The substituents are selected from, for example: halogen, —OR', =O, =NR', =N—OR', —NR'R", —SR', -halogen, —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R", —S(O)$_2$NR'R", —NRSO$_2$R', —CN and —NO$_2$, —R', —N$_3$, —CH(Ph)$_2$, fluoro($C_1$-$C_4$)alkoxy, and fluoro($C_1$-

$C_4$)alkyl, in a number ranging from zero to the total number of open valences on the aromatic ring system; and where R', R", R''' and R'''' are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R", R''' and R'''' groups when more than one of these groups is present.

Two of the substituents on adjacent atoms of the aryl or heteroaryl ring may optionally be replaced with a substituent of the formula —T—C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula —A—(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R''')$_d$—, where s and d are independently integers of from 0 to 3, and X is —O—, —NR'—, —S—, —S(O)—, —S(O)$_2$—, or —S(O)$_2$NR'—. The substituents R, R', R" and R''' are preferably independently selected from hydrogen or substituted or unsubstituted ($C_1$-$C_6$)alkyl.

"Ring" as used herein means a substituted or unsubstituted cycloalkyl, substituted or unsubstituted heterocycloalkyl, substituted or unsubstituted aryl, or substituted or unsubstituted heteroaryl. A ring includes fused ring moieties. The number of atoms in a ring is typically defined by the number of members in the ring. For example, a "5- to 7-membered ring" means there are 5 to 7 atoms in the encircling arrangement. The ring optionally included a heteroatom. Thus, the term "5- to 7-membered ring" includes, for example pyridinyl and piperidinyl. The term "ring" further includes a ring system comprising more than one "ring", wherein each "ring" is independently defined as above.

As used herein, the term "heteroatom" includes atoms other than carbon (C) and hydrogen (H). Examples include oxygen (O), nitrogen (N) sulfur (S), silicon (Si), germanium (Ge), aluminum (Al) and boron (B).

The symbol "R" is a general abbreviation that represents a substituent group that is selected from substituted or unsubstituted alkyl, substituted or unsubstituted heteroalkyl, substituted or unsubstituted aryl, substituted or unsubstituted heteroaryl, substituted or unsubstituted cycloalkyl and substituted or unsubstituted heterocycloalkyl groups.

By "effective" amount of a drug, formulation, or permeant is meant a sufficient amount of a active agent to provide the desired local or systemic effect. A "Topically effective," "Cosmetically effective," "pharmaceutically effective," or "therapeutically effective" amount refers to the amount of drug needed to effect the desired therapeutic result.

"Topically effective" refers to a material that, when applied to the skin, nail, hair, claw or hoof produces a desired pharmacological result either locally at the place of application or systemically as a result of transdermal passage of an active ingredient in the material.

"Cosmetically effective" refers to a material that, when applied to the skin, nail, hair, claw or hoof, produces a desired cosmetic result locally at the place of application of an active ingredient in the material.

The term "pharmaceutically acceptable salts" is meant to include salts of the compounds of the invention which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", Journal of Pharmaceutical Science 66: 1-19 (1977)). Certain specific compounds of the present invention contain both basic and acidic functionalities that allow the compounds to be converted into either base or acid addition salts.

The neutral forms of the compounds are preferably regenerated by contacting the salt with a base or acid and isolating the parent compounds in the conventional manner. The parent form of the compound differs from the various salt forms in certain physical properties, such as solubility in polar solvents.

In addition to salt forms, the present invention provides compounds which are in a prodrug form. Prodrugs of the compounds or complexes described herein readily undergo chemical changes under physiological conditions to provide the compounds of the present invention. Additionally, prodrugs can be converted to the compounds of the present invention by chemical or biochemical methods in an ex vivo environment.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are encompassed within the scope of the present invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

The term "pharmaceutically acceptable carrier" or "pharmaceutically acceptable vehicle" refers to any formulation or carrier medium that provides the appropriate delivery of an effective amount of a active agent as defined herein, does not interfere with the effectiveness of the biological activity of the active agent, and that is sufficiently non-toxic to the host or patient. Representative carriers include water, oils, both vegetable and mineral, cream bases, lotion bases, ointment bases and the like. These bases include suspending agents, thickeners, penetration enhancers, and the like. Their formulation is well known to those in the art of cosmetics and topical pharmaceuticals. Additional information concerning carriers can be found in *Remington: The Science and Practice of Pharmacy,* 21st Ed., Lippincott, Williams & Wilkins (2005) which is incorporated herein by reference.

"Pharmaceutically acceptable topical carrier" and equivalent terms refer to pharmaceutically acceptable carriers, as described herein above, suitable for topical application. An inactive liquid or cream vehicle capable of suspending or dissolving the active agent(s), and having the properties of being nontoxic and non-inflammatory when applied to the skin, nail, hair, claw or hoof is an example of a pharmaceutically-acceptable topical carrier. This term is specifically intended to encompass carrier materials approved for use in topical cosmetics as well.

The term "pharmaceutically acceptable additive" refers to preservatives, antioxidants, fragrances, emulsifiers, dyes and excipients known or used in the field of drug formulation and that do not unduly interfere with the effectiveness of the biological activity of the active agent, and that is sufficiently non-toxic to the host or patient. Additives for topical formulations are well-known in the art, and may be added to the topical composition, as long as they are pharmaceutically acceptable and not deleterious to the epithelial cells or their function. Further, they should not cause deterioration in the stability of the composition. For example, inert fillers, anti-irritants, tackifiers, excipients, fragrances, opacifiers, antioxidants, gelling agents, stabilizers, surfactant, emollients, coloring agents, preservatives, buffering agents, other permeation enhancers, and other conventional components of topical or transdermal delivery formulations as are known in the art.

The terms "enhancement," "penetration enhancement" or "permeation enhancement" relate to an increase in the permeability of the skin, nail, hair, claw or hoof to a drug, so as to increase the rate at which the drug permeates through the skin, nail, hair, claw or hoof. The enhanced permeation effected through the use of such enhancers can be observed, for example, by measuring the rate of diffusion of the drug through animal or human skin, nail, hair, claw or hoof using a diffusion cell apparatus. A diffusion cell is described by Merritt et al. Diffusion Apparatus for Skin Penetration, *J of Controlled Release,* 1 (1984) pp. 161-162. The term "permeation enhancer" or "penetration enhancer" intends an agent or a mixture of agents, which, alone or in combination, act to increase the permeability of the skin, nail, hair or hoof to a drug.

The term "excipients" is conventionally known to mean carriers, diluents and/or vehicles used in formulating drug compositions effective for the desired use.

The term "topical administration" refers to the application of a pharmaceutical agent to the external surface of the skin, nail, hair, claw or hoof, such that the agent crosses the external surface of the skin, nail, hair, claw or hoof and enters the underlying tissues. Topical administration includes application of the composition to intact skin, nail, hair, claw or hoof, or to an broken, raw or open wound of skin, nail, hair, claw or hoof. Topical administration of a pharmaceutical agent can result in a limited distribution of the agent to the skin and surrounding tissues or, when the agent is removed from the treatment area by the bloodstream, can result in systemic distribution of the agent.

The term "transdermal delivery" refers to the diffusion of an agent across the barrier of the skin, nail, hair, claw or hoof resulting from topical administration or other application of a composition. The stratum corneum acts as a barrier and few pharmaceutical agents are able to penetrate intact skin. In contrast, the epidermis and dermis are permeable to many solutes and absorption of drugs therefore occurs more readily through skin, nail, hair, claw or hoof that is abraded or otherwise stripped of the stratum corneum to expose the epidermis. Transdermal delivery includes injection or other delivery through any portion of the skin, nail, hair, claw or hoof or mucous membrane and absorption or permeation through the remaining portion. Absorption through intact skin, nail, hair, claw or hoof can be enhanced by placing the active agent in an appropriate pharmaceutically acceptable vehicle before application to the skin, nail, hair, claw or hoof. Passive topical administration may consist of applying the active agent directly to the treatment site in combination with emollients or penetration enhancers. As used herein, transdermal delivery is intended to include delivery by permeation through or past the integument, i.e. skin, nail, hair, claw or hoof.

II. Introduction

The present invention provides novel boron compounds and methods for the preparation of these molecules. The invention further provides boron compounds as analogs comprising a functional moiety, such as a drug moiety and methods of use for said analogs.

III. The Compounds

In a first aspect, the invention provides a compound having a structure according to Formula I:

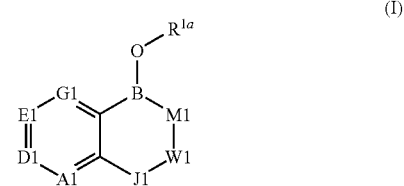

(I)

wherein B is boron. $R^{1a}$ is a member selected from a negative charge, a salt counterion, H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. M1 is a member selected from oxygen, sulfur and $NR^{2a}$. $R^{2a}$ is a member selected from H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. J1 is a member selected from $(CR^{3a}R^{4a})_{n1}$ and $CR^{5a}$. $R^{3a}$, $R^{4a}$, and $R^{5a}$ are members independently selected from H, OH, $NH_2$, SH, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. The index n1 is an integer selected from 0 to 2. W1 is a member selected from C=O (carbonyl), $(CR^{6a}R^{7a})_{m1}$ and $CR^{8a}$. $R^{6a}$, $R^{7a}$, and $R^{8a}$ are members independently selected from H, OH, $NH_2$, SH, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. The index m1 is an integer selected from 0 and 1. A1 is a member selected from $CR^{9a}$ and N. D1 is a member selected from $CR^{10a}$ and N. E1 is a member selected from $CR^{11a}$ and N. G1 is a member selected from $CR^{12a}$ and N. $R^{9a}$, $R^{10a}$, $R^{11a}$ and $R^{12a}$ are members independently selected from H, OH, $NH_2$, SH, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. The combination of nitrogens (A1+D1+E1+G1) is an integer selected from 0 to 3. A member selected from $R^{3a}$, $R^{4a}$ and $R^{5a}$ and a member selected from $R^{6a}$, $R^{7a}$ and $R^{8a}$, together with the atoms to which they are attached, are optionally joined to form a 4 to 7 membered ring. $R^{3a}$ and $R^{4a}$, together with the atoms to which they are attached, are optionally joined to form a 4 to 7 membered ring. $R^{6a}$ and $R^{7a}$, together with the atoms to which they are attached, are optionally joined to form a 4 to 7 membered ring. $R^{9a}$ and $R^{10a}$, together with the atoms to which they are attached, are optionally joined to form a 4 to 7 membered ring. $R^{10a}$ and $R^{11a}$, together with the atoms to which they are attached, are optionally joined to form a 4 to 7 membered ring. $R^{11a}$ and $R^{12a}$, together with the atoms to which they are attached, are optionally joined to form a 4 to 7 membered ring. The aspect has the proviso that when M1 is oxygen, W1 is a member selected from $(CR^{3a}R^{4a})_{n1}$, wherein n1 is 0, J1 is a member selected from $(CR^{6a}R^{7a})_{m1}$, wherein m1 is 1, A1 is $CR^{9a}$, D1 is $CR^{10a}$, E1 is $CR^{1a}$, G1 is $CR^{12a}$, then $R^{9a}$ is not halogen, methyl, ethyl, or optionally joined with $R^{10a}$ to a form phenyl ring; $R^{10a}$ is not unsubstituted phenoxy, $C(CH_3)_3$, halogen, $CF_3$, methoxy, ethoxy, or optionally joined with $R^{9a}$ to form a phenyl ring; $R^{11a}$ is not halogen or optionally joined with $R^{10a}$ to form a phenyl ring; and $R^{12a}$ is not halogen. The aspect has the further proviso that when M1 is oxygen, W1 is a member selected from $(CR^{3a}R^{4a})_{n1}$, wherein n1 is 0, J1 is a member selected from $(CR^{6a}R^{7a})_{m1}$, wherein m1 is 1, A1 is $CR^{9a}$, D1 is $CR^{10a}$, E1 is $CR^{11a}$, G1 is $CR^{12a}$, then neither $R^{6a}$ nor $R^{7a}$ are halophenyl. The aspect has the further proviso that when M1 is oxygen, W1 is a member selected from $(CR^{3a}R^{4a})_{n1}$, wherein n1 is 0, J1 is a member selected from $(CR^{6a}R^{7a})_{m1}$, wherein m1 is 1, A1 is $CR^{9a}$, D1 is $CR^{10a}$, E1 is $CR^{11a}$, G1 is $CR^{12a}$, and $R^{9a}$, $R^{10a}$ and $R^{11a}$ are H, then $R^{6a}$, $R^{7a}$ and $R^{12a}$ are not H. The aspect has the further proviso that when M1 is oxygen wherein n1 is 1, J1 is a member selected from $(CR^{6a}R^{7a})_{m1}$, wherein m1 is 0, A1 is $CR^{9a}$, D1 is $CR^{10a}$, E1 is $CR^{11a}$, G1 is $CR^{12a}$, $R^{9a}$ is H, $R^{10a}$ is H, $R^{11a}$ is H, $R^{6a}$ is H, $R^{7a}$ is H, $R^{12a}$ is H, then W1 is not C=O (carbonyl). The aspect has the further proviso that when M1 is oxygen, W1 is $CR^{5a}$, J1 is $CR^{8a}$, A1 is $CR^{9a}$, D1 is $C^{10a}$, E1 is $CR^{11a}$, G1 is $CR^{12a}$, $R^{6a}$, $R^{7a}$, $R^{9a}$, $R^{10a}$, $R^{11a}$ and $R^{12a}$ are H, then $R^{5a}$ and $R^{8a}$, together with the atoms to which they are attached, do not form a phenyl ring.

In an exemplary embodiment, the compound has a structure according to Formula (Ia):

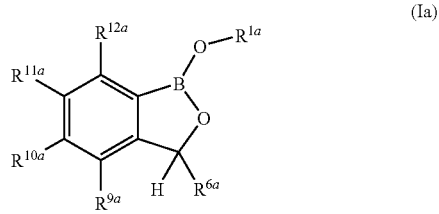

(Ia)

wherein B is boron. $R^{1a}$ is a member selected from a negative charge, a salt counterion, H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. $R^{6a}$ are members independently selected from H, OH, $NH_2$, SH, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. $R^{9a}$, $R^{10a}$, $R^{11a}$ and $R^{12a}$ are members independently selected from H, OH, $NH_2$, SH, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. $R^{9a}$ and $R^{10a}$, together with the atoms to which they are attached, are optionally joined to form a 4 to 7 membered ring. $R^{10a}$ and $R^{11a}$, together with the atoms to which they are attached, are optionally joined to form a 4 to 7 membered ring. $R^{11a}$ and $R^{12a}$, together with the atoms to which they are attached, are optionally joined to form a 4 to 7 membered ring. This embodiment has the proviso that $R^{9a}$ is not halogen, methyl, ethyl, or optionally joined with $R^{10a}$ to form a 4 to 7 membered ring. This embodiment has the proviso that $R^{10a}$ is not unsubstituted phenoxy, $C(CH_3)_3$, halogen, $CF_3$, methoxy, ethoxy, optionally joined with $R^{9a}$ to form a 4 to 7 membered ring, or optionally joined with $R^{11a}$ to form a 4 to 7 membered ring. This embodiment has the proviso that $R^{11a}$ is not halogen or optionally joined with $R^{10a}$ to form a 4 to 7 membered ring. This embodiment has the proviso that $R^{12a}$ is not halogen.

In an exemplary embodiment, the compound has a structure according to Formula (Ib):

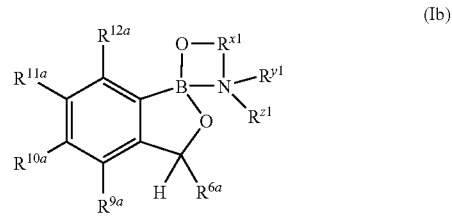

(Ib)

wherein B is boron. $R^{x1}$ is a member selected from substituted or unsubstituted $C_1$-$C_5$ alkyl, substituted or unsubstituted $C_1$-$C_5$ heteroalkyl. $R^{y1}$ and $R^{z1}$ are members independently selected from H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. $R^{6a}$ are members independently selected from H, OH, $NH_2$, SH, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. $R^{9a}$, $R^{10a}$, $R^{11a}$ and $R^{12a}$ are members independently selected from H, OH, $NH_2$, SH, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. $R^{11a}$ and $R^{12a}$, together with the atoms to which they are attached, are optionally joined to form a 4 to 7 membered ring. This embodiment has the proviso that when $R^{9a}$, $R^{11a}$ and $R^{12a}$ are H, $R^{10a}$ is not H, halogen, unsubstituted phenoxy or t-butyl. This embodiment has the further proviso that when $R^{9a}$ is H, $R^{10a}$ and $R^{11a}$ together with the atoms to which they are attached, are not joined to form a phenyl ring. This embodiment has the further proviso that when $R^{11a}$ is H, $R^{9a}$ and $R^{10a}$ together with the atoms to which they are attached, are not joined to form a phenyl ring.

In another aspect, the invention provides a compound having a structure according to Formula II:

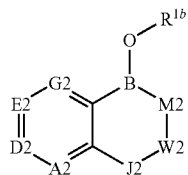
(II)

wherein B is boron. $R^{1b}$ is a member selected from a negative charge, a salt counterion, H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. M2 is a member selected from oxygen, sulfur and $NR^{2b}$. $R^{2b}$ is a member selected from H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. J2 is a member selected from $(CR^{3b}R^{4b})_{n2}$ and $CR^{5b}$. $R^{3b}$, $R^{4b}$, and $R^{5b}$ are members independently selected from H, OH, $NH_2$, SH, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. The index n2 is an integer selected from 0 to 2. W2 is a member selected from C=O (carbonyl), $(CR^{6b}R^{7b})_{n2}$ and $CR^{8b}$. $R^{6b}$, $R^{7b}$, and $R^{8b}$ are members independently selected from H, OH, $NH_2$, SH, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. The index m2 is an integer selected from 0 and 1. A2 is a member selected from $CR^{9b}$ and N. D2 is a member selected from $CR^{10b}$ and N. E2 is a member selected from $CR^{11b}$ and N. G2 is a member selected from $CR^{12b}$ and N. $R^{9b}$, $R^{10b}$, $R^{11b}$ and $R^{12b}$ are members independently selected from H, OH, $NH_2$, SH, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. The combination of nitrogens (A2+D2+E2+G2) is an integer selected from 0 to 3. A member selected from $R^{3b}$, $R^{4b}$ and $R^{5b}$ and a member selected from $R^{6b}$, $R^{7b}$ and $R^{8b}$, together with the atoms to which they are attached, are optionally joined to form a 4 to 7 membered ring. $R^{3b}$ and $R^{4b}$, together with the atoms to which they are attached, are optionally joined to form a 4 to 7 membered ring. $R^{6b}$ and $R^{7b}$, together with the atoms to which they are attached, are optionally joined to form a 4 to 7 membered ring. $R^{9b}$ and $R^{10b}$, together with the atoms to which they are attached, are optionally joined to form a 4 to 7 membered ring. $R^{10b}$ and $R^{11b}$, together with the atoms to which they are attached, are optionally joined to form a 4 to 7 membered ring. $R^{11b}$ and $R^{12b}$, together with the atoms to which they are attached, are optionally joined to form a 4 to 7 membered ring.

In an exemplary embodiment, the aspect has the proviso that when M2 is oxygen, W2 is a member selected from $(CR^{3b}R^{4b})_{n2}$, wherein n2 is 0, J2 is a member selected from $(CR^{6b}R^{7b})_{n2}$, wherein m2 is 1, A2 is $CR^{9b}$, D2 is $CR^{10b}$, E is $CR^{11b}$, G is $CR^{12b}$, then $R^{9b}$ is not a member selected from halogen, methyl, ethyl, or optionally joined with $R^{10b}$ to a form phenyl ring. In another exemplary embodiment, the aspect has the proviso that when M2 is oxygen, W2 is a member selected from $(CR^{3b}R^{4b})_n$, wherein n2 is 0, J2 is a member selected from $(CR^{6b}R^{7b})_m$, wherein m2 is 1, A2 is $CR^{9b}$, D2 is $CR^{10b}$, E2 is $CR^{11b}$, G2 is $CR^{12b}$, then $R^{11b}$ is not a member selected from unsubstituted phenoxy, $C(CH_3)_3$, halogen, $CF_3$, methoxy, ethoxy, or optionally joined with $R^{9b}$ to form a phenyl ring. In another exemplary embodiment, the aspect has the proviso that when M2 is oxygen, W2 is a member selected from $(CR^{3b}R^{4b})$, wherein n2 is 0, J2 is a member selected from $(CR^{6b}R^{7b})_{m2}$, wherein m2 is 1, A2 is $CR^{9b}$, D2 is $CR^{10b}$, E2 is $CR^{11b}$, G2 is $CR^{12b}$, then $R^{10b}$ is not a member selected from halogen or optionally joined with $R^{10b}$ to form a phenyl ring. In another exemplary embodiment, the aspect has the proviso that when M2 is oxygen, W2 is a member selected from $(CR^{3b}R^{4a})_{n2}$, wherein n2 is 0, J2 is a member selected from $(CR^{6b}R^{7b})$, wherein m2 is 1, A2 is $CR^{9b}$, D2 is $CR^{10b}$, E2 is $CR^{11b}$, G2 is $CR^{12}$, then $R^{12b}$ is not halogen. In another exemplary embodiment, the aspect has the proviso that when M2 is oxygen, W2 is a member selected from $(CR^{3b}R^{4b})_{n2}$, wherein n2 is 0, J2 is a member selected from $(CR^{6b}R^{7b})_2$, wherein m2 is 1, A2 is $CR^{9b}$, D2 is $CR^{10b}$, E2 is $CR^{11b}$, G2 is $CR^{12b}$, then $R^{6b}$ is not halophenyl. In another exemplary embodiment, the aspect has the proviso that when M2 is oxygen, W2 is a member selected from $(CR^{3b}R^{4b})_{n2}$, wherein n2 is 0, J2 is a member selected from $(CR^{6b}R^{7b})_{m2}$, wherein m2 is 1, A2 is $CR^{9b}$, D2 is $CR^{10b}$, E2 is $CR^{11b}$, G2 is $CR^{12b}$, then $R^{7b}$ is not halophenyl. In another exemplary embodiment, the aspect has the proviso that when M2 is oxygen, W2 is a member selected from $(CR^{3b}R^{4b})_{n2}$, wherein n2 is 0, J2 is a member selected from $(CR^{6b}R^{7b})_{m2}$, wherein m2 is 1, A2 is $CR^{9b}$, D2 is $CR^{10b}$, E2 is $CR^{11b}$, G2 is $CR^{12b}$, then $R^{6b}$ and $R^{7b}$ are not halophenyl. In another exemplary embodiment, the aspect has the proviso that when M2 is oxygen, W2 is a member selected from $(CR^{3b}R^{4b})_{n2}$, wherein n2 is 0, J2 is a member selected from $(CR^{6b}R^{7b})_{m2}$, wherein m2 is 1, A2 is $CR^{9b}$, D2 is $CR^{10b}$, E2 is $CR^{11b}$, G2 is $CR^{12b}$, and $R^{9b}$, $R^{10b}$ and $R^{11b}$ are H, then $R^{6b}$, $R^{7b}$ and $R^{12b}$ are not H. In another exemplary embodiment, the aspect has the proviso that when M2 is oxygen wherein n2 is 1, J2 is a member selected from $(CR^{6b}R^{7b})_{m2}$, wherein m2 is 0, A2 is $CR^{9b}$, D2 is $CR^{10b}$, E2 is $CR^{11b}$, G2 is $CR^{12b}$, $R^{9b}$ is H, $R^{10b}$ is H, $R^{11b}$ is H, $R^{6b}$ is H, $R^{7b}$ is H, $R^{12b}$ is H, then W2 is not C=O (carbonyl). In another exemplary embodiment, the aspect has the proviso that when M2 is oxygen, W2 is $CR^{5b}$, J2 is $CR^{8b}$, A2 is $CR^{9b}$, D2 is $CR^{10b}$, E2 is $CR^{11b}$, G2 is $CR^{12b}$, $R^{6b}$, $R^{7b}$, $R^{9b}$, $R^{10b}$, $R^{11b}$ and $R^{12b}$ are H, then $R^{5b}$ and $R^{8b}$, together with the atoms to which they are attached, do not form a phenyl ring.

In an exemplary embodiment, the compound with a structure according to Formula (IIa):

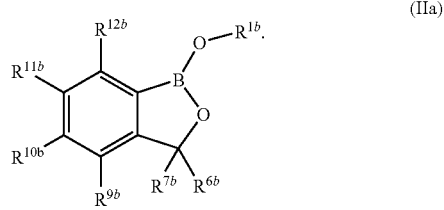
(IIa)

In another exemplary embodiment, the compound has a structure according to Formula (IIb):

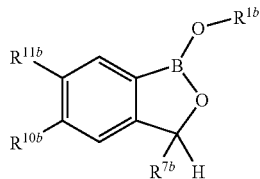

(IIb)

wherein $R^{7b}$ is a member selected from H, methyl, ethyl and phenyl. $R^{10b}$ is a member selected from H, OH, $NH_2$, SH, halogen, substituted or unsubstituted phenoxy, substituted or unsubstituted phenylalkyloxy, substituted or unsubstituted phenylthio and substituted or unsubstituted phenylalkylthio. $R^{11b}$ is a member selected from H, OH, $NH_2$, SH, methyl, substituted or unsubstituted phenoxy, substituted or unsubstituted phenylalkyloxy, substituted or unsubstituted phenylthio and substituted or unsubstituted phenylalkylthio.

In another exemplary embodiment, $R^{1b}$ is a member selected from a negative charge, H and a salt counterion. In another exemplary embodiment, $R^{10b}$ and $R^{11b}$ are H. In another exemplary embodiment, one member selected from $R^{10b}$ and $R^{11b}$ is H and the other member selected from $R^{10b}$ and $R^{11b}$ is a member selected from halo, methyl, cyano, methoxy, hydroxymethyl and p-cyanophenyloxy. In another exemplary embodiment, $R^{10b}$ and $R^{11b}$ are members independently selected from fluoro, chloro, methyl, cyano, methoxy, hydroxymethyl, and p-cyanophenyl. In another exemplary embodiment, $R^{1b}$ is a member selected from a negative charge, H and a salt counterion; $R^{7b}$ is H; $R^{10b}$ is F and $R^{11b}$ is H. In another exemplary embodiment, $R^{11b}$ and $R^{12b}$, along with the atoms to which they are attached, are joined to form a phenyl group. In another exemplary embodiment, $R^{1b}$ is a member selected from a negative charge, H and a salt counterion; $R^{7b}$ is H; $R^{10b}$ is 4-cyanophenoxy; and $R^{11b}$ is H.

In another exemplary embodiment, the compound has a structure according to Formula (IIc):

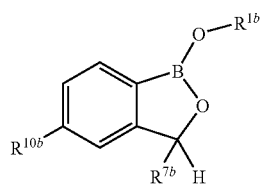

(IIc)

wherein $R^{10b}$ is a member selected from H, halogen, CN and substituted or unsubstituted $C_{1-4}$ alkyl. In another exemplary embodiment, the compound has a formulation which is a member selected from:

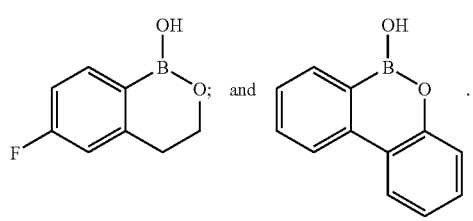

In another exemplary embodiment, the compound has a structure according to Formula (IId):

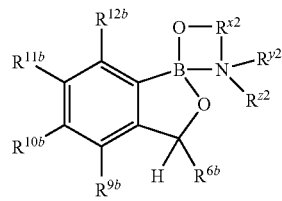

(IId)

wherein B is boron. $R^{x2}$ is a member selected from substituted or unsubstituted $C_1-C_5$ alkyl and substituted or unsubstituted $C_1-C_5$ heteroalkyl. $R^{y2}$ and $R^{z2}$ are members independently selected from H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

The compounds of Formulae (I) or (II) can form a hydrate with water, solvates with alcohols such as methanol, ethanol, propanol, and the like; adducts with amino compounds, such as ammonia, methylamine, ethylamine, and the like; adducts with acids, such as formic acid, acetic acid and the like; complexes with ethanolamine, quinoline, amino acids, and the like.

Preparation of Boron-Containing Small Molecules

The following exemplary schemes illustrate methods of preparing boron-containing molecules of the present invention. These methods are not limited to producing the compounds shown, but can be used to prepare a variety of molecules such as the compounds and complexes described herein. The compounds of the present invention can also be synthesized by methods not explicitly illustrated in the schemes but are well within the skill of one in the art. The compounds can be prepared using readily available materials of known intermediates.

In the following schemes, the symbol X represents bromo or iodo. The symbol Y is selected from H, lower alkyl, and arylalkyl. The symbol Z is selected from H, alkyl, and aryl. The symbol PG represents protecting group. The symbols A, D, E, G, $R^x, R^y, R^z, R^1, R^2, R^3, R^4, R^5, R^6, R^7, R^8, R^9, R^{10}, R^{11}$ and $R^{12}$ can be used to refer to the corresponding symbols in Formulae (I) or (II). For example, the symbol A can refer to A1 of Formula (I), or A2 of Formula (II), subject to the provisos of each Formula.

Preparation Strategy #1

In Scheme 1, Step 1 and 2, compounds 1 or 2 are converted into alcohol 3. In step 1, compound 1 is treated with a reducing agent in an appropriate solvent. Suitable reducing agents include borane complexes, such as borane-tetrahydrofuran, borane-dimethylsulfide, combinations thereof and the like. Lithium aluminum hydride, or sodium borohydride can also be used as reducing agents. The reducing agents can be used in quantities ranging from 0.5 to 5 equivalents, relative to compound 1 or 2. Suitable solvents include diethyl ether, tetrahydrofuran, 1,4-dioxane, 1,2-dimethoxyethane, combinations thereof and the like. Reaction temperatures range from 0° C. to the boiling point of the solvent used; reaction completion times range from 1 to 24 h.

In Step 2, the carbonyl group of compound 2 is treated with a reducing agent in an appropriate solvent. Suitable reducing agents include borane complexes, such as borane-tetrahydrofuran, borane-dimethylsulfide, combinations thereof and the like. Lithium aluminum hydride, or sodium borohydride can also be used as reducing agents. The reducing agents can be used in quantities ranging from 0.5 to 5 equivalents, relative to compound 2. Suitable solvents include lower alcohol, such as methanol, ethanol, and propanol, diethyl ether, tetrahydrofuran, 1,4-dioxane and 1,2-dimethoxyethane, combinations thereof and the like. Reaction temperatures range from 0° C. to the boiling point of the solvent used; reaction completion times range from 1 to 24 h.

In Step 3, the hydroxyl group of compound 3 is protected with a protecting group which is stable under neutral or basic conditions. The protecting group is typically selected from methoxymethyl, ethoxyethyl, tetrahydropyran-2-yl, trimethylsilyl, tert-butyldimethylsilyl, tributylsilyl, combinations thereof and the like. In the case of methoxymethyl, compound 3 is treated with 1 to 3 equivalents of chloromethyl methyl ether in the presence of a base. Suitable bases include sodium hydroxide, potassium tert-butoxide, tertiary amines, such as diisopropylethylamine, triethylamine, 1,8-diazabicyclo[5,4,0]undec-7-ene, and inorganic bases, such as sodium hydroxide, sodium carbonate, potassium hydroxide, potassium carbonate, combinations thereof and the like. The bases can be used in quantities ranging from 1 to 3 equivalents, relative to compound 3. Reaction temperatures range from 0° C. to the boiling point of the solvent used; preferably between 0 and 40° C.; reaction completion times range from 1 to 48 h.

In the case of tetrahydropyran-2-yl, compound 3 is treated with 1 to 3 equivalents of 3,4-dihydro-2H-pyran in the presence of 1 to 10 mol % of acid catalyst. Suitable acid catalysts include pyridinium p-toluenesulfonic acid, p-toluenesulfonic acid, camphorsulfonic acid, hydrogen chloride, sulfuric acid, combinations thereof and the like. Suitable solvents include dichloromethane, chloroform, tetrahydrofuran, 1,4-dioxane, 1,2-dimethoxyethane, toluene, benzene, and acetonitrile combinations thereof and the like. Reaction temperatures range from 0° C. to the boiling point of the solvent used; preferably between 0 and 40° C., and is complete in 1 to 48 h.

In the case of trialkylsilyl, compound 3 is treated with 1 to 3 equivalents of chlorotrialkylsilylane in the presence of 1 to 3 equivalents of base. Suitable bases include tertiary amines, such as imidazole, diisopropylethylamine, triethylamine, 1,8-diazabicyclo[5,4,0]undec-7-ene, combinations thereof and the like. Reaction temperatures range from 0° C. to the boiling point of the solvent used; preferably between 0 and 40° C.; reaction completion times range from 1 to 48 h.

In Step 4, compound 4 is converted into boronic acid (5) through halogen metal exchange reaction. Compound 4 is treated with 1 to 3 equivalents of alkylmetal reagent relative to compound 4, such as n-butyllithium, sec-butyllithium, tert-butyllithium, or isopropylmagnesium chloride followed by the addition of 1 to 3 equivalents of trialkyl borate relative to compound 4, such as trimethyl borate, triisopropyl borate, or tributyl borate. Suitable solvents include tetrahydrofuran, ether, 1,4-dioxane, 1,2-dimethoxyethane, toluene, hexanes, combinations thereof and the like. Alkylmetal reagent may also be added in the presence of trialkyl borate. The addition of butyllithium is carried out at between −100 and 0° C., preferably at between −80 and −40° C. The addition of isopropylmagnesium chloride is carried out at between −80 and 40° C., preferably at between −20 and 30° C. After the addition of trialkyl borate, the reaction is allowed to warm to room temperature, which is typically between 15 and 30° C. When alkylmetal reagent is added in the presence of trialkyl borate, the reaction mixture is allowed to warm to room temperature after the addition. Reaction completion times range from 1 to 12 h. Compound 5 may not be isolated and may be used for the next step without purification or in one pot.

In Step 5, the protecting group of compound 5 is removed under acidic conditions to give compound of Formulae (I) and (II). Suitable acids include acetic acid, trifluoroacetic acid, hydrochloric acid, hydrobromic acid, sulfuric acid, p-toluenesulfonic acid and the like. The acids can be used in quantities ranging from 0.1 to 20 equivalents, relative to compound 5. When the protecting group is trialkylsilyl, basic reagents, such as tetrabutylammonium fluoride, can also be used. Suitable solvents include tetrahydrofuran, 1,4-dioxane, 1,2-dimethoxyethane, methanol, ethanol, propanol, acetonitrile, acetone, combination thereof and the like. Reaction temperatures range from 0° C. to the boiling point of the solvent used; preferably between 10 and 40° C.; reaction completion times range from 0.5 to 48 h.

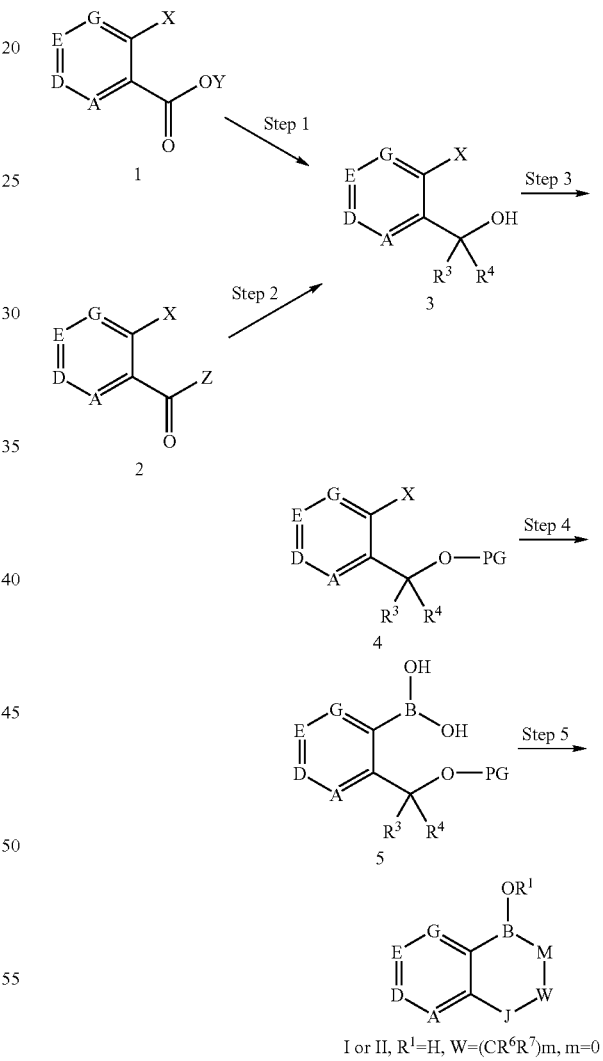

Preparation Strategy #2

In Scheme 2, Step 6, compound 2 is converted into boronic acid (6) via a transition metal catalyzed cross-coupling reaction. Compound 2 is treated with 1 to 3 equivalents of bis (pinacolato)diboron or 4,4,5,5-tetramethyl-1,3,2-dioxaborolane in the presence of transition metal catalyst, with the use of appropriate ligand and base as necessary. Suitable transition metal catalysts include palladium(II) acetate, palladium (II) acetoacetonate, tetrakis(triphenylphosphine)palladium, dichlorobis(triphenylphosphine)palladium, [1,1'-bis(diphenylphosphino)ferrocen]dichloropalladium(II), combinations thereof and the like. The catalyst can be used in quantities ranging from 1 to 5 mol % relative to compound 2. Suitable ligands include triphenylphosphine, tri(o-tolyl)phosphine, tricyclohexylphosphine, combinations thereof and the like. The ligand can be used in quantities ranging from 1 to 5 equivalents relative to compound 2. Suitable bases include sodium carbonate, potassium carbonate, potassium phenoxide, triethylamine, combinations thereof and the like. The base can be used in quantities ranging from 1 to 5 equivalents relative to compound 2. Suitable solvents include N,N-dimethylformamide, dimethylsulfoxide, tetrahydrofuran, 1,4-dioxane, toluene, combinations thereof and the like. Reaction temperatures range from 20° C. to the boiling point of the solvent used; preferably between 50 and 150° C.; reaction completion times range from 1 to 72 h.

Pinacol ester is then oxidatively cleaved to give compound 6. Pinacol ester is treated with sodium periodate followed by acid. Sodium periodate can be used in quantities ranging from 2 to 5 equivalents relative to compound 6. Suitable solvents include tetrahydrofuran, 1,4-dioxane, acetonitrile, methanol, ethanol, combinations thereof and the like. Suitable acids include hydrochloric acid, hydrobromic acid, sulfuric acid combinations thereof and the like. Reaction temperatures range from 0° C. to the boiling point of the solvent used; preferably between 0 and 50° C.; reaction completion times range from 1 to 72 h.

In Step 7, the carbonyl group of compound 6 is treated with a reducing agent in an appropriate solvent to give a compound of Formulae (I) and (II). Suitable reducing agents include borane complexes, such as borane-tetrahydrofuran, borane-dimethylsulfide, combinations thereof and the like. Lithium aluminum hydride, or sodium borohydride can also be used as reducing agents. The reducing agents can be used in quantities ranging from 0.5 to 5 equivalents, relative to compound 6. Suitable solvents include lower alcohol, such as methanol, ethanol, and propanol, diethyl ether, tetrahydrofuran, 1,4-dioxane and 1,2-dimethoxyethane, combinations thereof and the like. Reaction temperatures range from 0° C. to the boiling point of the solvent used; reaction completion times range from 1 to 24 h.

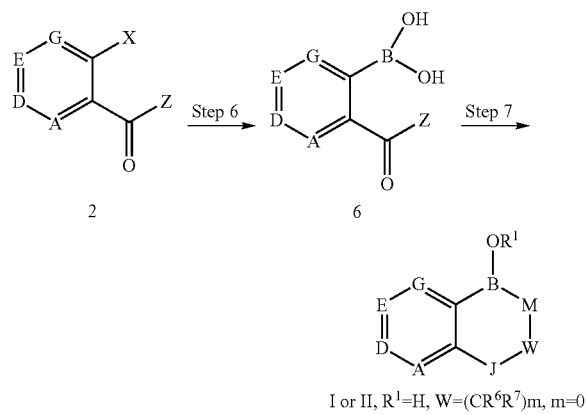

Preparation Strategy #3

In Scheme 3, Step 8, compounds of Formulae (I) and (II) can be prepared in one step from compound 3. Compound 3 is mixed with trialkyl borate then treated with alkylmetal reagent. Suitable alkylmetal reagents include n-butyllithium, sec-butyllithium, tert-butyllithium combinations thereof and the like. Suitable trialkyl borates include trimethyl borate, triisopropyl borate, tributyl borate, combinations thereof and the like. The addition of butyllithium is carried out at between −100 and 0° C., preferably at between −80 and −40° C. The reaction mixture is allowed to warm to room temperature after the addition. Reaction completion times range from 1 to 12 h. The trialkyl borate can be used in quantities ranging from 1 to 5 equivalents relative to compound 3. The alkylmetal reagent can be used in quantities ranging from 1 to 2 equivalents relative to compound 3. Suitable solvents include tetrahydrofuran, ether, 1,4-dioxane, 1,2-dimethoxyethane, toluene, hexanes, combinations thereof and the like. Reaction completion times range from 1 to 12 h. Alternatively, a mixture of compound 3 and trialkyl borate can be refluxed for 1 to 3 h and the alcohol molecule formed upon the ester exchange can be distilled out before the addition of alkylmetal reagent.

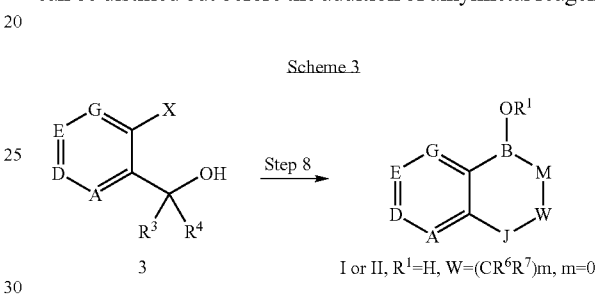

Preparation Strategy #4

In Scheme 4, Step 10, the methyl group of compound 7 is brominated using N-bromosuccinimide. N-bromosuccinimide can be used in quantities ranging from 0.9 to 1.2 equivalents relative to compound 7. Suitable solvents include carbon tetrachloride, tetrahydrofuran, 1,4-dioxane, chlorobenzene, combinations thereof and the like. Reaction temperatures range from 20° C. to the boiling point of the solvent used; preferably between 50 and 150° C.; reaction completion times range from 1 to 12 h.

In Step 11, the bromomethylene group of compound 8 is converted to the benzyl alcohol 3. Compound 8 is treated with sodium acetate or potassium acetate. These acetates can be used in quantities ranging from 1 to 10 equivalents relative to compound 8. Suitable solvents include tetrahydrofuran, 1,4-dioxane, N,N-dimethylformamide, N,N-dimethylacetamide, N-methylpyrrolidone, dimethylsulfoxide, combinations thereof and the like. Reaction temperatures range from 20° C. to the boiling point of the solvent used; preferably between 50 and 100° C.; reaction completion times range from 1 to 12 h. The resulting acetate is hydrolyzed to compound 3 under basic conditions. Suitable bases include sodium hydroxide, lithium hydroxide, potassium hydroxide, combinations thereof and the like. The base can be used in quantities ranging from 1 to 5 equivalents relative to compound 8. Suitable solvents include methanol, ethanol, tetrahydrofuran, water, combinations thereof and the like. Reaction temperatures range from 20° C. to the boiling point of the solvent used; preferably between 50 and 100° C.; reaction completion times range from 1 to 12 h. Alternatively, compound 8 can be directly converted into compound 3 under the similar condition above.

Steps 3 through 5 convert compound 3 into a compound of Formulae (I) and (II).

Scheme 4

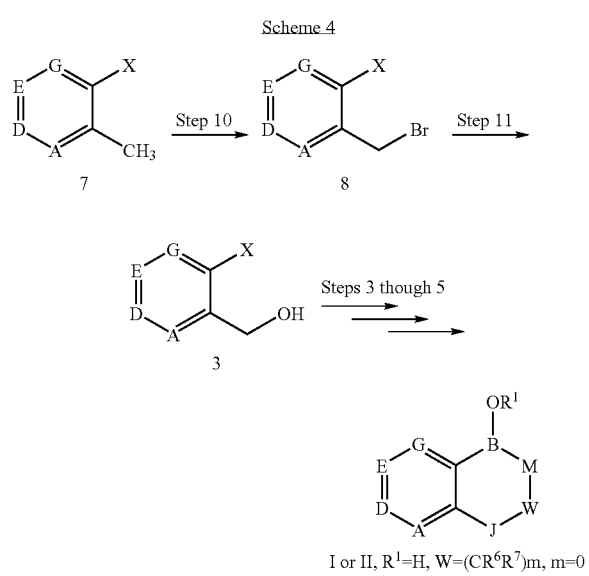

I or II, R$^1$=H, W=(CR$^6$R$^7$)m, m=0

Preparation Strategy #5

In Scheme 5, Step 12, compound 2 is treated with (methoxymethyl) triphenylphosphonium chloride or (methoxymethyl)triphenylphosphonium bromide in the presence of base followed by acid hydrolysis to give compound 9. Suitable bases include sodium hydride, potassium tert-butoxide, lithium diisopropylamide, butyllithium, lithium hexamethyldisilazane, combinations thereof and the like. The (methoxymethyl)triphenylphosphonium salt can be used in quantities ranging from 1 to 5 equivalents relative to compound 2. The base can be used in quantities ranging from 1 to 5 equivalents relative to compound 2. Suitable solvents include tetrahydrofuran, 1,2-dimethoxyethane, 1,4-dioxane, ether, toluene, hexane, N,N-dimethylformamide, combinations thereof and the like. Reaction temperatures range from 0° C. to the boiling point of the solvent used; preferably between 0 and 30° C.; reaction completion times range from 1 to 12 h. The enolether formed is hydrolyzed under acidic conditions. Suitable acids include hydrochloric acid, hydrobromic acid, sulfuric acid, and the like. Suitable solvents include tetrahydrofuran, 1,2-dimethoxyethane, 1,4-dioxane, methanol, ethanol, combination thereof and the like. Reaction temperatures range from 20° C. to the boiling point of the solvent used; preferably between 50 and 100° C.; reaction completion times range from 1 to 12 h.

Steps 2 through 5 convert compound 9 into a compound of Formulae (I) and (II).

Scheme 5

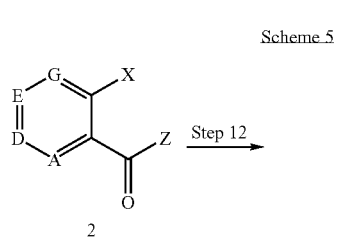

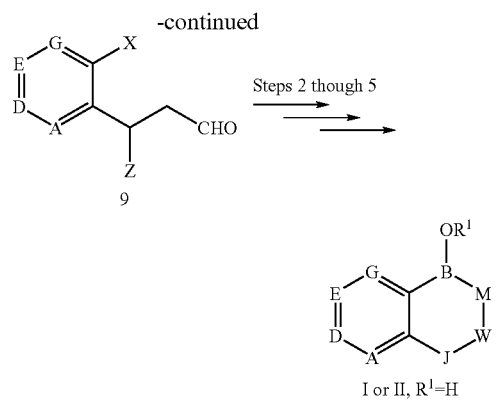

Preparation Strategy #6

In Scheme 6, compound (I) wherein R$^1$ is H is converted into compound (I) wherein R$^1$ is alkyl by mixing with the corresponding alcohol, R$^1$OH. The suitable solvents include tetrahydrofuran, 1,2-dimethoxyethane, 1,4-dioxane, toluene, combinations thereof and the like. The alcohol (R$^1$OH) can be used as the solvent as well. Reaction temperatures range from 20° C. to the boiling point of the solvent used; preferably between 50 and 100° C.; reaction completion times range from 1 to 12 h.

Scheme 6

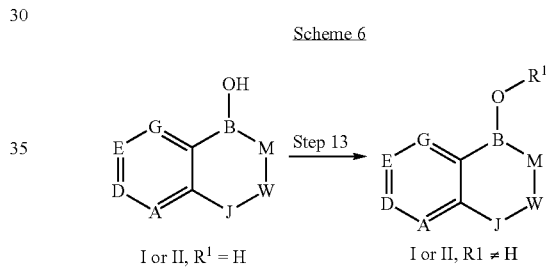

Preparation Strategy #7

In Scheme 7, compound (Ia) is converted into its aminoalcohol complex (Ib). Compound (Ia) is treated with HOR$^1$NR$^{1a}$R$^{1b}$. The aminoalcohol can be used in quantities ranging from 1 to 10 equivalents relative to compound (Ia). Suitable solvents include methanol, ethanol, propanol, tetrahydrofuran, acetone, acetonitrile, 1,2-dimethoxyethane, 1,4-dioxane, toluene, N,N-dimethylformamide, water, combination thereof and the like. Reaction temperatures range from 20° C. to the boiling point of the solvent used; preferably between 50 and 100° C.; reaction completion times range from 1 to 24 h.

Scheme 7

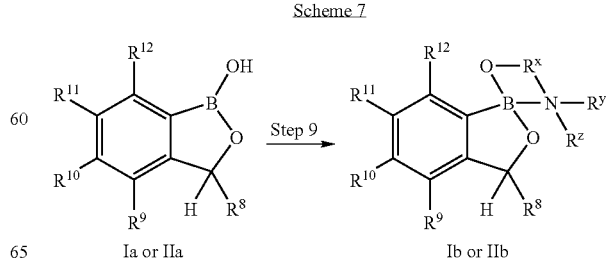

The compounds of Formulae (I) or (II) can be converted into hydrates and solvates by methods similar to those described above.

IV. Methods of Inhibiting Microorganism Growth or Killing Microorganisms

In another aspect, the invention provides a method of inhibiting the growth of a microorganism, or killing a microorganism, or both, comprising contacting the microorganism with a compound according to Formulae (I) or (II). Microorganisms are members selected from fungi, yeast, viruses, bacteria and parasites. In another exemplary embodiment, the microorganism is inside, or on the surface of an animal. In an exemplary embodiment, the animal is a member selected from human, cattle, deer, reindeer, goat, honey bee, pig, sheep, horse, cow, bull, dog, guinea pig, gerbil, rabbit, cat, camel, yak, elephant, ostrich, otter, chicken, duck, goose, guinea fowl, pigeon, swan, and turkey. In another exemplary embodiment, the animal is a human.

In an exemplary embodiment, the microorganism is a member selected from a fungus and a yeast. In another exemplary embodiment, the fungus or yeast is a member selected from *Candida* species, *Trichophyton* species, *Microsporium* species, *Aspergillus* species, *Cryptococcus* species, *Blastomyces* species, *Cocciodiodes* species, *Histoplasma* species, *Paracoccidiodes* species, *Phycomycetes* species, *Malassezia* species, *Fusarium* species, *Epidermophyton* species, *Scytalidium* species, *Scopulariopsis* species, *Alternaria* species, *Penicillium* species, *Phialophora* species, *Rhizopus* species, *Scedosporium* species and Zygomycetes class. In another exemplary embodiment, the fungus or yeast is a member selected from *Aspergilus fumigatus* (*A. fumigatus*), *Blastomyces dermatitidis*, *Candida Albicans* (*C. albicans*, both fluconazole sensitive and resistant strains), *Candida glabrata* (*C. glabrata*), *Candida krusei* (*C. krusei*), *Cryptococcus neoformans* (*C. neoformans*), *Candida parapsilosis* (*C. parapsilosis*), *Candida tropicalis* (*C. tropicalis*), *Cocciodiodes immitis*, *Epidermophyton floccosum* (*E. floccosum*), *Fusarium solani* (*F. solani*), *Histoplasma capsulatum*, *Malassezia furfur* (*M. furfur*), *Malassezia pachydermatis* (*M. pachydermatis*), *Malassezia sympodialis* (*M. sympodialis*), *Microsporum audouinii* (*M. audouinii*), *Microsporum canis* (*M. canis*), *Microsporum gypseum* (*M. gypseum*), *Paracoccidiodes brasiliensis* and *Phycomycetes* spp, *Trichophyton mentagrophytes* (*T. mentagrophytes*), *Trichophyton rubrum* (*T. rubrum*), *Trichophyton tonsurans* (*T. tonsurans*). In another exemplary embodiment, the fungus or yeast is a member selected from *Trichophyton concentricum*, *T. violaceum*, *T. schoenleinii*, *T. verrucosum*, *T. soudanense*, *Microsporum gypseum*, *M. equinum*, *Candida guilliermondii*, *Malassezia globosa*, *M. obtuse*, *M. restricta*, *M. slooffiae*, and *Aspergillus flavus*. In another exemplary embodiment, the fungus or yeast is a member selected from dermatophytes, *Trichophyton*, *Microsporum*, *Epidermophyton* and yeast-like fungi.

In an exemplary embodiment, the microorganism is a bacteria. In an exemplary embodiment, the bacteria is a gram-positive bacteria. In another exemplary embodiment, the gram-positive bacteria is a member selected from *Staphylococcus* species, *Streptococcus* species, *Bacillus* species, *Mycobacterium* species, *Corynebacterium* species (*Propionibacterium* species), *Clostridium* species, *Actinomyces* species, *Enterococcus* species and *Streptomyces* species. In another exemplary embodiment, the bacteria is a gram-negative bacteria. In another exemplary embodiment, the gram-negative bacteria is a member selected from *Acinetobacter* species, *Neisseria* species, *Pseudomonas* species, *Brucella* species, *Agrobacterium* species, *Bordetella* species, *Escherichia* species, *Shigelia* species, *Yersinia* species, *Salmonella* species, *Klebsiella* species, *Enterobacter* species, *Haemophilus* species, *Pasteurella* species, *Streptobacillus* species, *spirochetal* species, *Campylobacter* species, *Vibrio* species and *Helicobacter* species. In another exemplary embodiment, the bacterium is a member selected from *Propionibacterium acnes*; *Staphylococcus aureus*; *Staphylococcus epidermidis*, *Staphylococcus saprophyticus*; *Streptococcus pyogenes*; *Streptococcus agalactiae*; *Streptococcus pneumoniae*; *Enterococcus faecalis*; *Enterococcus faecium*; *Bacillus anthracis*; *Mycobacterium avium-intracellulare*; *Mycobacterium tuberculosis*, *Acinetobacter baumanii*; *Corynebacterium diphtheria*; *Clostridium perfringens*; *Clostridium botulinum*; *Clostridium tetani*; *Neisseria gonorrhoeae*; *Neisseria meningitidis*; *Pseudomonas aeruginosa*; *Legionella pneumophila*; *Escherichia coli*; *Yersinia pestis*; *Haemophilus influenzae*; *Helicobacter pylori*; *Campylobacter fetus*; *Campylobacter jejuni*; *Vibrio cholerae*; *Vibrio parahemolyticus*; *Trepomena pallidum*; *Actinomyces israelii*; *Rickettsia prowazekii*; *Rickettsia rickettsii*; *Chlamydia trachomatis*; *Chlamydia psittaci*; *Brucella abortus*; *Agrobacterium tumefaciens*; and *Francisella tularensis*.

In an exemplary embodiment, the microorganism is a bacteria, which is a member selected from acid-fast bacterium, including *Mycobacterium* species; bacilli, including *Bacillus* species, *Corynebacterium* species (also *Propionibacterium*) and *Clostridium* species; filamentous bacteria, including *Actinomyces* species and *Streptomyces* species; bacilli, such as *Pseudomonas* species, *Brucella* species, *Agrobacterium* species, *Bordetella* species, *Escherichia* species, *Shigella* species, *Yersinia* species, *Salmonella* species, *Klebsiella* species, *Enterobacter* species, *Haemophilus* species, *Pasteurella* species, and *Streptobacillus* species; spirochetal species, *Campylobacter* species, *Vibrio* species; and intracellular bacteria including *Rickettsiae* species and *Chlamydia* species.

In an exemplary embodiment, the microorganism is a virus. In an exemplary embodiment, the virus is a member selected from hepatitis A-B, human rhinoviruses, Yellow fever virus, human respiratory coronaviruses, Severe acute respiratory syndrome (SARS), respiratory syncytial virus, influenza viruses, parainfluenza viruses 1-4, human immunodeficiency virus 1 (HIV-1), human immunodeficiency virus 2 (HIV-2), Herpes simplex virus 1 (HSV-1), Herpes simplex virus 2 (HSV-2), human cytomegalovirus (HCMV), Varicella zoster virus, Epstein-Barr (EBV), polioviruses, coxsackieviruses, echoviruses, rubella virus, neuroderma-tropic virus, variola virus, papoviruses, rabies virus, dengue virus, West Nile virus and SARS virus. In another exemplary embodiment, the virus is a member selected from picornaviridae, flaviviridae, coronaviridae, paramyxoviridae, orthomyxoviridae, retroviridae, herpesviridae and hepadnaviridae. In another exemplary embodiment, the virus is a member selected from a virus included in the following table:

TABLE A

| Viruses | |
|---|---|
| Virus Category | Pertinent Human Infections |
| RNA Viruses | |
| Picornaviridae | Polio |
| | Human hepatitis A |
| | Human rhinovirus |
| Togaviridae and Flaviviridae | Rubella - German measles |
| | Yellow fever |

TABLE A-continued

Viruses

| Virus Category | Pertinent Human Infections |
|---|---|
| Coronaviridae | Human respiratory coronavirus (HCV) |
| | Severe acute respiratory syndrome (SAR) |
| Rhabdoviridae | Lyssavirus - Rabies |
| Paramyxoviridae | Paramyxovirus - Mumps |
| | Morbillivirus - measles |
| | Pneumovirus - respiratory syncytial virus |
| Orthomyxoviridae | Influenza A-C |
| Bunyaviridae | Bunyavirus - Bunyamwera (BUN) |
| | Hantavirus - Hantaan (HTN) |
| | Nairevirus - Crimean-Congo hemorrhagic fever (CCHF) |
| | Phlebovirus - Sandfly fever (SFN) |
| | Uukuvirus - Uukuniemi (UUK) |
| | Rift Valley Fever (RVFN) |
| Arenaviridae | Junin - Argentine hemorrhagic fever |
| | Machupo - Bolivian hemorrhagic fever |
| | Lassa - Lassa fever |
| | LCM - aseptic lymphocyctic choriomeningitis |
| Reoviridae | Rotovirus |
| | Reovirus |
| | Orbivirus |
| Retroviridae | Human immunodeficiency virus 1 (HIV-1) |
| | Human immunodeficiency virus 2 (HIV-2) |
| | Simian immunodeficiency virus (SIV) |
| | DNA Viruses |
| Papovaviridae | Pediatric viruses that reside in kidney |
| Adenoviridae | Human respiratory distress and some deep-seated eye infections |
| Parvoviridae | Human gastro-intestinal distress (Norwalk Virus) |
| Herpesviridae | Herpes simplex virus 1 (HSV-1) |
| | Herpes simplex virus 2 (HSV-2) |
| | Human cytomegalovirus (HCMV) |
| | Varicella zoster virus (VZV) |
| | Epstein-Barr virus (EBV) |
| | Human herpes virus 6 (HHV6) |
| Poxviridae | Orthopoxvirus is sub-genus for smallpox |
| Hepadnaviridae | Hepatitis B virus (HBV) |
| | Hepatitis C virus (HCV) |

In another exemplary embodiment, the microorganism is a parasite. In an exemplary embodiment, the parasite is a member selected from *Plasmodium falciparum, P. vivax, P. ovale P. malariae, P. berghei, Leishmania donovani, L. infantum, L. chagasi, L. mexicana, L. amazonensis, L. venezuelensis, L. tropics, L. major, L. minor, L. aethiopica, L. Biana braziliensis, L. (V.) guyanensis, L. (V.) panamensis, L. (V.) peruviana, Trypanosoma brucei rhodesiense, T. brucei gambiense, T. cruzi, Giardia intestinalis, G. lambda, Toxoplasma gondii, Entamoeba histolytica, Trichomonas vaginalis, Pneumocystis carinii,* and *Cryptosporidium parvum.*

V. Methods of Treating or Preventing Infections

In another aspect, the invention provides a method of treating or preventing an infection, or both. The method includes administering to the animal a therapeutically effective amount of the compound of the invention, sufficient to treat or prevent said infection. In an exemplary embodiment, the compound of the invention is according to Formulae (I) or (II). In another exemplary embodiment, the animal is a member selected from human, cattle, deer, reindeer, goat, honey bee, pig, sheep, horse, cow, bull, dog, guinea pig, gerbil, rabbit, cat, camel, yak, elephant, ostrich, otter, chicken, duck, goose, guinea fowl, pigeon, swan, and turkey. In another exemplary embodiment, the animal is a human. In another exemplary embodiment, the animal is a member selected from a human, cattle, goat, pig, sheep, horse, cow, bull, dog, guinea pig, gerbil, rabbit, cat, chicken and turkey. In another exemplary embodiment, the infection is a member selected from a systemic infection, a cutaneous infection, and an ungual or periungual infection.

V. a) Methods of Treating of Preventing Ungual and/or Periungual Infections

In another aspect, the invention provides a method of treating or preventing an ungual and/or periungual infection. The method includes administering to the animal a therapeutically effective amount of the compound of the invention, sufficient to treat or prevent said infection. In another exemplary embodiment, the method includes administering the compound of the invention at a site which is a member selected from the skin, nail, hair, hoof, claw and the skin surrounding the nail, hair, hoof and claw.

V. a) 1) Onychomycosis

Onychomycosis is a disease of the nail caused by yeast, dermatophytes, or other molds, and represents approximately 50% of all nail disorders. Toenail infection accounts for approximately 80% of onychomycosis incidence, while fingernails are affected in about 20% of the cases. Dermatophytes are the most frequent cause of nail plate invasion, particularly in toenail onychomycosis. Onychomycosis caused by a dermatophyte is termed Tinea unguium. *Trichophyton rubrum* is by far the most frequently isolated dermatophyte, followed by *T. mentagrophytes*. Distal subungual onychomycosis is the most common presentation of tinea unguium, with the main site of entry through the hyponychium (the thickened epidermis underneath the free distal end of a nail) progressing in time to involve the nail bed and the nail plate. Discoloration, onycholysis, and accumulation of subungual debris and nail plate dystrophy characterize the disease. The disease adversely affects the quality of life of its victims, with subject complaints ranging from unsightly nails and discomfort with footwear, to more serious complications including secondary bacterial infections.

Many methods are known for the treatment of fungal infections, including the oral and topical use of antibiotics (e.g., nystatin and amphotericin B), imidazole anti-fungal agents such as miconazole, clotrimazole, fluconazole, econazole and sulconazole, and non-imidazole fungal agents such as the allylamine derivatives terbinafine and naftifine, and the benzylamine butenafine.

However, onychomycosis has proven to be resistant to most treatments. Nail fungal infections reside in an area difficult to access by conventional topical treatment and anti-fungal drugs cannot readily penetrate the nail plate to reach the infection sites under the nail. Therefore, onychomycosis has traditionally been treated by oral administration of anti-fungal drugs; however, clearly this is undesirable due to the potential for side effects of such drugs, in particular those caused by the more potent anti-fungal drugs such as itraconazole and ketoconazole. An alternative method of treatment of onychomycosis is by removal of the nail before treating with a topically active anti-fungal agent; such a method of treatment is equally undesirable. Systemic antimycotic agents require prolonged use and have the potential for significant side effects. Topical agents have usually been of little benefit, primarily because of poor penetration of the anti-fungal agents into and through the nail mass.

In an exemplary embodiment, the invention provides a method of treating or preventing onychomycosis. The method includes administering to the animal a therapeutically effective amount of a pharmaceutical formulation of the invention, sufficient to treat or prevent onychomycosis. In another exemplary embodiment, the method includes administering the pharmaceutical formulation of the invention at a site which is a member selected from the skin, nail, hair, hoof, claw and the skin surrounding the nail, hair, hoof and claw. In another exemplary embodiment, the pharmaceutical formulation includes a compound having a structure according to Formula (IIb). In another exemplary embodiment, $R^{1b}$ is H. In another exemplary embodiment, $R^{10b}$ and $R^{11b}$ are H. In another exemplary embodiment, one member selected from $R^{10b}$ and $R^{11b}$ is H and the other member selected from $R^{10b}$ and $R^{11b}$ is a member selected from halo, methyl, cyano, methoxy, hydroxymethyl and p-cyanophenyloxy. In another exemplary embodiment, $R^{10b}$ and $R^{11b}$ are members independently selected from fluoro, chloro, methyl, cyano, methoxy, hydroxymethyl, and p-cyanophenyl. In another exemplary embodiment, $R^{1b}$ is H; $R^{7b}$ is H; $R^{10b}$ is F and $R^{11b}$ are H. In another exemplary embodiment, $R^{11b}$ and $R^{12b}$, along with the atoms to which they are attached, are joined to form a phenyl group.

V. a) 2) Other Unugal and Periungual Infections

In an exemplary embodiment, the invention provides a method of treating or preventing an ungual or periungual infection in a mammal. This method comprising administering to the mammal a therapeutically effective amount of a compound of the invention, thereby treating or preventing the ungual or periungual infection. In an exemplary embodiment, the ungual or periungual infection is a member selected from: chloronychia, paronychias, erysipeloid, onychorrhexis, gonorrhea, swimming-pool granuloma, larva migrans, leprosy, Orf nodule, milkers' nodules, herpetic whitlow, acute bacterial perionyxis, chronic perionyxis, sporotrichosis, syphilis, tuberculosis verrucosa cutis, tularemia, tungiasis, peri- and subungual warts, zona, nail dystrophy (trachyonychia), and dermatological diseases with an effect on the nails, such as psoriasis, pustular psoriasis, alopecia aerata, parakeratosis pustulosa, contact dermatosis, Reiter's syndrome, psoriasiform acral dermatitis, lichen planus, idiopathy atrophy in the nails, lichin nitidus, lichen striatus, inflammatory linear verrucous epidermal naevus (ILVEN), alopecia, pemphigus, bullous pemphigoid, acquired epidermolysis bullosa, Darier's disease, pityriasis rubra pilaris, palmoplantar keratoderma, contact eczema, polymorphic erythema, scabies, Bazex syndrome, systemic scleroderma, systemic lupus erythematosus, chronic lupus erythematosus, dermatomyositus.

The compounds and pharmaceutical formulations of the invention useful for ungual and periungual applications also find application in the cosmetics field, in particular for the treatment of irregularities of the nails, koilonychias, Beau's lines, longitudinal ridging, ingrown nails.

In an exemplary embodiment, the infection is of the skin, nail, hair, claw or hoof, hair, ear and eye and is a member selected from Sporotrichosis, Mycotic keratitis, Extension oculomycosis, Endogenous oculomycosis, Lobomycosis, Mycetoma, Piedra, Pityriasis versicolor, Tinea corporis, Tinea cruris, Tinea pedis, Tinea barbae, Tinea capitis, Tinea nigra, Otomycosis, Tinea favosa, Chromomycosis, and Tinea Imbricata.

V. b) Methods of Treating Systemic Diseases

In another aspect, the invention provides a method of treating a systemic disease. The method involves contacting an animal with a compound of the invention. The method of delivery for treatment of systemic diseases can be oral, intravenous or transdermal.

In an exemplary embodiment, the infection is systemic and is a member selected from candidiasis, aspergillosis, coccidioidomycosis, cryptococcosis, histoplasmosis, blastomycosis, paracoccidioidomycosis, zygomycosis, phaeohyphomycosis and rhinosporidiosis.

V. c) Methods of Treating Diseases Involving Viruses

The compounds of the invention are useful for the treatment of diseases of both animals and humans, involving viruses. In an exemplary embodiment, the disease is a member selected from hepatitis A-B-C, yellow fever, respiratory syncytial, influenza, AIDS, herpes simplex, chicken pox, varicella zoster, and Epstein-Barr disease.

V. d) Methods of Treating Diseases Involving Parasites

The compounds of the invention are useful for the treatment of diseases of both animals and humans, involving parasites. In an exemplary embodiment, the disease is a member selected from malaria, Chagas' disease, Leishmaniasis, African sleeping sickness (African human trypanosomiasis), giardiasis, toxoplasmosis, amebiasis and cryptosporidiosis.

VI. Methods of Nail Penetration

It is believed that poor penetration of the active agent through the hoof or nail plate and/or excessive binding to keratin, (the major protein in nails and hair) are the reasons for the poor efficacy of 8% ciclopirox w/w in commercial lacquer and other topical treatments that have failed in clinical trials. In mild cases of onychomycosis, the pathogenic fungi reside in the nail plate only. In moderate to severe cases the pathogenic fungi establish a presence in the nail plate and in the nail bed. If the infection is cleared from the nail plate but not from the nail bed, the fungal pathogen can re-infect the nail plate. Therefore, to effectively treat onychomycosis, the infection must be eliminated from the nail plate and the nail bed. To do this, the active agent must penetrate and disseminate substantially throughout the nail plate and nail bed.

It is believed that in order for an active agent to be effective once disseminated throughout the infected area, it must be bioavailable to the fungal pathogen and cannot be so tightly and/or preferentially bound to keratin that the drug is rendered inactive.

An understanding of the morphology of the nail plate suggests certain physicochemical properties of an active agent that would facilitate penetration of the nail plate. The desired physicochemical properties are described throughout. The tested compounds of the present invention are able to penetrate the nail plate and were also active against *Trichophyton rubrum* and *mentagrophytes* and other species. In addition, the tested compounds are also active against *Trichophyton rubrum* in the presence of 5% keratin powder.

In another aspect, the invention provides a method of delivering a compound from the dorsal layer of the nail plate to the nail bed. This method comprises contacting the cell with a compound capable of penetrating the nail plate, under conditions sufficient to penetrate the nail. The compound has a molecular weight of between about 100 and about 200 Da. The compound also has a log P value of between about 1.0 and about 2.6. The compound additionally has a water solubility between about 0.1 mg/mL and 1 g/mL octanol/saturated water, thereby delivering said compound.

In a preferred embodiment, the physicochemical properties of the compound of the invention, described by quantities predictive for migration of the compound through the nail plate, including, but not limited to, molecular weight, log P and solubility in water, and the like, are effective to provide substantial penetration of the nail plate.

Compounds with a molecular weight of less than 200 Da penetrate the nail plate in a manner superior to the commercially available treatment for onychomycosis. In one embodiment of the present invention the compound has a molecular weight of between 130 and 200. In another embodiment of this invention, the compound has a molecular weight of from about 140 to about 200 Da. In another embodiment of this invention, the compound has a molecular weight of from about 170 to about 200 Da. In another embodiment of this invention, the compound has a molecular weight of from about 155 to about 190 Da. In another embodiment of this invention, the compound has a molecular weight of from about 165 to about 185 Da. In another embodiment of this invention, the compound has a molecular weight of from about 145 to about 170 Da. In yet another embodiment the molecular weight is either 151.93 or 168.39 Da.

In one embodiment of the present invention the compound has a Log P value of between about −3.5 to about 2.5. In another exemplary embodiment, the compound has a Log P value of from about −1.0 to about 2.5. In another exemplary embodiment, the compound has a Log P value of from about −1.0 to about 2.0. In another exemplary embodiment, the compound has a Log P value of from about −0.5 to about 2.5. In another exemplary embodiment, the compound has a Log P value of from about −0.5 to about 1.5. In another exemplary embodiment, the compound has a Log P value of from about 0.5 to about 2.5. In another exemplary embodiment, the compound has a Log P value of from about 1.0 to about 2.5. In yet another exemplary embodiment, the compound has a Log P value of 1.9 or 2.3.

Also contemplated by the present invention is a compound with a Log P value less then 2.5, with a molecular weight less than 200 Da, that are still able to penetrate the nail plate.

In one embodiment of the present invention the compound has a water solubility between about 0.1 mg/mL to 1 g/mL in octanol saturated water. In one embodiment of the present invention the compound has a water solubility of between 0.1 mg/mL and 100 mg/mL. In another embodiment of this invention, the compound has a water solubility of from about 0.1 mg/mL and 10 mg/mL. In another embodiment of this invention, the compound has a water solubility of from about 0.1 mg/mL and 1 mg/mL. In another embodiment of this invention, the compound has a water solubility of from about 5 mg/mL and 1 g/mL. In another embodiment of this invention, the compound has a water solubility of from about 10 mg/mL and 500 g/mL. In another embodiment of this invention, the compound has a water solubility of from about 80 mg/mL and 250 mg/mL.

In an exemplary embodiment, the present invention provides a compound with a Log P value selected from a range above, with a molecular weight selected from a range above, that are still able to penetrate the nail plate.

In an exemplary embodiment, the present invention provides compounds with a molecular weight selected from a range above, with a water solubility selected from a range above, that are still able to penetrate the nail plate.

In an exemplary embodiment, the present invention provides compounds with a log P selected from a range above, with a water solubility selected from a range above, that are still able to penetrate the nail plate.

In an exemplary embodiment, the present invention provides compounds with a molecular weight selected from a range above, with a log P selected from a range above, and with a water solubility selected from a range above, that are still able to penetrate the nail plate.

Penetration of the nail by the active ingredient may be effected by the polarity of the formulation. However, the polarity of the formulation is not expected have as much influence on nail penetration as some of the other factors, such as the molecular weight or the Log P of the active ingredient. The presence of penetration enhancing agents in the formulation is likely to increase penetration of the active agent when compared to similar formulations containing no penetration enhancing agent Some examples of molecules with optimal physicochemical properties are given in the table below.

| Structure: | (compound 1) | (compound 2) |
|---|---|---|
| Formula: | $C_7H_6BFO_2$ | $C_7H_6BClO_2$ |
| Molecular weight (Da): | 151.93 | 168.39 |
| Plasma protein binding (%) | 66 | 83 |
| LogP: | 1.9 | 2.3 |
| Water solubility (µg/mL): | >100 | >100 |

Compound 3 below is an example of a compound similar in molecular weight to ciclopirox, and like ciclopirox, penetrates the nail plate poorly.

| Structure: | (compound 3) |
|---|---|
| Formula: | $C_{13}H_{10}BFO$ |
| Molecular weight (Da): | 212.03 |
| Plasma protein binding (%): | 100 |
| cLogP: | 3.55 |
| Water solubility (µ/mL): | not determined |

In a preferred embodiment the topical formulations including a compound of Formulae (I) or (II) described structurally above has a total molecular weight of less than 200 Da, has a Log P of less than 2.5, and a minimum inhibitory concentration against *Trichophyton rubrum* that is substantially unchanged in the presence of 5% keratin.

This invention is still further directed to methods for treating a viral infection mediated at least in part by dermatophytes, *Trichophyton, Microsporum* or *Epidermophyton* species, or a yeast-like fungi including *Candida* species, in mammals, which methods comprise administering to a mammal, that has been diagnosed with said viral infection or is at risk of developing said viral infection, a pharmaceutical composition comprising a pharmaceutically acceptable diluent and a therapeutically effective amount of a compound described herein or mixtures of one or more of such compounds. In one embodiment the infection is onychomycosis.

Compounds contemplated by the present invention may have broad spectrum antifungal activity and as such may be candidates for use against other cutaneous fungal infections.

The methods provided in this aspect of the invention are useful in the penetration of nails and hoofs, as well as the treatment of ungual and periungual conditions.

VII. Pharmaceutical Formulations

In another aspect, the invention is a pharmaceutical formulation which includes: (a) a pharmaceutically acceptable excipient; and (b) a compound of the invention. In another aspect, the invention is a pharmaceutical formulation which includes: (a) a pharmaceutically acceptable excipient; and (b) a compound having a structure according to Formula (I), (Ia), (Ib), (Ic), or (Id). In another aspect, the invention is a pharmaceutical formulation which includes: (a) a pharmaceutically acceptable excipient; and (b) a compound which has a structure according to Formula (II), (IIa), (IIb), (IIc), (IId).

In another aspect, the invention is a pharmaceutical formulation comprising: (a) a pharmaceutically acceptable excipient; and (b) a compound having a structure according to Formula II:

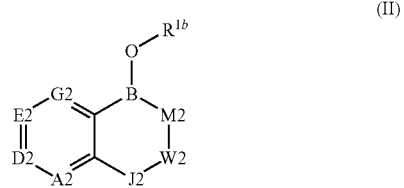

(II)

wherein B is boron. $R^{1b}$ is a member selected from a negative charge, a salt counterion, H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. M2 is a member selected from oxygen, sulfur and $NR^{2b}$. $R^{2b}$ is a member selected from H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. J2 is a member selected from $(CR^{3b}R^{4b})_{n2}$ and $CR^{5b}$. $R^{3b}$, $R^{4b}$, and $R^{5b}$ are members independently selected from H, OH, $NH_2$, SH, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. The index n2 is an integer selected from 0 to 2. W2 is a member selected from C=O (carbonyl), $(CR^{6b}R^{7b})_{m2}$ and $CR^{8b}$. $R^{6b}$, $R^{7b}$, and $R^{8b}$ are members independently selected from H, OH, $NH_2$, SH, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. The index m2 is an integer selected from 0 and 1. A2 is a member selected from $CR^{9b}$ and N. D2 is a member selected from $CR^{10b}$ and N. E2 is a member selected from $CR^{11b}$ and N. G2 is a member selected from $CR^{12b}$ and N. $R^{9b}$, $R^{10b}$, $R^{11b}$ and $R^{12b}$ are members independently selected from H, OH, $NH_2$, SH, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. The combination of nitrogens (A2+D2+E2+G2) is an integer selected from 0 to 3. A member selected from $R^{3b}$, $R^{4b}$ and $R^{5b}$ and a member selected from $R^{6b}$, $R^{7b}$ and $R^{8b}$, together with the atoms to which they are attached, are optionally joined to form a 4 to 7 membered ring. $R^{3b}$ and $R^{4b}$, together with the atoms to which they are attached, are optionally joined to form a 4 to 7 membered ring. $R^{6b}$ and $R^{7b}$, together with the atoms to which they are attached, are optionally joined to form a 4 to 7 membered ring. $R^{9b}$ and $R^{10b}$, together with the atoms to which they are attached, are optionally joined to form a 4 to 7 membered ring. $R^{10b}$ and $R^{11b}$, together with the atoms to which they are attached, are optionally joined to form a 4 to 7 membered ring. $R^{11b}$ and $R^{12b}$, together with the atoms to which they are attached, are optionally joined to form a 4 to 7 membered ring.

In an exemplary embodiment, the aspect has the proviso that when M2 is oxygen, W2 is a member selected from $(CR^{3b}R^{4b})_{n2}$, wherein n2 is 0, J2 is a member selected from $(CR^{6b}R^{7b})_{n2}$, wherein m2 is 1, A2 is $CR^{9b}$, D2 is $CR^{10b}$, E is $CR^{11b}$, G is $CR^{12b}$, then $R^{9b}$ is not a member selected from halogen, methyl, ethyl, or optionally joined with $R^{10b}$ to a form phenyl ring. In another exemplary embodiment, the aspect has the proviso that when M2 is oxygen, W2 is a member selected from $(CR^{3b}R^{4b})_n$, wherein n2 is 0, J2 is a member selected from $(CR^{6b}R^{7b})_m$, wherein m2 is 1, A2 is $CR^{9b}$, D2 is $CR^{10b}$, E2 is $CR^{11b}$, G2 is $CR^{12b}$, then $R^{10b}$ is not a member selected from unsubstituted phenoxy, $C(CH_3)_3$, halogen, $CF_3$, methoxy, ethoxy, or optionally joined with $R^{9b}$ to form a phenyl ring. In another exemplary embodiment, the aspect has the proviso that when M2 is oxygen, W2 is a member selected from $(CR^{3b}R^{4b})$, wherein n2 is 0, J2 is a member selected from $(CR^{6b}R^{7b})_{m2}$, wherein m2 is 1, A2 is $CR^{9b}$, D2 is $CR^{10b}$, E2 is $CR^{11b}$, G2 is $CR^{12b}$, then $R^{11b}$ is not a member selected from halogen or optionally joined with $R^{10b}$ to form a phenyl ring. In another exemplary embodiment, the aspect has the proviso that when M2 is oxygen, W2 is a member selected from $(CR^{3b}R^{4b})_{n2}$, wherein n2 is 0, J2 is a member selected from $(CR^{6b}R^{7b})$, wherein m2 is 1, A2 is $CR^{9b}$, D2 is $CR^{10b}$, E2 is $CR^{12b}$, G2 is $CR^{12b}$, then $R^{12b}$ is not halogen. In another exemplary embodiment, the aspect has the proviso that when M2 is oxygen, W2 is a member selected from $(CR^{3b}R^{4b})_{n2}$, wherein n2 is 0, J2 is a member selected from $(CR^{6b}R^{7b})_{m2}$, wherein m2 is 1, A2 is $CR^{9b}$, D2 is $CR^{10b}$, E2 is $CR^{11b}$, G2 is $CR^{12b}$, then $R^{6b}$ is not halophenyl. In another exemplary embodiment, the aspect has the proviso that when M2 is oxygen, W2 is a member selected from $(CR^{3b}R^{4b})_2$, wherein n2 is 0, J2 is a member selected from $(CR^{6b}R^{7b})_{m2}$, wherein m2 is 1, A2 is $CR^{9b}$, D2 is $CR^{10b}$, E2 is $CR^{11b}$, G2 is $CR^{12b}$, then $R^{7b}$ is not halophenyl. In another exemplary embodiment, the aspect has the proviso that when M2 is oxygen, W2 is a member selected from $(CR^{3b}R^{4b})_{n2}$, wherein n2 is 0, J2 is a member selected from $(CR^{6b}R^{7b})_m$, wherein m2 is 1, A2 is $CR^{9b}$, D2 is $CR^{11b}$, E2 is $CR^{12b}$, G2 is $CR^{12}$b, then $R^{6b}$ and $R^{7b}$ are not halophenyl. In another exemplary embodiment, the aspect has the proviso that when M2 is oxygen, W2 is a member selected from $(CR^{3b}R^{4b})_{n2}$, wherein n2 is 0, J2 is a member selected from $(CR^{6b}R^{7b})_{m2}$, wherein m2 is 1, A2 is $CR^{9b}$, D2 is $CR^{10b}$, E2 is $CR^{11b}$, G2 is $CR^{12b}$, and $R^{9b}$, $R^{10b}$ and $R^{11b}$ are H, then $R^{6b}$, $R^{7b}$ and $R^{12b}$ are not H. In another exemplary embodiment, the aspect has the proviso that when M2 is oxygen wherein n2 is 1, J2 is a member selected from $(CR^{6b}R^{7b})_{m2}$, wherein m2 is 0, A2 is $CR^{9b}$, D2 is $CR^{10b}$, E2 is $CR^{11b}$, G2 is $CR^{12b}$, $R^{9b}$ is H, $R^{10b}$ is H, $R^{11b}$ is H, $R^{6b}$ is H, $R^{7b}$ is H, $R^{12b}$ is H, then W2 is not C=O (carbonyl). In another exemplary embodiment, the aspect has the proviso that when M2 is oxygen, W2 is $CR^{5b}$, J2 is $CR^{8b}$, A2 is $CR^{9b}$, D2 is $CR^{10b}$, E2 is $CR^{11b}$, G2 is $CR^{12b}$, $R^{6b}$, $R^{7b}$, $R^{9b}$, $R^{10b}$, $R^{11b}$ and $R^{12b}$ are H, then $R^{5b}$ and $R^{8b}$, together with the atoms to which they are attached, do not form a phenyl ring.

In an exemplary embodiment, the pharmaceutical formulation has a compound with a structure according to Formula (IIa):

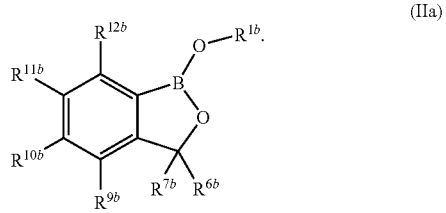

(IIa)

In another exemplary embodiment, the pharmaceutical formulation has a compound with a structure according to Formula (IIb):

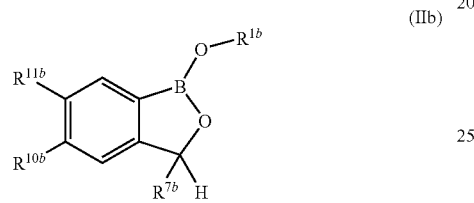

(IIb)

wherein $R^{7b}$ is a member selected from H, methyl, ethyl and phenyl. $R^{10b}$ is a member selected from H, OH, $NH_2$, SH, halogen, substituted or unsubstituted phenoxy, substituted or unsubstituted phenylalkyloxy, substituted or unsubstituted phenylthio and substituted or unsubstituted phenylalkylthio. $R^{11b}$ is a member selected from H, OH, $NH_2$, SH, methyl, substituted or unsubstituted phenoxy, substituted or unsubstituted phenylalkyloxy, substituted or unsubstituted phenylthio and substituted or unsubstituted phenylalkylthio.

In another exemplary embodiment, $R^{1b}$ is a member selected from a negative charge, H and a salt counterion. In another exemplary embodiment, $R^{10b}$ and $R^{11b}$ are H. In another exemplary embodiment, one member selected from $R^{10b}$ and $R^{11b}$ is H and the other member selected from $R^{10b}$ and $R^{11b}$ is a member selected from halo, methyl, cyano, methoxy, hydroxymethyl and p-cyanophenyloxy. In another exemplary embodiment, $R^{10b}$ and $R^{11b}$ are members independently selected from fluoro, chloro, methyl, cyano, methoxy, hydroxymethyl, and p-cyanophenyl. In another exemplary embodiment, $R^{1b}$ is a member selected from a negative charge, H and a salt counterion; $R^{7b}$ is H; $R^{10b}$ is F and $R^{11b}$ is H. In another exemplary embodiment, $R^{11b}$ and $R^{12b}$, along with the atoms to which they are attached, are joined to form a phenyl group. In another exemplary embodiment, $R^{1b}$ is a member selected from a negative charge, H and a salt counterion; $R^{7b}$ is H; $R^{10b}$ is 4-cyanophenoxy; and $R^{11b}$ is H.

In another exemplary embodiment, the pharmaceutical formulation has a compound with a structure according to Formula (IIc):

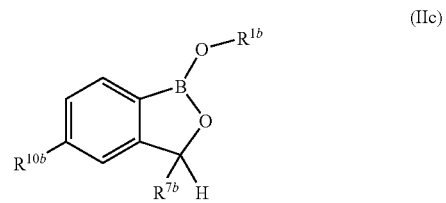

(IIc)

wherein $R^{10b}$ is a member selected from H, halogen, CN and substituted or unsubstituted $C_{1-4}$ alkyl. In another exemplary embodiment, the compound has a formulation which is a member selected from:

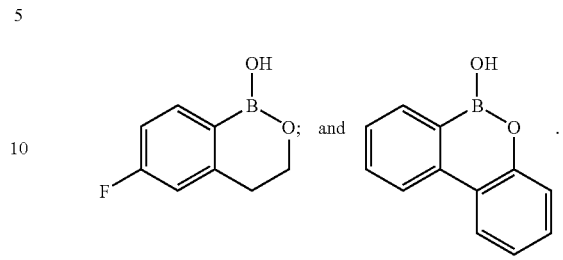

In another exemplary embodiment, the pharmaceutical formulation has a compound with a structure according to Formula (IId):

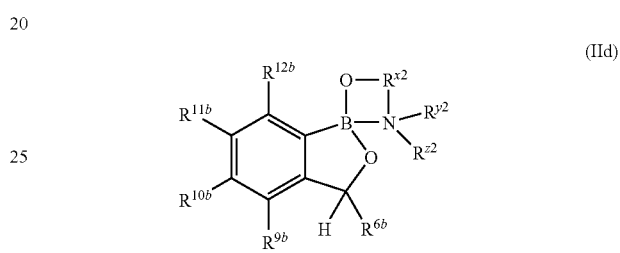

(IId)

wherein B is boron. $R^{x2}$ is a member selected from substituted or unsubstituted $C_1$-$C_5$ alkyl and substituted or unsubstituted $C_1$-$C_5$ heteroalkyl. $R^{y2}$ and $R^{y2}$ are members independently selected from H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

The pharmaceutical formulations of the invention can take a variety of forms adapted to the chosen route of administration. Those skilled in the art will recognize various synthetic methodologies that may be employed to prepare non-toxic pharmaceutical formulations incorporating the compounds described herein. Those skilled in the art will recognize a wide variety of non-toxic pharmaceutically acceptable solvents that may be used to prepare solvates of the compounds of the invention, such as water, ethanol, propylene glycol, mineral oil, vegetable oil and dimethylsulfoxide (DMSO).

The compositions of the invention may be administered orally, topically, parenterally, by inhalation or spray or rectally in dosage unit formulations containing conventional non-toxic pharmaceutically acceptable carriers, adjuvants and vehicles. It is further understood that the best method of administration may be a combination of methods. Oral administration in the form of a pill, capsule, elixir, syrup, lozenge, troche, or the like is particularly preferred. The term parenteral as used herein includes subcutaneous injections, intradermal, intravascular (e.g., intravenous), intramuscular, spinal, intrathecal injection or like injection or infusion techniques.

The pharmaceutical formulations containing compounds of the invention are preferably in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known in the art for the manufacture of pharmaceutical formulations, and such compositions may contain one or more agents selected from the group consisting of sweetening agents, flavoring agents, coloring agents and preserving agents in order to provide pharmaceutically elegant and palatable preparations. Tablets may contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; and dispersing or wetting agents, which may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical formulations of the invention may also be in the form of oil-in-water emulsions and water-in-oil emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth; naturally-occurring phosphatides, for example soy bean, lecithin, and esters or partial esters derived from fatty acids and hexitol; anhydrides, for example sorbitan monooleate; and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative, and flavoring and coloring agents. The pharmaceutical formulations may be in the form of a sterile injectable aqueous or oleaginous suspension. This suspension may be formulated according to the known art using those suitable dispersing or wetting agents and suspending agents, which have been mentioned above. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The composition of the invention may also be administered in the form of suppositories, e.g., for rectal administration of the drug. These compositions can be prepared by mixing the drug with a suitable non-irritating excipient that is solid at ordinary temperatures but liquid at the rectal temperature and will therefore melt in the rectum to release the drug. Such materials are cocoa butter and polyethylene glycols.

Alternatively, the compositions can be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

For administration to non-human animals, the composition containing the therapeutic compound may be added to the animal's feed or drinking water. Also, it will be convenient to formulate animal feed and drinking water products so that the animal takes in an appropriate quantity of the compound in its diet. It will further be convenient to present the compound in a composition as a premix for addition to the feed or drinking water. The composition can also added as a food or drink supplement for humans.

Dosage levels of the order of from about 5 mg to about 250 mg per kilogram of body weight per day and more preferably from about 25 mg to about 150 mg per kilogram of body weight per day, are useful in the treatment of the above-indicated conditions. The amount of active ingredient that may be combined with the carrier materials to produce a single dosage form will vary depending upon the condition being treated and the particular mode of administration. Dosage unit forms will generally contain between from about 1 mg to about 500 mg of an active ingredient.

Frequency of dosage may also vary depending on the compound used and the particular disease treated. However, for treatment of most disorders, a dosage regimen of 4 times daily or less is preferred. It will be understood, however, that the specific dose level for any particular patient will depend upon a variety of factors including the activity of the specific compound employed, the age, body weight, general health, sex, diet, time of administration, route of administration and rate of excretion, drug combination and the severity of the particular disease undergoing therapy.

Preferred compounds of the invention will have desirable pharmacological properties that include, but are not limited to, oral bioavailability, low toxicity, low serum protein binding and desirable in vitro and in vivo half-lives. Penetration of the blood brain barrier for compounds used to treat CNS disorders is necessary, while low brain levels of compounds used to treat peripheral disorders are often preferred.

Assays may be used to predict these desirable pharmacological properties. Assays used to predict bioavailability include transport across human intestinal cell monolayers, including Caco-2 cell monolayers. Toxicity to cultured hepatocyctes may be used to predict compound toxicity. Penetration of the blood brain barrier of a compound in humans may be predicted from the brain levels of laboratory animals that receive the compound intravenously.

Serum protein binding may be predicted from albumin binding assays. Such assays are described in a review by Oravcova, et al. (Journal of Chromatography B (1996) volume 677, pages 1-27).

Compound half-life is inversely proportional to the frequency of dosage of a compound. In vitro half-lives of compounds may be predicted from assays of microsomal half-life as described by Kuhnz and Gieschen (Drug Metabolism and Disposition, (1998) volume 26, pages 1120-1127).

The amount of the composition required for use in treatment will vary not only with the particular compound selected but also with the route of administration, the nature of the condition being treated and the age and condition of the patient and will ultimately be at the discretion of the attendant physician or clinician.

VII. a) Topical Formulations

In a preferred embodiment, the methods of the invention can be used employed through the topical application of the compounds described herein.

The compositions of the present invention comprises fluid or semi-solid vehicles that may include but are not limited to polymers, thickeners, buffers, neutralizers, chelating agents, preservatives, surfactants or emulsifiers, antioxidants, waxes or oils, emollients, sunscreens, and a solvent or mixed solvent system. The solvent or mixed solvent system is important to the formation because it is primarily responsible for dissolving the drug. The best solvent or mixed solvent systems are also capable of maintaining clinically relevant levels of the drug in solution despite the addition of a poor solvent to the formulation. The topical compositions useful in the subject invention can be made into a wide variety of product types. These include, but are not limited to, lotions, creams, gels, sticks, sprays, ointments, pastes, foams, mousses, and cleansers. These product types can comprise several types of carrier systems including, but not limited to particles, nanoparticles, and liposomes. If desired, disintegrating agents can be added, such as the cross-linked polyvinyl pyrrolidone, agar or alginic acid or a salt thereof such as sodium alginate. Techniques for formulation and administration can be found in *Remington: The Science and Practice of Pharmacy*, supra. The formulation can be selected to maximize delivery to a desired target site in the body.

Lotions, which are preparations that are to be applied to the skin, nail, hair, claw or hoof surface without friction, are typically liquid or semi-liquid preparations in which finely divided solid, waxy, or liquid are dispersed. Lotions will typically contain suspending agents to produce better dispersions as well as compounds useful for localizing and holding the active agent in contact with the skin, nail, hair, claw or hoof, e.g., methylcellulose, sodium carboxymethyl-cellulose, or the like.

Creams containing the active agent for delivery according to the present invention are viscous liquid or semisolid emulsions, either oil-in-water or water-in-oil. Cream bases are water-washable, and contain an oil phase, an emulsifier and an aqueous phase. The oil phase is generally comprised of petrolatum or a fatty alcohol, such as cetyl- or stearyl alcohol; the aqueous phase usually, although not necessarily, exceeds the oil phase in volume, and generally contains a humectant. The emulsifier in a cream formulation, as explained in *Remington: The Science and Practice of Pharmacy*, supra, is generally a nonionic, anionic, cationic or amphoteric surfactant.

Gel formulations can also be used in connection with the present invention. As will be appreciated by those working in the field of topical drug formulation, gels are semisolid. Single-phase gels contain organic macromolecules distributed substantially uniformly throughout the carrier liquid, which is typically aqueous, but also may be a solvent or solvent blend.

Ointments, which are semisolid preparations, are typically based on petrolatum or other petroleum derivatives. As will be appreciated by the ordinarily skilled artisan, the specific ointment base to be used is one that provides for optimum delivery for the active agent chosen for a given formulation, and, preferably, provides for other desired characteristics as well, e.g., emolliency or the like. As with other carriers or vehicles, an ointment base should be inert, stable, nonirritating and non-sensitizing. As explained in Remington: The Science and Practice of Pharmacy, 19th Ed. (Easton, Pa.: Mack Publishing Co., 1995), at pages 1399-1404, ointment bases may be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin and hydrophilic petrolatum. Emulsion ointment bases are either water-in-oil (W/O) emulsions or oil-in-water (O/W) emulsions, and include, for example, cetyl alcohol, glyceryl monostearate, lanolin and stearic acid. Preferred water-soluble ointment bases are prepared from polyethylene glycols of varying molecular weight; again, reference may be had to Remington: The Science and Practice of Pharmacy, supra, for further information.

Useful formulations of the invention also encompass sprays. Sprays generally provide the active agent in an aqueous and/or alcoholic solution which can be misted onto the skin, nail, hair, claw or hoof for delivery. Such sprays include those formulated to provide for concentration of the active agent solution at the site of administration following delivery, e.g., the spray solution can be primarily composed of alcohol or other like volatile liquid in which the drug or active agent can be dissolved. Upon delivery to the skin, nail, hair, claw or hoof, the carrier evaporates, leaving concentrated active agent at the site of administration.

The topical pharmaceutical compositions may also comprise suitable solid or gel phase carriers. Examples of such carriers include but are not limited to calcium carbonate, calcium phosphate, various sugars, starches, cellulose derivatives, gelatin, and polymers such as polyethylene glycols.

The topical pharmaceutical compositions may also comprise a suitable emulsifier which refers to an agent that enhances or facilitates mixing and suspending oil-in-water or water-in-oil. The emulsifying agent used herein may consist of a single emulsifying agent or may be a nonionic, anionic, cationic or amphoteric surfactant or blend of two or more such surfactants; preferred for use herein are nonionic or anionic emulsifiers. Such surface-active agents are described in "McCutcheon's Detergent and Emulsifiers," North American Edition, 1980 Annual published by the McCutcheon Division, MC Publishing Company, 175 Rock Road, Glen Rock, N.J. 07452, USA.

Preferred for use herein are high molecular weight alcohols such as cetearyl alcohol, cetyl alcohol, stearyl alcohol, emulsifying wax, glyceryl monostearate. Other examples are ethylene glycol distearate, sorbitan tristearate, propylene glycol monostearate, sorbitan monooleate, sorbitan monostearate (SPAN 60), diethylene glycol monolaurate, sorbitan monopalmitate, sucrose dioleate, sucrose stearate (CRODESTA F-160), polyoxyethylene lauryl ether (BRIJ 30), polyoxyethylene (2) stearyl ether (BRIJ 72), polyoxyethylene (21) stearyl ether (BRIJ 721), polyoxyethylene monostearate (Myrj 45), polyoxyethylene sorbitan monostearate (TWEEN 60), polyoxyethylene sorbitan monooleate (TWEEN 80), polyoxyethylene sorbitan monolaurate (TWEEN 20) and sodium oleate. Cholesterol and cholesterol derivatives may also be employed in externally used emulsions and promote w/o emulsions.

Especially suitable nonionic emulsifying agents are those with hydrophile-lipophile balances (HLB) of about 3 to 6 for w/o system and 8 to 18 for o/w system as determined by the method described by Paul L. Lindner in "Emulsions and Emulsion", edited by Kenneth Lissant, published by Dekker, New York, N.Y., 1974, pages 188-190. More preferred for use herein are one or more nonionic surfactants that produce a system having HLB of about 8 to about 18.

Examples of such nonionic emulsifiers include but are not limited to "BRIJ 72", the trade name for a polyoxyethylene (2) stearyl ether having an HLB of 4.9; "BRIJ 721", the trade name for a polyoxyethylene (21) stearyl ether having an HLB of 15.5, "Brij 30", the trade name for polyoxyethylene lauryl ether having an HLB of 9.7; "Polawax", the trade name for emulsifying wax having an HLB of 8.0; "Span 60", the trade name for sorbitan monostearate having an HLB of 4.7; "Crodesta F-160", the trade name for sucrose stearate" having an HLB of 14.5. All of these materials are available from Ruger Chemicals Inc.; Croda; ICI Americas, Inc.; Spectrum Chemicals; and BASF. When the topical formulations of the present invention contain at least one emulsifying agent, each emulsifying agent is present in amount from about 0.5 to about 2.5 wt %, preferably 0.5 to 2.0%, more preferably 1.0% or 1.8%. Preferably the emulsifying agent comprises a mixture of steareth 21 (at about 1.8%) and steareth 2 (at about 1.0%).

The topical pharmaceutical compositions may also comprise suitable emollients. Emollients are materials used for the prevention or relief of dryness, as well as for the protection of the skin, nail, hair, claw or hoof. Useful emollients include, but are not limited to, cetyl alcohol, isopropyl myristate, stearyl alcohol, and the like. A wide variety of suitable emollients are known and can be used herein. See e.g., Sagarin, Cosmetics, Science and Technology, 2nd Edition, Vol. 1, pp. 32-43 (1972), and U.S. Pat. No. 4,919,934, to Deckner et al., issued Apr. 24, 1990, both of which are incorporated herein by reference in their entirety. These materials are available from Ruger Chemical Co, (Irvington, N.J.).

When the topical formulations of the present invention contain at least one emollient, each emollient is present in an amount from about 0.1 to 15%, preferably 0.1 to about 3.0, more preferably 0.5, 1.0, or 2.5 wt %. Preferably the emollient is a mixture of cetyl alcohol, isopropyl myristate and stearyl alcohol in a 1/5/2 ratio. The emollient may also be a mixture of cetyl alcohol and stearyl alcohol in a 1/2 ratio.

The topical pharmaceutical compositions may also comprise suitable antioxidants, substances known to inhibit oxidation. Antioxidants suitable for use in accordance with the present invention include, but are not limited to, butylated hydroxytoluene, ascorbic acid, sodium ascorbate, calcium ascorbate, ascorbic palmitate, butylated hydroxyanisole, 2,4, 5-trihydroxybutyrophenone, 4-hydroxymethyl-2,6-di-tert-butylphenol, erythorbic acid, gum guaiac, propyl gallate, thiodipropionic acid, dilauryl thiodipropionate, tert-butylhydroquinone and tocopherols such as vitamin E, and the like, including pharmaceutically acceptable salts and esters of these compounds. Preferably, the antioxidant is butylated hydroxytoluene, butylated hydroxyanisole, propyl gallate, ascorbic acid, pharmaceutically acceptable salts or esters thereof, or mixtures thereof. Most preferably, the antioxidant is butylated hydroxytoluene. These materials are available from Ruger Chemical Co, (Irvington, N.J.).

When the topical formulations of the present invention contain at least one antioxidant, the total amount of antioxidant present is from about 0.001 to 0.5 wt %, preferably 0.05 to about 0.5 wt %, more preferably 0.1%.

The topical pharmaceutical compositions may also comprise suitable preservatives. Preservatives are compounds added to a pharmaceutical formulation to act as an antimicrobial agent. Among preservatives known in the art as being effective and acceptable in parenteral formulations are benzalkonium chloride, benzethonium, chlorohexidine, phenol, m-cresol, benzyl alcohol, methylparaben, propylparaben, chlorobutanol, o-cresol, p-cresol, chlorocresol, phenylmercuric nitrate, thimerosal, benzoic acid, and various mixtures thereof. See, e.g., Wallhausser, K.-H., Develop. Biol. Standard, 24:9-28 (1974) (S. Krager, Basel). Preferably, the preservative is selected from methylparaben, propylparaben and mixtures thereof. These materials are available from Inolex Chemical Co (Philadelphia, Pa.) or Spectrum Chemicals.

When the topical formulations of the present invention contain at least one preservative, the total amount of preservative present is from about 0.01 to about 0.5 wt %, preferably from about 0.1 to 0.5%, more preferably from about 0.03 to about 0.15. Preferably the preservative is a mixture of methylparaben and proplybarben in a 5/1 ratio. When alcohol is used as a preservative, the amount is usually 15 to 20%.

The topical pharmaceutical compositions may also comprise suitable chelating agents to form complexes with metal cations that do not cross a lipid bilayer. Examples of suitable chelating agents include ethylene diamine tetraacetic acid (EDTA), ethylene glycol-bis(beta-aminoethyl ether)-N,N,N', N'-tetraacetic acid (EGTA) and 8-Amino-2-[(2-amino-5-methylphenoxy)methyl]-6-methoxyquinoline-N,N,N',N'-tetraacetic acid, tetrapotassium salt (QUIN-2). Preferably the chelating agents are EDTA and citric acid. These materials are available from Spectrum Chemicals.

When the topical formulations of the present invention contain at least one chelating agent, the total amount of chelating agent present is from about 0.005% to 2.0% by weight, preferably from about 0.05% to about 0.5 wt %, more preferably about 0.1% by weight.

The topical pharmaceutical compositions may also comprise suitable neutralizing agents used to adjust the pH of the formulation to within a pharmaceutically acceptable range. Examples of neutralizing agents include but are not limited to trolamine, tromethamine, sodium hydroxide, hydrochloric acid, citric acid, and acetic acid. Such materials are available from are available from Spectrum Chemicals (Gardena, Calif.).

When the topical formulations of the present invention contain at least one neutralizing agent, the total amount of neutralizing agent present is from about 0.1 wt to about 10 wt %, preferably 0.1 wt % to about 5.0 wt %, and more preferably about 1.0 wt %. The neutralizing agent is generally added in whatever amount is required to bring the formulation to the desired pH.

The topical pharmaceutical compositions may also comprise suitable viscosity increasing agents. These components are diffusible compounds capable of increasing the viscosity of a polymer-containing solution through the interaction of the agent with the polymer. CARBOPOL ULTREZ 10 may be used as a viscosity-increasing agent. These materials are available from Noveon Chemicals, Cleveland, Ohio.

When the topical formulations of the present invention contain at least one viscosity increasing agent, the total amount of viscosity increasing agent present is from about 0.25% to about 5.0% by weight, preferably from about 0.25% to about 1.0 wt %, and more preferably from about 0.4% to about 0.6% by weight.

The topical pharmaceutical compositions may also comprise suitable nail penetration enhancers. Examples of nail penetration enhancers include mercaptan compounds, sulfites and bisulfites, keratolytic agents and surfactants. Nail penetration enhancers suitable for use in the invention are described in greater detail in Malhotra et al., *J. Pharm. Sci.*, 91:2, 312-323 (2002), which is incorporated herein by reference in its entirety.

The topical pharmaceutical compositions may also comprise one or more suitable solvents. The ability of any solid substance (solute) to dissolve in any liquid substance (solvent) is dependent upon the physical properties of the solute and the solvent. When solutes and solvents have similar physical properties the solubility of the solute in the solvent will be the greatest. This gives rise to the traditional understanding that "like dissolves like." Solvents can be characterized in one extreme as non-polar, lipophilic oils, while in the other extreme as polar hydrophilic solvents. Oily solvents dissolve other non-polar substances by Van der Wals interactions while water and other hydrophilic solvents dissolve polar substances by ionic, dipole, or hydrogen bonding interactions. All solvents can be listed along a continuum from the least polar, i.e. hydrocarbons such as decane, to the most polar solvent being water. A solute will have its greatest solubility in solvents having equivalent polarity. Thus, for drugs having minimal solubility in water, less polar solvents will provide improved solubility with the solvent having polarity nearly equivalent to the solute providing maximum solubility. Most drugs have intermediate polarity, and thus experience maximum solubility in solvents such as propylene glycol or ethanol, which are significantly less polar than water. If the drug has greater solubility in propylene glycol (for example 8% (w/w)) than in water (for example 0.1% (w/w)), then addition of water to propylene glycol should decrease the maximum amount of drug solubility for the solvent mixture compared with pure propylene glycol. Addition of a poor solvent to an excellent solvent will decrease the maximum solubility for the blend compared with the maximum solubility in the excellent solvent.

When compounds are incorporated into topical formulations the concentration of active ingredient in the formulation may be limited by the solubility of the active ingredient in the chosen solvent and/or carrier. Non-lipophilic drugs typically display very low solubility in pharmaceutically acceptable solvents and/or carriers. For example, the solubility of some compounds in the invention in water is less than 0.00025% wt/wt. The solubility of the same compounds in the invention can be less than about 2% wt/wt in either propylene glycol or isopropyl myristate. In one embodiment of the present invention, diethylene glycol monoethyl ether (DGME) is the solvent used to dissolve the compounds of Formula (I) of Formula (II). The compounds in the invention useful in the present formulation are believed to have a solubility of from about 10% wt/wt to about 25% wt/wt in DGME. In another embodiment a DGME water cosolvent system is used to dissolve the compounds of Formula (I) of Formula (II). The solvent capacity of DGME drops when water is added; however, the DGME/water cosolvent system can be designed to maintain the desired concentration of from about 0.1% to about 5% wt/wt active ingredient. Preferably the active ingredient is present from about 0.5% to about 3% wt/wt, and more preferably at about 1% wt/wt, in the as-applied topical formulations. Because DGME is less volatile than water, as the topical formulation evaporates upon application, the active agent becomes more soluble in the cream formulation. This increased solubility reduces the likelihood of reduced bioavailability caused by the drug precipitating on the surface of the skin, nail, hair, claw or hoof.

Liquid forms, such as lotions suitable for topical administration or suitable for cosmetic application, may include a suitable aqueous or nonaqueous vehicle with buffers, suspending and dispensing agents, thickeners, penetration enhancers, and the like. Solid forms such as creams or pastes or the like may include, for example, any of the following ingredients, water, oil, alcohol or grease as a substrate with surfactant, polymers such as polyethylene glycol, thickeners, solids and the like. Liquid or solid formulations may include enhanced delivery technologies such as liposomes, microsomes, microsponges and the like.

Additionally, the compounds can be delivered using a sustained-release system, such as semipermeable matrices of solid hydrophobic polymers containing the therapeutic agent. Various sustained-release materials have been established and are well known by those skilled in the art.

Topical treatment regimens according to the practice of this invention comprise applying the composition directly to the skin, nail, hair, claw or hoof at the application site, from one to several times daily.

Formulations of the present invention can be used to treat, ameliorate or prevent conditions or symptoms associated with bacterial infections, acne, inflammation and the like.

In an exemplary embodiment, the pharmaceutical formulation includes a simple solution. In an exemplary embodiment, the simple solution includes an alcohol. In an exemplary embodiment, the simple solution includes alcohol and water. In an exemplary embodiment, the alcohol is ethanol, ethylene glycol, propanol, polypropylene glycol, isopropanol or butanol. In another exemplary embodiment, the simple solution is a member selected from about 10% polypropylene glycol and about 90% ethanol; about 20% polypropylene glycol and about 80% ethanol; about 30% polypropylene glycol and about 70% ethanol; about 40% polypropylene glycol and about 60% ethanol; about 50% polypropylene glycol and about 50% ethanol; about 60% polypropylene glycol and about 40% ethanol; about 70% polypropylene glycol and about 30% ethanol; about 80% polypropylene glycol and about 20% ethanol; about 90% polypropylene glycol and about 10% ethanol.

In an exemplary embodiment, the pharmaceutical formulation is a lacquer. Please see Remington's, supra, for more information on the production of lacquers.

In an exemplary embodiment, the compound is present in said pharmaceutical formulation in a concentration of from about 0.5% to about 15%. In an exemplary embodiment, the compound is present in said pharmaceutical formulation in a concentration of from about 0.1% to about 12.5%. In an exemplary embodiment, the compound is present in said pharmaceutical formulation in a concentration of from about 1% to about 10%. In an exemplary embodiment, the compound is present in said pharmaceutical formulation in a concentration of from about 1% to about 5%. In an exemplary embodiment, the compound is present in said pharmaceutical formulation in a concentration of from about 2% to about 8%. In an exemplary embodiment, the compound is present in said pharmaceutical formulation in a concentration of from about 4% to about 9%.

VII. b) Additional Active Agents

The following are examples of the cosmetic and pharmaceutical agents that can be added to the topical pharmaceutical formulations of the present invention. The following agents are known compounds and are readily available commercially.

Anti-inflammatory agents include, but are not limited to, bisabolol, mentholatum, dapsone, aloe, hydrocortisone, and the like.

Vitamins include, but are not limited to, Vitamin B, Vitamin E, Vitamin A, Vitamin D, and the like and vitamin derivatives such as tazarotene, calcipotriene, tretinoin, adapalene and the like.

Anti-aging agents include, but are not limited to, niacinamide, retinol and retinoid derivatives, AHA, Ascorbic acid, lipoic acid, coenzyme Q 10, beta hydroxy acids, salicylic acid, copper binding peptides, dimethylaminoethyl (DAEA), and the like.

Sunscreens and or sunburn relief agents include, but are not limited to, PABA, jojoba, aloe, padimate-O, methoxycinnamates, proxamine HCl, lidocaine and the like. Sunless tanning agents include, but are not limited to, dihydroxyacetone (DHA).

Psoriasis-treating agents and/or acne-treating agents include, but are not limited to, salicylic acid, benzoyl peroxide, coal tar, selenium sulfide, zinc oxide, pyrithione (zinc and/or sodium), tazarotene, calcipotriene, tretinoin, adapalene and the like.

Agents that are effective to control or modify keratinization, including without limitation: tretinoin, tazarotene, and adapalene.

The compositions comprising an compound/active agent of Formula (I) of Formula (II), and optionally at least one of these additional agents, are to be administered topically. In a primary application, this leads to the compounds of the invention and any other active agent working upon and treating the skin, nail, hair, claw or hoof. Alternatively, any one of the topically applied active agents may also be delivered systemically by transdermal routes.

In such compositions an additional cosmetically or pharmaceutically effective agent, such as an anti-inflammatory agent, vitamin, anti-aging agent, sunscreen, and/or acne-treating agent, for example, is usually a minor component (from about 0.001% to about 20% by weight or preferably from about 0.01% to about 10% by weight) with the remainder being various vehicles or carriers and processing aids helpful for forming the desired dosing form.

VII. c) Testing

Preferred compounds for use in the present topical formulations will have certain pharmacological properties. Such properties include, but are not limited to, low toxicity, low serum protein binding and desirable in vitro and in vivo half-lives. Assays may be used to predict these desirable pharmacological properties. Assays used to predict bioavailability include transport across human intestinal cell monolayers, including Caco-2 cell monolayers. Serum protein binding may be predicted from albumin binding assays. Such assays are described in a review by Oravcova et al. (1996, *J. Chromat. B*677: 1-27). Compound half-life is inversely proportional to the frequency of dosage of a compound. In vitro half-lives of compounds may be predicted from assays of microsomal half-life as described by Kuhnz and Gleschen (Drug Metabolism and Disposition, (1998) volume 26, pages 1120-1127).

Toxicity and therapeutic efficacy of such compounds can be determined by standard pharmaceutical procedures in cell cultures or experimental animals, e.g., for determining the LD50 (the dose lethal to 50% of the population) and the $ED_{50}$ (the dose therapeutically effective in 50% of the population). The dose ratio between toxic and therapeutic effects is the therapeutic index and it can be expressed as the ratio between $LD_{50}$ and $ED_{50}$. Compounds that exhibit high therapeutic indices are preferred. The data obtained from these cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the dosage form employed and the route of administration utilized. The exact formulation, route of administration and dosage can be chosen by the individual physician in view of the patient's condition. (See, e.g. Fingl et al., 1975, in "The Pharmacological Basis of Therapeutics", Ch. 1, p. 1).

VII. d) Administration

For any compound used in the method of the invention, the therapeutically effective dose can be estimated initially from cell culture assays, as disclosed herein. For example, a dose can be formulated in animal models to achieve a circulating concentration range that includes the $EC_{50}$ (effective dose for 50% increase) as determined in cell culture, i.e., the concentration of the test compound which achieves a half-maximal inhibition of bacterial cell growth. Such information can be used to more accurately determine useful doses in humans.

In general, the compounds prepared by the methods, and from the intermediates, described herein will be administered in a therapeutically or cosmetically effective amount by any of the accepted modes of administration for agents that serve similar utilities. It will be understood, however, that the specific dose level for any particular patient will depend upon a variety of factors including the activity of the specific compound employed, the age, body weight, general health, sex, diet, time of administration, route of administration, and rate of excretion, drug combination, the severity of the particular disease undergoing therapy and the judgment of the prescribing physician. The drug can be administered from once or twice a day, or up to 3 or 4 times a day.

Dosage amount and interval can be adjusted individually to provide plasma levels of the active moiety that are sufficient to maintain bacterial cell growth inhibitory effects. Usual patient dosages for systemic administration range from 0.1 to 1000 mg/day, preferably, 1-500 mg/day, more preferably 10-200 mg/day, even more preferably 100-200 mg/day. Stated in terms of patient body surface areas, usual dosages range from 50-91 mg/m$^2$/day.

The amount of the compound in a formulation can vary within the full range employed by those skilled in the art. Typically, the formulation will contain, on a weight percent (wt %) basis, from about 0.01-10 wt % of the drug based on the total formulation, with the balance being one or more suitable pharmaceutical excipients. Preferably, the compound is present at a level of about 0.1-3.0 wt %, more preferably, about 1.0 wt %.

The invention is further illustrated by the Examples that follow. The Examples are not intended to define or limit the scope of the invention.

EXAMPLES

Proton NMR are recorded on Varian AS 300 spectrometer and chemical shifts are reported as δ (ppm) down field from tetramethylsilane. Mass spectra are determined on Micromass Quattro II.

Example 1

Preparation of 3 from 1

1.1 Reduction of Carboxylic Acid

To a solution of 1 (23.3 mmol) in anhydrous THF (70 mL) under nitrogen was added dropwise a $BH_3$ THF solution (1.0 M, 55 mL, 55 mmol) at 0° C. and the reaction mixture was stirred overnight at room temperature. Then the mixture was cooled again with ice bath and MeOH (20 mL) was added dropwise to decompose excess $BH_3$. The resulting mixture was stirred until no bubble was released and then 10% NaOH (10 mL) was added. The mixture was concentrated and the residue was mixed with water (200 mL) and extracted with EtOAc. The residue from rotary evaporation was purified by flash column chromatography over silica gel to give 20.7 mmol of 3.

1.2 Results

Exemplary compounds of structure 3 prepared by the method above are provided below.

1.2.a 2-Bromo-5-chlorobenzyl Alcohol $^1$H NMR (300 MHz, DMSO-$d_6$): δ 7.57 (d, J=8.7 Hz, 1H), 7.50-7.49 (m, 1H), 7.28-7.24 (m, 1H), 5.59 (t, J=6.0 Hz, 1H) and 4.46 (d, J=6.0 Hz, 2H) ppm.

1.2.b 2-Bromo-5-methoxybenzyl Alcohol $^1$H NMR (300 MHz, DMSO-$d_6$): δ 7.42 (d, J=8.7 Hz, 1H), 7.09 (d, J=2.4 Hz, 1H), 6.77 (dd, $J_1$=3 Hz, $J_2$=3 Hz, 1H), 5.43 (t, J=5.7 Hz, 1H), 4.44 (d, J=5.1 Hz, 2H), 3.76 (s, 3H).

Example 2

Preparation of 3 from 2

2.1. Reduction of Aldehyde

To a solution of 2 (Z=H, 10.7 mmol) in methanol (30 mL) was added sodium borohydride (5.40 mol), and the mixture was stirred at room temperature for 1 h. Water was added, and the mixture was extracted with ethyl acetate. The organic layer was washed with brine and dried on anhydrous sodium sulfate. The solvent was removed under reduced pressure to afford 9.9 mmol of 3.

2.2 Results

Exemplary compounds of structure 3 prepared by the method above are provided below.

2.2.a 2-Bromo-5-(4-cyanophenoxy)benzyl Alcohol $^1$H-NMR (300 MHz, CDCl$_3$) δ (ppm) 2.00 (br s, 1H), 4.75 (s, 2H), 6.88 (dd, J=8.5, 2.9 Hz, 1H), 7.02 (d, J=8.8 Hz, 1H), 7.26 (d, J=2.6 Hz, 1H), 7.56 (d, J=8.5 Hz, 1H), 7.62 (d, J=8.8 Hz, 2H).

2.2.b 2-Bromo-4-(4-cyanophenoxy)benzyl Alcohol $^1$H NMR (300 MHz, DMSO-$d_6$): δ 7.83 (d, 2H), 7.58 (d, 1H), 7.39 (d, 1H), 7.18 (dd, 1H), 7.11 (d, 2H), 5.48 (t, 1H) and 4.50 (d, 2H) ppm.

2.2.c 5-(4-Cyanophenoxy)-1-Indanol

M.p. 50-53° C. MS (ESI+): m/z=252 (M+1). HPLC: 99.7% purity at 254 nm and 99.0% at 220 nm. $^1$H NMR (300 MHz, DMSO-$d_6$): δ 7.80 (d, 2H), 7.37 (d, 1H), 7.04 (d, 2H), 6.98-6.93 (m, 2H), 5.27 (d, 1H), 5.03 (q, 1H), 2.95-2.85 (m, 1H), 2.75-2.64 (m, 1H), 2.39-2.29 (m, 1H) and 1.85-1.74 (m, 1H) ppm.

2.2.d 2-Bromo-5-(tert-butyldimethylsiloxy)benzyl Alcohol $^1$H-NMR (300 MHz, CDCl$_3$) δ (ppm) 0.20 (s, 6H), 0.98 (s, 9H), 4.67 (br s, 1H), 6.65 (dd, J=8.2, 2.6 Hz, 1H), 6.98 (d, J=2.9 Hz, 1H), 7.36 (d, J=8.8 Hz, 1H).

Additional examples of compounds which can be produced by this method include 2-bromo-4-(3-cyanophenoxy) benzyl alcohol; 2-bromo-4-(4-chlorophenoxy)benzyl alcohol; 2-bromo-4-phenoxybenzyl alcohol; 2-bromo-5-(3,4-dicyanophenoxy)benzyl alcohol; 2-(2-bromo-5-fluorophenyl)ethyl alcohol; 2-bromo-5-fluorobenzyl alcohol; and 1-bromo-2-naphthalenemethanol.

Example 3

Preparation of 4 from 3

3.1 Protective Alkylation

Compound 3 (20.7 mmol) was dissolved in $CH_2Cl_2$ (150 mL) and cooled to 0° C. with ice bath. To this solution under nitrogen were added in sequence N,N-di-isopropyl ethyl amine (5.4 mL, 31.02 mmol, 1.5 eq) and chloromethyl methyl ether (2 mL, 25.85 mmol, 1.25 eq). The reaction mixture was stirred overnight at room temperature and washed with NaHCO$_3$-saturated water and then NaCl-saturated water. The residue after rotary evaporation was purified by flash column chromatography over silica gel to give 17.6 mmol of 4.

3.2 Results

Exemplary compounds of structure 4 prepared by the method above are provided below.

3.2.a 2-Bromo-5-chloro-1-(methoxymethoxymethyl)benzene $^1$H NMR (300 MHz, DMSO-$d_6$): δ 7.63 (d, J=8.7 Hz, 1H), 7.50 (dd, J=2.4 & 0.6 Hz, 1H), 7.32 (dd, J=8.4 & 2.4 Hz, 1H), 4.71 (s, 2H), 4.53 (s, 2H) and 3.30 (s, 3H) ppm.

3.2.b 2-Bromo-5-fluoro-1-[ ]-(methoxymethoxy)ethyl/benzene $^1$H-NMR (300.058 MHz, CDCl$_3$) δ ppm 1.43 (d, J=6.5 Hz, 3H), 3.38 (s, 3H), 4.55 (d, J=6.5 Hz, 1H), 4.63 (d, J=6.5 Hz, 1H), 5.07 (q, J=6.5 Hz, 1H), 6.85 (m, 1H), 7.25 (dd, J=9.7, 2.6 Hz, 1H), 7.46 (dd, J=8.8, 5.3 Hz, 1H).

3.2.c 2-Bromo-5-fluoro-1-[2-(methoxymethoxy)ethyl]benzene $^1$H-NMR (300.058 MHz, CDCl$_3$) δ ppm 3.04 (t, J=6.7 Hz, 2H), 3.31 (s, 3H), 3.77 (t, J=6.7 Hz, 2H), 4.62 (s, 2H), 6.82 (td, J=8.2, 3.2 Hz, 1H), 7.04 (dd, J=9.4, 2.9 Hz, 1H), 7.48 (dd, J=8.8, 5.3 Hz, 1H).

3.2.d 2-Bromo-4,5-difluoro-1-(methoxymethoxymethyl)benzene $^1$H-NMR (300.058 MHz, CDCl$_3$) δ ppm 3.42 (s, 3H), 4.57 (d, J=1.2 Hz, 2H), 4.76 (s, 2H), 7.3-7.5 (m, 2H).

3.2.e 2-Bromo-5-cyano-1-(methoxymethoxymethyl)benzene $^1$H-NMR (300.058 MHz, CDCl$_3$) δ ppm 3.43 (s, 3H), 4.65 (s, 2H), 4.80 (s, 2H), 7.43 (dd, J=8.2, 4.1 Hz, 1H), 7.66 (d, J=8.2 Hz, 1H), 7.82 (d, J=4.1 Hz, 1H).

3.2f 2-Bromo-5-methoxy-1-(methoxymethoxymethyl)benzene $^1$H NMR (300 MHz, DMSO-d$_6$): δ 7.48 (dd, J$_1$=1.2 Hz, J$_2$=1.2 Hz, 1H), 7.05 (d, J=2.7 Hz, 1H), 6.83 (dd, J=3 Hz, J$_2$=3 Hz, 1H), 4.69 (d, J=1.2 Hz, 2H), 4.5 (s, 2H), 3.74 (d, J=1.5 Hz, 3H), 3.32 (d, J=2.1 Hz, 3H) ppm.

3.2.g 1-Benzyl-1-(2-bromophenyl)-1-(methoxymethoxy)ethane $^1$H NMR (300 MHz, DMSO-d$_6$): δ 7.70-7.67 (m, 1H), 7.25-7.09 (m, 6H), 6.96-6.93 (m, 2H), 4.61 (d, 1H), 4.48 (d, 1H), 3.36-3.26 (m, 2H), 3.22 (s, 3H) and 1.63 (s, 3H) ppm.

3.2.h 2-Bromo-6-fluoro-1-(methoxymethoxymethyl)benzene $^1$H-NMR (300 MHz, CDCl$_3$) δ (ppm) 3.43 (s, 3H), 4.74 (s, 2H), 4.76 (d, J=2.1 Hz, 2H), 7.05 (t, J=9.1 Hz, 1H), 7.18 (td, J=8.2, 5.9 Hz, 1H), 7.40 (d, J=8.2 Hz, 1H).

3.2.i 2-Bromo-4-(4-cyanophenoxy)-1-(methoxymethoxymethyl)benzene $^1$H NMR (300 MHz, DMSO-d$_6$): δ 7.84 (d, 2H), 7.56 (d, 1H), 7.44 (d, 1H), 7.19-7.12 (m, 3H), 4.69 (s, 2H), 4.56 (s, 2H) and 3.31 (s, 3H) ppm.

3.2j 2-Bromo-5-(tert-butyldimethylsiloxy)-1-(methoxymethoxymethyl)benzene $^1$H-NMR (300 MHz, CDCl$_3$) δ (ppm) 0.19 (s, 6H), 0.98 (s, 9H), 3.43 (s, 3H), 4.59 (s, 2H), 4.75 (s, 2H), 6.64 (dd, J=8.5, 2.9 Hz, 1H), 6.98 (d, J=2.9 Hz, 1H), 7.36 (d, J=8.5 Hz, 1H).

3.2.k 2-Bromo-5-(2-cyanophenoxy)-1-(methoxymethoxymethyl)benzene $^1$H-NMR (300 MHz, CDCl$_3$) δ (ppm) 3.41 (s, 3H), 4.64 (s, 2H), 4.76 (s, 2H), 6.8-6.9 (m, 2H), 7.16 (td, J=7.6, 0.9 Hz, 1H), 7.28 (d, J=2.9 Hz, 1H), 7.49 (ddd, J=8.8, 7.6, 1.8 Hz, 1H), 7.56 (d, J=8.5 Hz, 1H), 7.67 (dd, J=7.9, 1.8 Hz, 1H).

3.2.l 2-Bromo-5-phenoxy-1-(methoxymethoxymethyl)benzene $^1$H-NMR (300 MHz, CDCl$_3$) δ (ppm) 3.40 (s, 3H), 4.62 (s, 2H), 4.74 (s, 2H), 6.80 (dd, J=8.8, 2.9 hz, 1H), 7.01 (d, J=8.5 Hz, 2H), 7.12 (t, J=7.9 Hz, 1H), 7.19 (d, J=2.9 hz, 1H), 7.35 (t, J=7.6 Hz, 2H), 7.48 (d, J=8.5 Hz, 1H).

Additional examples of compounds which can be produced by this method include 2-bromo-1-(methoxymethoxymethyl)benzene; 2-bromo-5-methyl-1-(methoxymethoxymethyl)benzene; 2-bromo-5-(methoxymethoxymethyl)-1-(methoxymethoxymethyl)benzene; 2-bromo-5-fluoro-1-(methoxymethoxymethyl)benzene; 1-bromo-2-(methoxymethoxymethyl)naphthalene; 2-bromo-4-fluoro-1-(methoxymethoxymethyl)benzene; 2-phenyl-1-(2-bromophenyl)-1-(methoxymethoxy)ethane; 2-bromo-5-(4-cyanophenoxy)-1-(methoxymethoxy methyl)benzene; 2-bromo-4-(3-cyanophenoxy)-1-(methoxymethoxymethyl)benzene; 2-bromo-4-(4-chlorophenoxy)-1-(methoxymethoxymethyl)benzene; 2-bromo-4-phenoxy-1-(methoxymethoxymethyl)benzene; 2-bromo-5-(3,4-dicyanophenoxy)-1-(methoxymethoxymethyl)benzene.

Example 4

Preparation of I from 4 Via 5

4.1 Metallation and Boronylation

To a solution of 4 (17.3 mmol) in anhydrous THF (80 mL) at −78° C. under nitrogen was added dropwise tert-BuLi or n-BuLi (11.7 mL) and the solution became brown colored. Then, B(OMe)$_3$ (1.93 mL, 17.3 mmol) was injected in one portion and the cooling bath was removed. The mixture was warmed gradually with stirring for 30 min and then stirred with a water bath for 2 h. After addition of 6N HCl (6 mL), the mixture was stirred overnight at room temperature and about 50% hydrolysis has happened as shown by TLC analysis. The solution was rotary evaporated and the residue was dissolved in MeOH (50 mL) and 6N HCl (4 mL). The solution was refluxed for 1 h and the hydrolysis was completed as indicated by TLC analysis. Rotary evaporation gave a residue which was dissolved in EtOAc, washed with water, dried and then evaporated. The crude product was purified by flash column chromatography over silica gel to provide a solid with 80% purity. The solid was further purified by washing with hexane to afford 7.2 mmol of I.

4.2 Results

Analytical data for exemplary compounds of structure I are provided below.

4.2.a 5-Chloro-1,3-dihydro-1-hydroxy-2,1-benzoxaborole (C1)

M.p. 142-150° C. MS (ESI): m/z=169 (M+1, positive) and 167 (M−1, negative). HPLC (220 nm): 99% purity. $^1$H NMR (300 MHz, DMSO-d$_6$): δ 9.30 (s, 1H), 7.71 (d, J=7.8 Hz, 1H), 7.49 (s, 1H), 7.38 (d, J=7.8 Hz, 1H) and 4.96 (s, 2H) ppm.

4.2.b 1,3-Dihydro-1-hydroxy-2,1-benzoxaborole (C2)

M.p. 83-86° C. MS (ESI): m/z=135 (M+1, positive) and 133 (M−1, negative). HPLC (220 nm): 95.4% purity. $^1$H NMR (300 MHz, DMSO-d$_6$): δ 9.14 (s, 1H), 7.71 (d, J=7.2 Hz, 1H), 7.45 (t, J=7.5 Hz, 1H), 7.38 (d, J=7.5 Hz, 1H), 7.32 (t, J=7.1 Hz, 1H) and 4.97 (s, 2H) ppm.

4.2.c 5-Fluoro-1,3-dihydro-1-hydroxy-3-methyl-2,1-benzoxaborole (C3)

$^1$H-NMR (300 MHz, DMSO-d$_6$) δ ppm 1.37 (d, J=6.4 Hz, 3H), 5.17 (q, J=6.4 Hz, 1H), 7.14 (m, 1H), 7.25 (dd, J=9.7, 2.3 Hz, 1H), 7.70 (dd, J=8.2, 5.9 Hz, 1H), 9.14 (s, 1H).

4.2.d 6-Fluoro-1-hydroxy-1,2,3,4-tetrahydro-2,1-benzoxaborine (C4)

$^1$H-NMR (300 MHz, DMSO-d$_6$) δ ppm 2.86 (t, J=5.9 Hz, 2H), 4.04 (t, J=5.9 Hz, 2H), 7.0-7.1 (m, 2H), 7.69 (dd, J=8.2, 7.2 Hz, 1H), 8.47 (s, 1H).

4.2.e 5,6-Difluoro-1,3-dihydro-1-hydroxy-2,1-benzoxaborole (C5)

$^1$H-NMR (300 MHz, DMSO-d$_6$) δ ppm 4.94 (s, 2H), 7.50 (dd, J=10.7, 6.8 Hz, 1H), 7.62 (dd, J=9.7, 8.2 Hz, 1H), 9.34 (s, 1H).

4.2.f 5-Cyano-1,3-dihydro-1-hydroxy-2,1-benzoxaborole (C6)

$^1$H-NMR (300 MHz, DMSO-d$_6$) δ ppm 5.03 (s, 2H), 7.76 (d, J=8.2 Hz, 1H), 7.89 (d, J=8.2 Hz, 1H), 7.90 (s, 1H), 9.53 (s, 1H).

4.2.g 1,3-Dihydro-1-hydroxy-5-methoxy-2,1-benzoxaborole (C7)

M.p. 102-104° C. MS ESI: m/z=165.3 (M+1) and 162.9 (M−1). $^1$H NMR (300 MHz, DMSO-d$_6$): δ 8.95 (s, 1H), 7.60 (d, J=8.1 Hz, 1H), 6.94 (s, 1H), 6.88 (d, J=8.1 Hz, 1H), 4.91 (s, 2H), 3.77 (s, 3H) ppm.

4.2.h 1,3-Dihydro-1-hydroxy-5-methyl-2,1-benzoxaborole (C8)

M.p. 124-128° C. MS ESI: m/z=148.9 (M+1) and 146.9 (M−1). $^1$H NMR (300 MHz, DMSO-d$_6$): δ 9.05 (s, 1H), 7.58 (d, J=7.2 Hz, 1H), 7.18 (s, 1H), 7.13 (d, J=7.2 Hz, 1H), 4.91 (s, 2H), 2.33 (s, 3H) ppm.

4.2.i 1,3-Dihydro-1-hydroxy-5-hydroxymethyl-2,1-benzoxaborole (C9)

MS: m/z=163 (M−1, ESI−). $^1$H NMR (300 MHz, DMSO-d$_6$): δ 9.08 (s, 1H), 7.64 (d, 1H), 7.33 (s, 1H), 7.27 (d, 1H), 5.23 (t, 1H), 4.96 (s, 2H), 4.53 (d, 2H) ppm.

4.2.j 1,3-Dihydro-5-fluoro-1-hydroxy-2,1-benzoxaborole (C10)

M.p. 110-114° C. MS ESI: m/z=150.9 (M−1). $^1$H NMR (300 MHz, DMSO-d$_6$): δ 9.20 (s, 1H), 7.73 (dd, J$_1$=6 Hz, J$_2$=6 Hz, 1H), 7.21 (m, 1H), 7.14 (m, 1H), 4.95 (s, 2H) ppm.

4.2.k 1,3-Dihydro-2-oxa-1-cyclopenta[á]naphthalene (C11)

M.P. 139-143° C. MS ESI: m/z=184.9 (M+1). $^1$H NMR (300 MHz, DMSO-d$_6$): δ 9.21 (s, 1H), 8.28 (dd, J=6.9 Hz, J$_2$=0.6 Hz, 1H), 7.99 (d, J=8.1 Hz, 1H), 7.95 (d, J=7.5 Hz, 1H), 7.59-7.47 (m, 3H), 5.09 (s, 2H) ppm.

4.2.l 7-Hydroxy-2,1-oxaborolano[5,4-c]pyridine (C12)

$^1$H-NMR (300 MHz, DMSO-d$_6$): δ ppm 5.00 (s, 2H), 7.45 (d, J=5.0 Hz, 1H), 8.57 (d, J=5.3 Hz, 1H), 8.91 (s, 1H), 9.57 (s, 1H). ESI-MS m/z 134 (M−H)$^-$, C$_6$H$_6$BNO$_2$=135.

4.2.m 1,3-Dihydro-6-fluoro-1-hydroxy-2,1-benzoxaborole (C13)

M.p. 110-117.5° C. MS (ESI): m/z=151 (M−1, negative). HPLC (220 nm): 100% purity. $^1$H NMR (300 MHz, DMSO-d$_6$): δ 9.29 (s, 1H), 7.46-7.41 (m, 2H), 7.29 (td, 1H) and 4.95 (s, 2H) ppm.

4.2.n 3-Benzyl-1,3-dihydro-1-hydroxy-3-methyl-2,1-benzoxaborole (C14)

MS (ESI): m/z=239 (M+1, positive). HPLC: 99.5% purity at 220 nm and 95.9% at 254 nm. $^1$H NMR (300 MHz, DMSO-d$_6$): δ 8.89 (s, 1H), 7.49-7.40 (m, 3H), 7.25-7.19 (m, 1H), 7.09-7.05 (m, 3H), 6.96-6.94 (m, 2H), 3.10 (d, 1H), 3.00 (d, 1H) and 1.44 (s, 3H) ppm.

4.2.o 3-Benzyl-1,3-dihydro-1-hydroxy-2,1-benzoxaborole (C15)

MS (ESI+): m/z=225 (M+1). HPLC: 93.4% purity at 220 nm. $^1$H NMR (300 MHz, DMSO-d$_6$): δ 9.08 (s, 1H), 7.63 (dd, 1H), 7.43 (t, 1H), 7.35-7.14 (m, 7H), 5.38 (dd, 1H), 3.21 (dd, 1H) and 2.77 (dd, 1H) ppm.

4.2.p 1,3-Dihydro-4-fluoro-1-hydroxy-2,1-benzoxaborole (C16)

$^1$H-NMR (300 MHz, DMSO-d$_6$) δ (ppm) 5.06 (s, 2H), 7.26 (ddd, J=9.7, 7.9, 0.6 Hz, 1H), 7.40 (td, J=8.2, 4.7 Hz, 1H), 7.55 (d, J=7.0 Hz, 1H), 9.41 (s, 1H).

4.2.q 5-(4-Cyanophenoxy)-1,3-dihydro-1-hydroxy-2,1-benzoxaborole (C17)

$^1$H-NMR (300 MHz, DMSO-d$_6$) δ ppm 4.95 (s, 2H), 7.08 (dd, J=7.9, 2.1 Hz, 1H), 7.14 (d, J=8.8 Hz, 1H), 7.15 (d, J=2.1 Hz, 1H), 7.78 (d, J=7.9 Hz, 1H), 7.85 (d, J=9.1 Hz, 2H), 9.22 (s, 1H).

4.2.r 6-(4-Cyanophenoxy)-1,3-dihydro-1-hydroxy-2,1-benzoxaborole (C18)

M.p. 148-151° C. MS: m/z=252 (M+1) (ESI+) and m/z=250 (M−1) (ESI−). HPLC: 100% purity at 254 nm and 98.7% at 220 nm. $^1$H NMR (300 MHz, DMSO-d$_6$): δ 9.26 (s, 1H), 7.82 (d, 2H), 7.50 (d, 1H), 7.39 (d, 1H), 7.26 (dd, 1H), 7.08 (d, 2H) and 4.99 (s, 2H) ppm

4.2.s 6-(3-Cyanophenoxy)-1,3-dihydro-1-hydroxy-2,1-benzoxaborole (C19)

M.p. 146-149° C. MS: m/z=252 (M+1) (ESI+) and m/z=250 (M−1) (ESI−). HPLC: 100% purity at 254 nm and 97.9% at 220 nm. $^1$H NMR (300 MHz, DMSO-d$_6$): δ 9.21 (s, 1H), 7.60-7.54 (m, 2H), 7.50-7.45 (m, 2H), 7.34-7.30 (m, 2H), 7.23 (dd, 1H) and 4.98 (s, 2H) ppm.

4.2.t 6-(4-Chlorophenoxy)-1,3-dihydro-1-hydroxy-2,1-benzoxaborole (C20)

M.p. 119-130° C. MS: m/z=261 (M+1) (ESI+) and m/z=259 (M−1) (ESI−). HPLC: 100% purity at 254 nm and 98.9% at 220 nm. $^1$H NMR (300 MHz, DMSO-$d_6$): δ 9.18 (s, 1H), 7.45-7.41 (m, 3H), 7.29 (d, 1H), 7.19 (dd, 1H), 7.01 (d, 2H) and 4.96 (s, 2H) ppm.

4.2.u 6-Phenoxy-1,3-dihydro-1-hydroxy-2,1-benzoxaborole (C21)

M.p. 95-99° C. MS: m/z=227 (M+1) (ESI+) and m/z=225 (M−1) (ESI−). HPLC: 100% purity at 254 nm and 98.4% at 220 nm. $^1$H NMR (300 MHz, DMSO-$d_6$): δ 9.17 (s, 1H), 7.43-7.35 (m, 3H), 7.28 (s, 1H), 7.19-7.09 (m, 2H), 6.99 (d, 2H) and 4.96 (s, 2H) ppm.

4.2.v 5-(4-Cyanobenzyloxy)-1,3-dihydro-1-hydroxy-2,1-benzoxaborole (C22)

$^1$H-NMR (300 MHz, DMSO-$d_6$) δ (ppm) 4.90 (s, 2H), 5.25 (s, 2H), 6.98 (dd, J=7.9, 2.1 Hz, 1H), 7.03 (d, J=1.8 Hz, 1H), 7.62 (d, J=7.9 Hz, 1H), 7.64 (d, J=8.5 Hz, 2H), 7.86 (d, J=8.5 Hz, 1H), 9.01 (s, 1H).

4.2.w 5-(2-Cyanophenoxy)-1,3-dihydro-1-hydroxy-2,1-benzoxaborole (C23)

$^1$H-NMR (300 MHz, DMSO-$d_6$) δ (ppm) 4.95 (s, 2H), 7.0-7.2 (m, 3H), 7.32 (td, J=7.6, 1.2 Hz, 1H), 7.68 (ddd, J=9.1, 7.6, 1.8 Hz, 1H), 7.77 (d, J=7.9 Hz, 1H), 7.91 (dd, J=7.9, 1.8 Hz, 1H).

4.2.x 5-Phenoxy-1,3-dihydro-1-hydroxy-2,1-benzoxaborole (C24)

$^1$H-NMR (300 MHz, DMSO-$d_6$) δ (ppm) 4.91 (s, 2H), 6.94 (s, 1H), 6.96 (d, J=8.8 Hz, 1H), 7.05 (d, J=7.6 Hz, 2H), 7.17 (t, J=7.3 Hz, 1H), 7.41 (t, J=7.3 Hz, 2H), 7.70 (d, J=8.5 Hz, 1H), 9.11 (s, 1H).

4.2.y 5-[4-(N,N-Diethylcarbamoyl)phenoxy]-1,3-dihydro-1-hydroxy-2,1-benzoxaborole (C25)

$^1$H-NMR (300 MHz, DMSO-$d_6$) δ (ppm) 1.08 (br s, 6H), 3.1-3.5 (m, 4H), 4.93 (s, 2H), 7.0-7.1 (m, 4H), 7.37 (d, J=8.5 Hz, 2H), 7.73 (d, J=7.9 Hz, 1H), 9.15 (s, 1H).

4.2.z 1,3-Dihydro-1-hydroxy-5-[4-(morpholinocarbonyl)phenoxy]-2,1-benzoxaborole (C26)

$^1$H-NMR (300 MHz, DMSO-$d_6$) δ (ppm) 3.3-3.7 (m, 8H), 4.93 (s, 2H), 7.0-7.1 (m, 4H), 7.44 (d, J=8.8 Hz, 2H), 7.73 (d, J=7.9 Hz, 1H), 9.16 (s, 1H).

4.2.aa 5-(3,4-Dicyanophenoxy)-1,3-dihydro-1-hydroxy-2,1-benzoxaborole (C27)

$^1$H-NMR (300 MHz, DMSO-$d_6$) δ (ppm) 4.97 (s, 2H), 7.13 (dd, J=7.9, 2.1 Hz, 1H), 7.21 (d, J=1.5 Hz, 1H), 7.43 (dd, J=8.8, 2.6 Hz, 1H), 7.81 (d, J=7.9 Hz, 1H), 7.82 (d, J=2.6 Hz, 1H), 8.11 (d, J=8.5 Hz, 1H), 9.26 (s, 1H).

4.2.ab 6-Phenylthio-1,3-dihydro-1-hydroxy-2,1-benzoxaborole (C28)

M.p. 121-124° C. MS: m/z=243 (M+1) (ESI+) and m/z=241 (M−1) (ESI−). HPLC: 99.6% purity at 254 nm and 99.6% at 220 nm. $^1$H NMR (300 MHz, DMSO-$d_6$): δ 9.25 (s, 1H), 7.72 (dd, 1H), 7.48 (dd, 1H), 7.43 (dd, 1H), 7.37-7.31 (m, 2H), 7.29-7.23 (m, 3H), and 4.98 (s, 2H) ppm.

4.2.ac 6-(4-trifluoromethoxyphenoxy)-1,3-dihydro-1-hydroxy-2,1-benzoxaborole (C29)

M.p. 97-101° C. MS: m/z=311 (M+1) (ESI+) and m/z=309 (M−1) (ESI−). HPLC: 100% purity at 254 nm and 100% at 220 nm. $^1$H NMR (300 MHz, DMSO-$d_6$): δ 9.20 (s, 1H), 7.45 (d, 1H), 7.37 (d, 2H), 7.33 (d, 1H), 7.21 (dd, 1H), 7.08 (d, 2H), and 4.97 (s, 2H) ppm.

4.2.ad 5-(N-Methyl-N-phenylsulfonylamino)-1,3-dihydro-1-hydroxy-2,1-benzoxaborole (C30)

M.p. 85-95° C. MS: m/z=304 (M+1) (ESI+) and m/z=302 (M−1) (ESI−). HPLC: 96.6% purity at 254 nm and 89.8% at 220 nm. $^1$H NMR (300 MHz, DMSO-$d_6$): δ 9.23 (s, 1H), 7.72-7.63 (m, 2H), 7.56 (t, 2H), 7.50 (d, 2H), 7.16 (s, 1H), 7.03 (d, 1H), 4.91 (s, 2H) and 3.14 (s, 3H) ppm.

4.2.ae 6-(4-Methoxyphenoxy)-1,3-dihydro-1-hydroxy-2,1-benzoxaborole (C31)

M.p. 126-129° C. MS: m/z=257 (M+1) (ESI+) and m/z=255 (M−1) (ESI−). HPLC: 98.4% purity at 254 nm and 98.4% at 220 nm. $^1$H NMR (300 MHz, DMSO-$d_6$): δ 9.14 (s, 1H), 7.36 (d, 1H), 7.19 (s, 1H), 7.12 (d, 1H), 6.98 (d, 2H), 6.95 (d, 2H), 4.93 (s, 2H) and 3.73 (s, 3H) ppm.

4.2.af 6-(4-Methoxyphenylthio)-1,3-dihydro-1-hydroxy-2,1-benzoxaborole (C32)

M.p. 95-100° C. MS: m/z=272 (M+), 273 (M+1) (ESI+) and m/z=271 (M−1) (ESI−). HPLC: 100% purity at 254 nm and 99.2% at 220 nm. $^1$H NMR (300 MHz, DMSO-$d_6$): δ 9.20 (s, 1H), 7.51 (d, 1H), 7.39-7.28 (m, 4H), 6.98 (d, 2H), 4.93 (s, 2H) and 3.76 (s, 3H) ppm.

4.2.ag 6-(4-Methoxyphenylsulfonyl)-1,3-dihydro-1-hydroxy-2,1-benzoxaborole (C33)

M.p. 180-192° C. MS: m/z=305 (M+1) (ESI+) and m/z=303 (M−1) (ESI−). HPLC: 96.8% purity at 254 nm and 95.5% at 220 nm. $^1$H NMR (300 MHz, DMSO-$d_6$): δ 9.46 (s, 1H), 8.28 (s, 1H), 7.99 (d, 1H), 7.85 (d, 2H), 7.61 (d, 1H), 7.11 (d, 2H), 5.02 (s, 2H) and 3.80 (s, 3H) ppm.

4.2.ah 6-(4-Methoxyphenylsulfinyl)-1,3-dihydro-1-hydroxy-2,1-benzoxaborole (C34)

$^1$H NMR (300 MHz, DMSO-$d_6$): δ 9.37 (s, 1H), 8.02 (d, 1H), 7.71 (dd, 1H), 7.59 (d, 2H), 7.53 (d, 1H), 7.07 (d, 2H), 5.00 (s, 2H) and 3.76 (s, 3H) ppm.

4.2.ai 5-Trifluoromethyl-1,3-dihydro-1-hydroxy-2,1-benzoxaborole (C35)

M.p. 113-118° C. MS: m/z=203 (M+1) (ESI+) and m/z=201 (M−1) (ESI−). HPLC: 100% purity at 254 nm and 100% at 220 nm. $^1$H NMR (300 MHz, DMSO-$d_6$): δ 9.48 (s, 1H), 7.92 (d, 1H), 7.78 (s, 1H), 7.67 (d, 1H) and 5.06 (s, 2H) ppm.

4.2.aj 4-(4-Cyanophenoxy)-1,3-dihydro-1-hydroxy-2,1-benzoxaborole (C36)

For coupling reaction between 4-fluorobenzonitrile and substituted phenol to give starting material 2, see Igarashi, S.; et al. *Chemical & Pharmaceutical Bulletin* (2000), 48(11), 1689-1697.

$^1$H-NMR (300 MHz, DMSO-d$_6$) (ppm) 4.84 (s, 2H), 7.08 (d, J=8.2 Hz, 2H), 7.18 (d, J=7.9 Hz, 1H), 7.45 (t, J=7.3 Hz, 1H), 7.63 (d, J=7.3 Hz, 1H), 7.82 (d, J=8.5 Hz, 2H).

4.2.ak 5-(3-Cyanophenoxy)-1,3-dihydro-1-hydroxy-2,1-benzoxaborole (C37)

For coupling between 3-fluorobenzonitrile and substituted phenol to give starting material 2: Li, F. et al., *Organic Letters* (2003), 5(12), 2169-2171.

$^1$H-NMR (300 MHz, DMSO-d$_6$) (ppm) 4.93 (s, 2H), 7.0-7.1 (m, 2H), 7.3-7.4 (m, 1H), 7.5-7.7 (m, 3H), 7.75 (d, J=8.2 Hz, 1H).

4.2.al 5-(4-Carboxyphenoxy)-1-hydroxy-2,1-benzoxaborole (C38)

To a solution of 5-(4-cyanophenoxy)-1-hydroxy-2,1-benzoxaborole obtained in C17 (430 mg, 1.71 mmol) in ethanol (10 mL) was added 6 mol/L sodium hydroxide (2 mL), and the mixture was refluxed for 3 hours. Hydrochloric acid (6 mol/L, 3 mL) was added, and the mixture was extracted with ethyl acetate. The organic layer was washed with brine and dried on anhydrous sodium sulfate. The solvent was removed under reduced pressure, and the residue was purified by silica gel column chromatography (ethyl acetate) followed by trituration with diisopropyl ether to give the target compound (37 mg, 8%).

$^1$H-NMR (300 MHz, DMSO-d$_6$) δ (ppm) 4.94 (s, 2H), 7.0-7.1 (m, 4H), 7.76 (d, J=7.9 Hz, 1H), 7.94 (d, J=8.8 Hz, 2H), 9.19 (s, 1H), 12.8 (br s, 1H).

4.2.am 1-Hydroxy-5-[4-(tetrazole-1-yl)phenoxy]-2,1-benzoxaborole (C39)

A mixture of 5-(4-cyanophenoxy)-1-hydroxy-2,1-benzoxaborole (200 mg, 0.797 mmol), sodium azide (103 mg, 1.59 mmol), and ammonium chloride (85 mg, 1.6 mmol) in N,N-dimethylformamide (5 mL) was stirred at 80° C. for two days. Water was added, and the mixture was extracted with ethyl acetate. The organic layer was washed with water and brine, and dried on anhydrous sodium sulfate. The solvent was removed under reduced pressure, and the residue was purified by silica gel column chromatography (ethyl acetate) followed by trituration with ethyl acetate to give the target compound (55 mg, 23%).

$^1$H-NMR (300 MHz, DMSO-d$_6$) δ (ppm) 4.95 (s, 2H), 7.0-7.1 (m, 2H), 7.23 (d, J=8.8 Hz, 2H), 7.76 (d, J=7.9 Hz, 1H), 8.05 (d, J=8.5 Hz, 2H), 9.18 (br s, 1H).

Example 5

Preparation of I from 2 Via 6

5.1 Catalytic Boronylation, Reduction and Cyclization

A mixture of 2 (10.0 mmol), bis(pinacolato)diboron (2.79 g, 11.0 mmol), PdCl$_2$(dppf) (250 mg, 3 mol %), and potassium acetate (2.94 g, 30.0 mmol) in 1,4-dioxane (40 mL) was stirred at 80° C. for overnight. Water was added, and the mixture was extracted with ethyl acetate. The organic layer was washed with brine and dried on anhydrous sodium sulfate. The solvent was removed under reduced pressure. The crude product was dissolved in tetrahydrofuran (80 mL), then sodium periodate (5.56 g, 26.0 mmol) was added. After stirring at room temperature for 30 min, 2N HCl (10 mL) was added, and the mixture was stirred at room temperature for overnight. Water was added, and the mixture was extracted with ethyl acetate. The organic layer was washed with brine and dried on anhydrous sodium sulfate. The solvent was removed under reduced pressure, and the residue was treated with ether to afford 6.3 mmol of the corresponding boronic acid. To the solution of the obtained boronic acid (0.595 mmol) in methanol (5 mL) was added sodium borohydride (11 mg, 0.30 mmol), and the mixture was stirred at room temperature for 1 h. Water was added, and the mixture was extracted with ethyl acetate. The organic layer was washed with brine and dried on anhydrous sodium sulfate. The solvent was removed under reduced pressure, and the residue was purified by silica gel column chromatography to give 0.217 mmol of I.

5.2 Results

Analytical data for exemplary compounds of structure I are provided below.

5.2.a 1,3-Dihydro-5-fluoro-1-hydroxy-2,1-benzoxaborole (C10)

Analytical data for this compound is listed in 4.2.j.

Example 6

Preparation of I from 3

6.1 One-Pot Boronylation and Cyclization

To a solution of 3 (4.88 mmol) and triisopropyl borate (1.35 mL, 5.86 mmol) in tetrahydrofuran (10 mL) was added n-butyllithium (1.6 mol/L in hexanes; 6.7 mL, 10.7 mmol) dropwise over 15 min at −78° C. under nitrogen atmosphere, and the mixture was stirred for 2 h while allowing to warm to room temperature. The reaction was quenched with 2N HCl, and extracted with ethyl acetate. The organic layer was washed with brine and dried on anhydrous sodium sulfate. The solvent was removed under reduced pressure, and the residue was purified by silica gel column chromatography and treated with pentane to give 0.41 mmol of I.

6.2 Results

Analytical data for exemplary compounds of structure I are provided below.

6.2.a 1,3-Dihydro-5-fluoro-1-hydroxy-2,1-benzoxaborole (C10)

Analytical data for this compound is listed in 4.2.j.

Example 7

Preparation of I from 3

7.1 One-Pot Boronylation and Cyclization with Distillation

To a solution of 3 (4.88 mmol) in toluene (20 mL) was added triisopropyl borate (2.2 mL, 9.8 mmol), and the mixture was heated at reflux for 1 h. The solvent, the generated isopropyl alcohol and excess triisopropyl borate were removed under reduced pressure. The residue was dissolved in tetrahydrofuran (10 mL) and cooled to −78° C. n-Butyllithium (3.2 mL, 5.1 mmol) was added dropwise over 10 min, and the mixture was stirred for 1 h while allowing to warm to room temperature. The reaction was quenched with 2N HCl, and extracted with ethyl acetate. The organic layer was washed with brine and dried on anhydrous sodium sulfate. The solvent was removed under reduced pressure, and the residue was purified by silica gel column chromatography to give 1.54 mmol of I.

7.2 Results

Analytical data for exemplary compounds of structure I are provided below.

7.2.a 1,3-Dihydro-5-fluoro-1-hydroxy-2,1-benzoxaborole (C10)

Analytical data for this compound is listed in 4.2.j.

Example 8

Preparation of 8 from 7

8.1 Bromination

To a solution of 7 (49.5 mmol) in carbon tetrachloride (200 mL) were added N-bromosuccinimide (8.81 g, 49.5 mmol) and N,N-azoisobutylonitrile (414 mg, 5 mol %), and the mixture was heated at reflux for 3 h. Water was added, and the mixture was extracted with chloroform. The organic layer was washed with brine and dried on anhydrous sodium sulfate. The solvent was removed under reduced pressure to give the crude methyl-brominated intermediate 8.

Example 9

Preparation of 3 from 8

9.1 Hydroxylation

To crude 8 (49.5 mmol) were added dimethylformamide (150 mL) and sodium acetate (20.5 g, 250 mmol), and the mixture was stirred at 80° C. for overnight. Water was added, and the mixture was extracted with ether. The organic layer was washed with water and brine, and dried on anhydrous sodium sulfate. The solvent was removed under reduced pressure. To the residue was added methanol (150 mL) and 1N sodium hydroxide (50 mL), and the mixture was stirred at room temperature for 1 h. The reaction mixture was concentrated to about a third of volume under reduced pressure. Water and hydrochloric acid were added, and the mixture was extracted with ethyl acetate. The organic layer was washed with water and brine, and dried on anhydrous sodium sulfate. The solvent was removed under reduced pressure, and the residue was purified by silica gel column chromatography followed by trituration with dichloromethane to give 21.8 mmol of 3.

9.2 Results

Exemplary compounds of structure 3 prepared by the method above are provided below.

9.2.a 2-Bromo-5-cyanobenzyl Alcohol $^1$H-NMR (300 MHz, DMSO-d$_6$) δ ppm 4.51 (d, J=5.9 Hz, 2H), 5.67 (t, J=5.6 Hz, 1H), 7.67 (dd, J=8.2, 2.0 Hz, 1H), 7.80 (s, J=8.2 Hz, 1H), 7.83 (d, J=2.0 Hz, 1H).

Additional examples of compounds which can be produced by this method include 2-bromo-5-(4-cyanophenoxy) benzyl alcohol.

Example 10

Preparation of 9 from 2

10.1 Reaction

A mixture of 2 (20.0 mmol), (methoxymethyl)triphenylphosphonium chloride (8.49 g, 24.0 mmol), and potassium tert-butoxide (2.83 g, 24.0 mol) in N,N-dimethylformamide (50 mL) was stirred at room temperature for overnight. The reaction was quenched with 6 N HCl, and the mixture was extracted with ethyl acetate. The organic layer was washed with water (×2) and brine, and dried on anhydrous sodium sulfate. The solvent was removed under reduced. To the residue were added tetrahydrofuran (60 mL) and 6 N HCl, and the mixture was heated at reflux for 8 h. Water was added, and the mixture was extracted with ether. The organic layer was washed with brine and dried on anhydrous sodium sulfate. The solvent was removed under reduced pressure to afford 16.6 mmol of 9.

Example 11

Preparation Method of Step 13

11.1 Reaction

A solution of I in an appropriate alcohol solvent (R$^1$—OH) was refluxed under nitrogen atmosphere and then distilled to remove the alcohol to give the corresponding ester.

Example 12

Preparation of Ib from Ia 12.1 Reaction

To a solution of Ia in toluene was added amino alcohol and the participated solid was collected to give Ib.

12.2 Results (500 mg, 3.3 mmol) was dissolved in toluene (37 mL) at 80° C. and ethanolamine (0.20 mL, 3.3 mmol) was added. The mixture was cooled to room temperature, then ice bath, and filtered to give C40 as a white powder (600.5 mg, 94%).

12.2a (C40)

$^1$H-NMR (300 MHz, DMSO-d$_6$) 6 (ppm) 2.88 (t, J=6.2 Hz, 2H), 3.75 (t, J=6.3 Hz, 2H), 4.66 (s, 2H), 5.77 (br, 2H), 6.85-6.91 (m, 2H), 7.31 (td, J=7.2, 1.2 Hz, 1H).

Example 13

Formulations

Compounds of the present invention can be administered to a patient using a therapeutically effective amount of a compound of Formulae (I) or (II) in any one of the following three lacquer formulations and one solvent formulation. The lacquer formulation provides good durability while the solvent formulation provides good ease of use. These compounds can also be applied using a spray formulation, paint-on lacquer, drops, or other.

1. 20% propylene glycol; 70% ethanol; 10% compound of invention;

2. 70% ethanol; 20% poly(vinyl methyl ether-alt-maleic acid monobutyl ester); 10% compound of the invention;
3. 56% ethanol; 14% water; 15% poly(2-hydroxyethyl methacrylate); 5% dibutyl sebacate; 10% compound of the invention;
4. 55% ethanol; 15% ethyl acetate; 15% poly(vinyl acetate); 5% dibutyl sebacate; 10% compound of the invention.

The preparation of these formulations is well known in the art and is found in references such as *Remington: The Science and Practice of Pharmacy*, supra.

Example 14

Antifungal MIC Testing

All MIC testing followed the National Committee for Clinical Laboratory Standards (NCCLS) guidelines for antimicrobial testing of yeasts and filamentous fungi (Pfaller et al., NCCLS publication M38-A—Reference Method for Broth Dilution Antifungal Susceptibility Testing of Filamentous Fungi; Approved Standard. Wayne, Pa.: NCCLS; 2002 (Vol. 22, No. 16) except the *Malassezia* species which incubated in a urea broth (Nakamura et al., *Antimicrobial Agents And Chemotherapy*, 2000, 44(8) p. 2185-2186). Results of the MIC testing is provided in FIG. 1.

Example 15

Keratin Assay

Many antifungal agents strongly bind to keratin which not only reduces their antifungal potency but also may restrict their penetration into the nail. The affinities of the compounds for keratin powder was determined by a method described in Tatsumi, *Antimicrobial Agents and Chemotherapy*, 46(12): 3797-3801 (2002).

A comparison of MIC data for several compounds of the invention against *T. rubrum*, with and without the presence of 5% keratin, is provided in FIG. 1.

Example 16

(C10) Antifungal Spectrum of Activity (C10) is a novel compound in development for use as a topical antifungal treatment. The purpose of this study was to determine the minimum inhibitory concentration (MIC) for (C10) against 19 test strains of fungi including: *Aspergilus fumigatus* (*A. fumigatus*), *Candida Albicans* (*C. albicans*, both fluconazole sensitive and resistant strains), *Candida glabrata* (*C. glabrata*), *Candida krusei* (*C. krusei*), *Cryptococcus neoformans* (*C. neoformans*), *Candida parapsilosis* (*C. parapsilosis*), *Candida tropicalis* (*C. tropicalis*), *Epidermophyton floccosum* (*E. floccosum*), *Fusarium solani* (*F. solani*), *Malassezia furfur* (*M. furfur*), *Malassezia pachydermatis* (*M. pachydermatis*), *Malassezia sympodialis* (*M. sympodialis*), *Microsporum audouinii* (*M. audouinii*), *Microsporum canis* (*M. canis*), *Microsporum gypseum* (*M. gypseum*), *Trichophyton mentagrophytes* (*T. mentagrophytes*), *Trichophyton rubrum* (*T. rubrum*), *Trichophyton tonsurans* (*T. tonsurans*). Fungal growth was evaluated after exposure to different concentrations of (C10). In addition, the MIC for (C10) against *T. rubrum* in the presence of 5% keratin powder and the minimum fungicidal concentration (MFC) for (C10) against *T. rubrum* and *T. mentagrophytes* were also determined. Ciclopirox and/or terbinafine and/or fluconazole and/or itraconazole were used as comparators and tested in a similar manner. These studies were conducted at NAEJA Pharmaceutical, Inc.

Materials and Methods (C10) was obtained from Anacor Pharmaceuticals, Inc. (Palo Alto, Calif., USA). ATCC strains were obtained from ATCC (Manassas, Va., USA). Ciclopirox-olamine was obtained from Sigma-Aldrich Co. (St. Louis, Mo., USA). Terbinafine, fluconazole and itraconazole were synthesized at NAEJA Pharmaceutical Inc. (Edmonton, AB, Canada), experimental procedures and analytical data for these standards are stored in NAEJA archives.

All MIC testing followed the National Committee for Clinical Laboratory Standards (NCCLS) guidelines for antimicrobial testing of yeasts and filamentous fungi (Pfaller et al., 2002) except the *Malassezia* species which were incubated in a urea broth (Nakamura et al., 2000). The microbroth dilution method was used to test the in vitro activity of (C10) against 19 test strains of fungi. Briefly, compounds were dissolved in DMSO and diluted in sterile water to give a working stock. Two-fold serial dilutions of the working stock were prepared in 96-well plates and media was added. Media was RPMI, RPMI+MOPS, modified RPMI, or modified Urea broth. The plates were inoculated with the fungal suspensions to give a final inoculum size of $0.5\text{-}2.5\times10^3$ cells/mL for yeasts or $0.4\text{-}5\times10^4$ CFU/mL for filamentous fungi and then incubated for 24-168 h at 35° C. The final concentration of DMSO did not exceed 5%. The MIC was defined as the lowest concentration that resulted in over 90% reduction of growth, as compared to a drug-free control. The MFC was defined as the lowest concentration that killed over 90% of the fungi, as compared to a drug-free control.

Results and Conclusions

The results for the MIC of (C10) and reference compounds against 19 strains of fungi are shown in FIG. 2. The results for the MFC of AN2690 against 2 strains of fungi are shown in Table 2. (C10) had MIC values ranging from 0.25-2 µg/mL against all fungi tested. Addition of 5% keratin powder to the media did not effect the MIC against *T. rubrum*. (C10) had fungicidal activity against *T. rubrum* and *T. mentagrophytes* with MFC values of 8 and 16 µg/mL, respectively. Reference compounds had MIC values in the range defined by NCCLS.

Example 17

The Solubility, Stability and Log P Determination of Compounds of the Present Invention by LC/MS/MS The solubility, room temperature stability and Log P of C10 was determined by the following methodology.

Reagents and Standards:

Ethanol: 200 proof ACS Grade (EM Science, Gibbstown, N.J., USA); Octanol: Octyl alcohol (EM Science, Gibbstown, N.J., USA); Acetonitrile: HPLC Grade (Burdick & Jackson, Muskegon, Mich., USA); Ammonium Acetate: lot 3272X49621 (Mallinckrodt, Phillipsburg, N.J., USA); C10: lot A032-103 (Anacor Pharmaceuticals, Palo Alto, Calif., USA); p-Nitrophenol (PNP): lot OGNO1 (TCI America, Portland, Oreg., USA); Water: Deionized water (from Millipore systems, Billerica, Mass., USA)

Solubility

N-Octanol and water were mutually pre-saturated by vigorously stirring a mixture of both solvents for up to 12 h and the mixture was allowed to separate. Solubility in each solvent was determined by adding 10 µL of 20, 40, 200, 1000 and 5000 µg/mL of C10 in DMSO to the pre-saturated n-octanol or water. After the sample was vortexed for 10 sec, the sample was centrifuged for 10 min at ca. 3000 rpm. A visual inspection was made to determine if the sample was clear or if a pellet had formed on the bottom of the tube.

Log P

C10 (10 µL of 5000 µ/mL) at 2× the final concentration was added to 0.5 mL pre-saturated n-octanol and mixed. An equal volume (0.5 mL) of pre-saturated water was added, vortex mixed and then mixed on a rotating shaker for one hour and 24 h in triplicate at ca. 25° C. The organic and aqueous layers were separated by centrifugation for 5 min at ca. 2000 rpm. Twenty five µL of the octanol (top) layer were removed and placed in a pre-labeled tube. Twenty five µL of the aqueous layer (bottom) were removed, taking care to avoid octanol contamination, and placed in a pro-labeled tube.

Stability at Room Temperature

C10 (10 µL of 5000 µg/mL) was added both to 0.5 mL n-octanol and 0.5 mL water in triplicate. Samples were mixed. At 0 h and 24 h samples were stored at ca. −20° C. Twenty five µL of sample was used for analysis.

Extraction Procedure C10

For the octanol sample, 25 µL of ethanol, 25 µL of water and 300 µL of acetonitrile containing the internal standard was added. For the water sample, 25 µL of ethanol, 25 µL of octanol and 300 µL of acetonitrile containing the internal standard [60 mL of acetonitrile add 6 µL of PNP (1000 µg/mL)] was added. For the calibrators 25 µL of octanol, 25 µL of water and 300 µL of acetonitrile containing the internal standard was added. The sample was vortexed for 10 seconds. Two hundred µL of the organic layer were transferred into a clean deactivated autosampler vial.

Calculations

A 1/concentration weighted linear regression was used for the quantitation of C10. All integration were performed with peak areas using Analyst version 1.3, Applied Biosystems. For C10, peak area ratios analyte to internal standard PNP were used for all quantitation.

The partition coefficient (P) was calculated according to the equation detailed below:

$$P = [\text{Sample concentration}]_{octanol} / [\text{Sample concentration}]_{water}$$

$$\text{Log } P = \log_{10}(\text{partition coefficient})$$

Results:

As shown in Table 17A the solubility of C10 in both octanol and water is very good over the concentration range tested.

TABLE 17A

Solubility of C10 in water and octanol

| Targeted Conc (µg/mL) | Water Visual | Octanol Visual |
|---|---|---|
| 0.800 | Clear | Clear |
| 4.00 | Clear | Clear |
| 20.0 | Clear | Clear |
| 100 | Clear | Clear |

Table 17B shows the results of the log P determination after 1 h and 24 h for C10. The mean log P after 1 h was 1.97 (n=3). After 24 h the concentrations in both the octanol and water layer remained the same. The mean log P after 24 h was 1.93 (n=3).

TABLE 17B

Log P of C10

| Sample | Conc. in Water (µg/mL) | Conc. in Octanol (µg/mL) | Log P |
|---|---|---|---|
| 1 h-1 | 1.26 | 108 | 1.93 |
| 1 h-2 | 1.21 | 103 | 1.93 |
| 1 h-3 | 1.05 | 115 | 2.04 |
| 24 h-1 | 1.27 | 104 | 1.91 |
| 24 h-2 | 1.17 | 109 | 1.97 |
| 24 h-3 | 1.28 | 99.0 | 1.89 |

A stability study for C10 was initiated at room temperature over 24 h without continuous mixing. Table 17C shows that C10 in pure water and octanol is stable over 24 h.

TABLE 17C

Water and Octanol stability for C10 at room temperature after 24 h.

| Sample | Mean (µg/mL) | SD | Percent Remaining 24 h versus 0 g |
|---|---|---|---|
| Water-0 h | 82.5 | 3.72 | 115 |
| Water-24 h | 95.0 | 21.4 | |
| Octanol-0 h | 115 | 3.06 | 93 |
| Octanol-24 h | 107 | 6.11 | |

Example 18

Determination of Penetration of C10 into the Human Nail

Two nail penetration studies were performed based on the protocol in Hui et al., *Journal of Pharmaceutical Sciences*, 91(1): 189-195 (2002) ("Hui protocol"). The purpose of this study was to determine and compare the penetration and distribution of C10 in vehicle into the human nail plate in vitro relative to 8% ciclopirox w/w in commercial lacquer (Penlac®).

Materials and Methods

Test Article and Dosage Formulation

8% ciclopirox w/w in commercial lacquer was manufactured by Dermick (Berwyn, Pa.). The radiochemical purity and specific activity of the chemical was determined as >95% and 12.5 mCi/mmol, respectively.

The study was composed of two groups. The compositions (weight %) of the dosage formulations are as follows:

Active radiolabeled compound in four groups.

| Groups* | Dosing (×14 days) | Test Chemical (%) | Radioactivity (per 10 µL) |
|---|---|---|---|
| A (C10) | qd | 10 | 0.19 µCi |
| C (Ciclopirox) | qd | 8 | 0.22 µCi |

*A = C10 group, C = Ciclopiriox group

Human Nails

Healthy human finger nail plates were collected from adult human cadavers and stored in a closed container at 0-4° C. Before the experiment, the nail plates were gently washed with normal saline to remove any contamination, then rehydrated by placing them for three hours on a cloth wetted with normal saline. The nail samples were randomly selected into four groups.

Dosing and Surface Washing Procedures

Dose Preparation:

Radioactivity of each group is approximately 0.19±0.01 and 0.22±0.03 µCi/10 µL solutions respectively, for $^{14}$C-C10 (group A), and $^{14}$C-ciclopirox (group C).

Experiment Procedure:

| Study Day | Group A | | | Group C | | |
|---|---|---|---|---|---|---|
| | wash | dose | sample | wash | dose | sample |
| 1 | | D | | | D | |
| 2 | W | D | | W | D | |
| 3 | W | D | C | W | D | C |
| 4 | W | D | | W | D | |
| 5 | W | D | | W | D | |
| 6 | W | D | C | W | D | C |
| 7 | W | D | | W | D | |
| 8 | W | D | | W | D | |
| 9 | W | D | C | W | D | C |
| 10 | W | D | | W | D | |
| 11 | W | D | | W | D | |
| 12 | W | D | C | W | D | C |
| 13 | W | D | | W | D | |
| 14 | W | D | | W | D | |
| 15 | W | | C, N | W | | C, N |

W = once per day before dosing (9~10 AM).
D = once per day (9~10 AM).
C = changing/sampling cotton ball after surface washing before topical dosing.
N = Nail sampling.

Washing Procedure

Surface washing was started in morning 10 min prior to next dosing, the surface of the nail was washed with cotton tips in a cycle, as follows:

tip wetted with absolute ethanol, then
tip wetted with absolute ethanol, then
tip wetted with 50% IVORY liquid soap, then
tip wetted with distilled water, then
final tip wetted with distilled water.

The washing samples from each cycle of each nail were pooled and collected by breaking off the cotton tip into scintillation glass vials. Aliquots of 3.0 mL methanol were added into each vial to extract test material. The radioactivity of each sample was measured in a liquid scintillation counter.

Incubation System

A Teflon one-chamber diffusion cell (PermeGear, Inc., Hellertown, Pa.) was used to hold each nail. To approximate physiological conditions, a small cotton ball wetted with 0.1 mL normal saline was placed in the chamber to serve as a nail bed and provide moisture for the nail plate. Every 3 days, 0.1 mL normal saline was injected through the inlet into the chamber to keep the cotton ball wet. The nail plate was placed on a ledge inside the receptor (1.0 cm in diameter and 0.5 cm high). The ventral (inner) surface of the nail was placed face down and rested on the wet cotton ball. The cells were placed on a platform in a large glass holding tank filled with saturated sodium phosphate solution to keep the cells at a constant humidity of 40%.

Sampling Instrument

The nail sampling instrument had two parts, a nail sample stage and a drill. The nail sampling stage consists of a copper nail holder, three adjustments, and a nail powder capture. Three adjustments allow movement in vertical direction. The first coarse adjustment (on the top) was for changing the copper cell and taking powder samples from the capture. The other two adjustments (lower) were for sampling process. The second coarse adjustment allowed movement of 25 mm and the fine adjustment provides movement of 0.20 mm. The nail powder capture was located between the copper cell and the cutter. The inner shape of the capture was inverted funnel and the end of funnel connects to a vacuum. By placing a circle filter paper inside of the funnel, the nail powder samples were captured on the filter paper during the sampling process.

Sampling Procedure

After completion of the incubation phase, the nail plate was transferred from the diffusion cell to a clean copper nail holder for sampling process. The nail plate was inverted so that the ventral (nail bed) surface now faced up and the dorsal (outer) dosed surfaced faced down. The copper nail holder has an opening as it sits on top of the stage. When the sampling process initiated, the coarse adjustment was adjusted to move the position of the stage until the nail plate was just touching the tip of the cutter. Then the drill was turned on and the fine adjustment was turned to push the stage closer to the drill, removing a nail core sample. After the above process, approximate 0.40-0.50 mm in depth and 7.9 mm in diameter nail pulverized samples were harvested from the center of the ventral (nail bed) surface of the nail.

The powdered nail samples were collected into a glass scintillation vial and weighted. Aliquots of 5.0 mL Packard soluene-350 (Packard Instrument Company, Meriden, Conn.) was added to the scintillation vial to dissolve the powder. The upper part, the intermediate and dorsal layers of the center of the nail, including the area of application of the dose was cut in the same diameter as the sampled area and was then placed into a glass scintillation vial with 5.0 mL packard soluene-350. The rest of the nail was also placed in a glass scintillation vial with 5.0 mL packard soluene-350.

The amount of nail sample removed was measured by the difference in weight of the nail plate before and after drilling, and collecting the core of powder.

Radioactivity Measurement

All radioactivity measurements were conducted with a Model 1500 Liquid Scintillation Counter (Packard Instrument Company, Downer Grove, Ill.). The counter was audited for accuracy using sealed samples of quenched and unquenched standards as detailed by the instrument manual. The $^{14}$C counting efficiency is equal to or greater than 95%. All nail samples pre-treated with packard soluene-350 were incubated at 40° C. for 48 hours followed by the addition of 10 mL scintillation cocktail (HIONIC-FLUOR, Packard Instrument Company, Meriden, Conn.). Other samples (standard dose, surface washing, and bedding material) were mixed directly with Universal ES scintillation cocktail (ICN Biomedicals, Costa Mesa, Calif.). Background control and test samples were counted for 3 minutes each for radioactivity.

Data Analysis

All sample counts (expressed as dpm) were transcribed by hand to a computerized spreadsheet (Microsoft Excel). The individual and mean (±S.D.) amount of test chemical equivalent in nail, bedding material, and wash samples are presented as dpm, µCi, percent administered dose, and mg equivalent at each time point. The concentration of $^{14}$C-labeled test chemicals were calculated from the value based on the specific activity of each [$^{14}$C]-test chemical. The information of concentration of non-labeled test chemical in the topical formulation was obtained from the manufactures. Total concentration of test chemical equivalent is the sum of the concentration of [$^{14}$C]-labeled test chemical and the concentration of non-labeled test chemical. The value of total amount of test chemical equivalent in each nail sample was calculated from those values based on radioactivity of the sample and the ratio of total mg test chemical equivalent and radioactivity of the test chemical. The data was further normalized by dividing with the weight of the sample. Statistical significant of nail samples from every two groups was analyzed by student t-test.

Terminology

Ventral/intermediate center: Powdered nail sample drilled from the center of the inner surface (facing the nail bed) approximately 0.3-0.5 mm in depth to the surface. The area is beneath the dosed site of the nail place but does not include dosed surface (dorsal nail surface).

Dorsal/intermediate center: Immediate area of dosed site.

Remainder nail: The remaining part of the nail that has not been dosed.

Supporting bed: The cotton ball placed within the Teflon chamber of the diffusion cell to provide moisture to the nail plate and also to receive chemicals penetrating through the nail plate.

Surfacing washing: Ethanol (or other organic solvents) and soap/water washing on the surface of the dosed site.

Ring: A plastic ring placed on the top of the nail plate to prevent leakage from the dose site onto rest of the nail plate or inside of the cell chamber.

Cell washing: Ethanol (or other organic solvents) and soap/water wash of the inside of the diffusion cell.

Results

Characteristics of Nail Samples

For both groups (Group A group and Group C) the thickness of whole nail plate, the depth of the ventral surface core sample removed by cutter, the percentage of the whole nail thickness, and the actual weight of powdered nail sample were collected. No statistical difference is found between two groups (P>0.05).

Weight Normalized C10 and Ciclopirox Equivalent in Nail

FIG. 3 shows summarized normalized drug equivalents in each part (layer) of nail samples. After weight normalization, the concentration of C10 equivalent in dorsal/intermediate center, ventral/intermediate center, and remainder nail samples was significantly higher than that of ciclopirox equivalent ($p \leq 0.002$).

C10 and Ciclopirox Equivalent in Cotton Ball Nail Supporting Bed

FIG. 4 shows summarized C10 and ciclopirox equivalent in supporting bed cotton ball samples. Similar to weight normalized C10 equivalent in the nail plate samples, absolute amount of C10 equivalent per cotton ball sample in group A (after 14 day dosing) was significantly higher than that of ciclopirox in group C ($p \leq 0.004$). The difference of these two test chemicals was 250 times.

Mass Balance of Radioactivity of [$^{14}$C]-C10 and [$^{14}$C]-Ciclopirox after 14-Day Treatment Table 5 shows summarized radioactive recovery from washing, nail samples, and supporting bed cotton ball samples. Cumulative radioactivity recoveries of carbon-14 were 88±9.21, and 89±1.56 percent of applied dose in group A, and group C, respectively. 88% of the radiolabeled material was accounted for.

CONCLUSION

In this study, penetration rate of [$^{14}$C]-C10 in Anacor topical formulation and [$^{14}$C]-ciclopirox (8% w/w in commercial lacquer) into human nail with four different dosing and washing methods was studied.

Results show that much more amount of [$^{14}$C]-C10 penetrating into the deeper parts of the nail when compared with [$^{14}$C]-ciclopirox. Tables 3 and 4 show that the amount of [$^{14}$C]-C10 equivalent in ventral/intermediate center of the nail layer and cotton ball supporting bed in the group A was statistically higher ($p \leq 0.002$) than group C after a 14-day dosing period.

Example 19

Determination of Penetration of C10 into the Human Nail

The aim of the current study was to assess and compare the perungual absorption of C10 in a simple vehicle using MedPharm's TurChub® model (see http://www.medpharm.co.uk; specifically http://www.medpharm.co.uk/downloads/Skin%20and%20nail%20dec%202003.pdf; viewed Feb. 14, 2006). in a full scale experiment. Six replicates involving C10 were conducted and Formulations Y (8% ciclopirox w/w in commercial lacquer) and Z (Loceryl, 5% amorolfine w/v in commercial lacquer) were used as the reference formulations.

The following materials were used in these experiments. These materials were used without any modifications.

A dose of 40 µL/cm$^2$ of the test compound C10 in 50:50 propylene glycol:ethyl acetate was applied to a full thickness nail sample each day over a total duration of five days. Both the reference formulations were also applied at the same dose.

TurChub® Zone of Inhibition Experiment

Placebo, test item C10 in vehicle and the reference formulations Y and Z were tested for their inhibition of *Trichophyton rubrum* (*T. rubrum*) growth after penetration through a full thickness human nail using a zone of inhibition measurement.

Formulation Efficacy Testing

Figure 6:
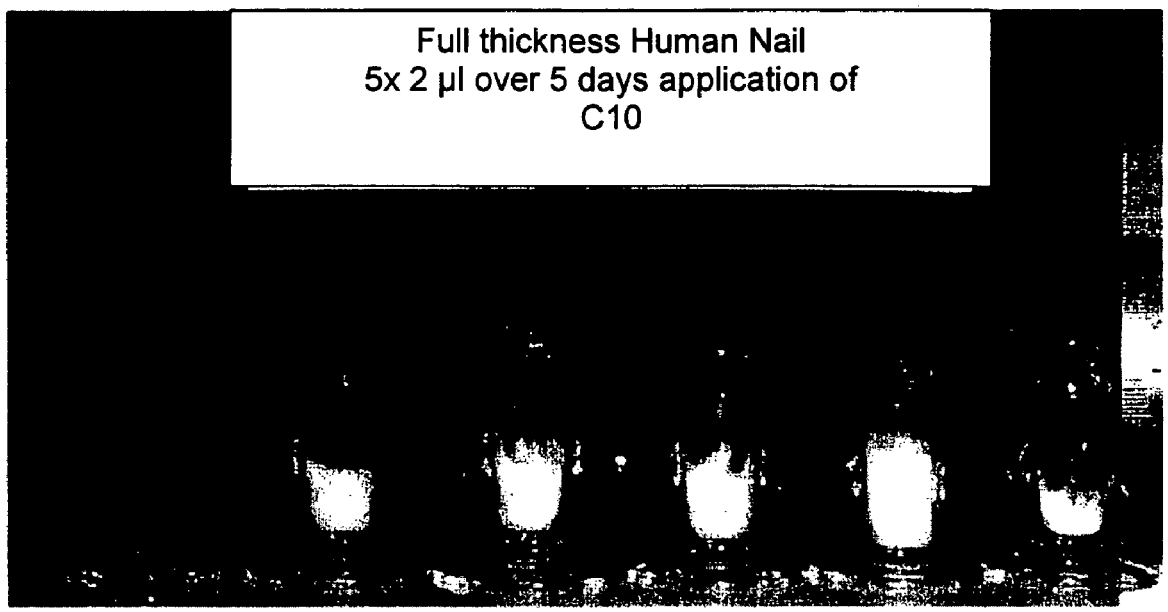
FIG. 6 displays the results of a 40 μL/cm² aliquot of C10 10% w/v solution applied per day over five days. Zones of inhibition (in the order of the cells shown in the figure) of 100%, 67%, 46%, 57%, 38% and 71% were observed for the growth of T. rubrum. Green arrow indicates the measurement of zone of inhibition.
Figure 7:
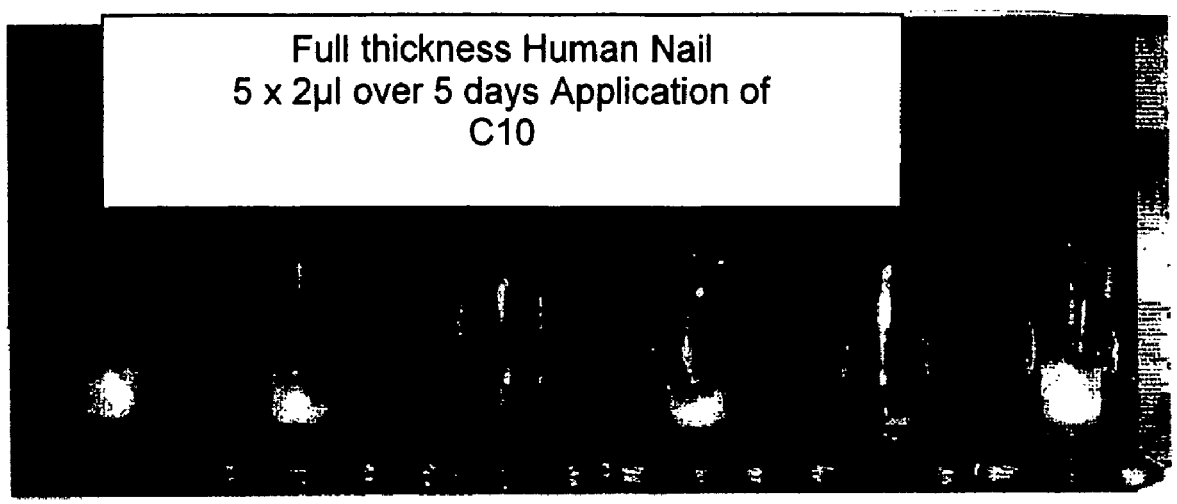
FIG. 7 displays the results of a 40 μL/cm aliquot of C10 10% w/v solution applied per day over five days. Zones of inhibition (in the order of the cells shown in the figure) of 74%, 86%, 100%, 82%, 100% and 84% were observed for the growth of T. rubrum.
Figure 8:
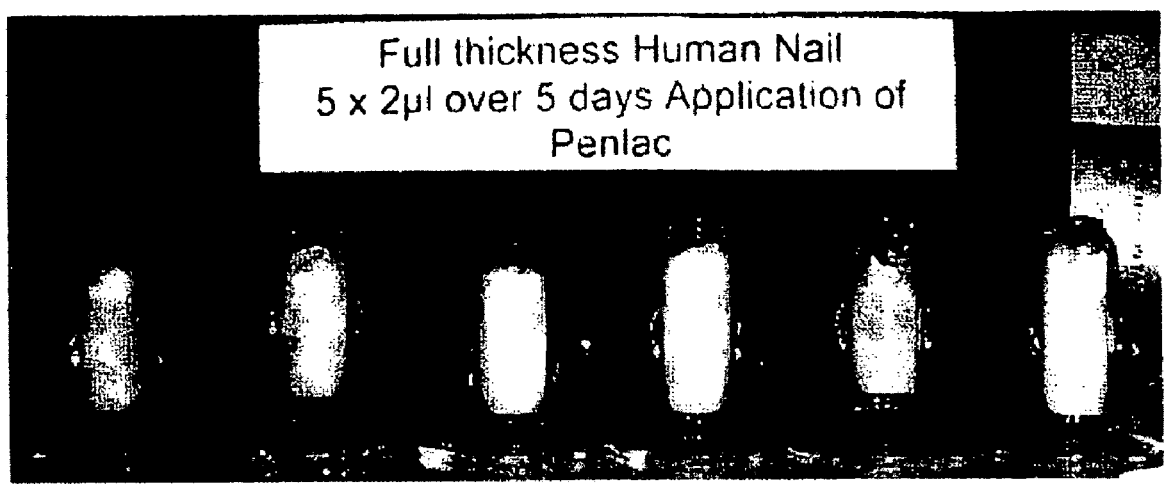
FIG. 8 displays the results of a 40 μL/cm² aliquot of 8% ciclopirox in w/w commercial lacquer applied per day over five days. No zone of inhibition observed; full carpet growth of T. rubrum.
Figure 9:
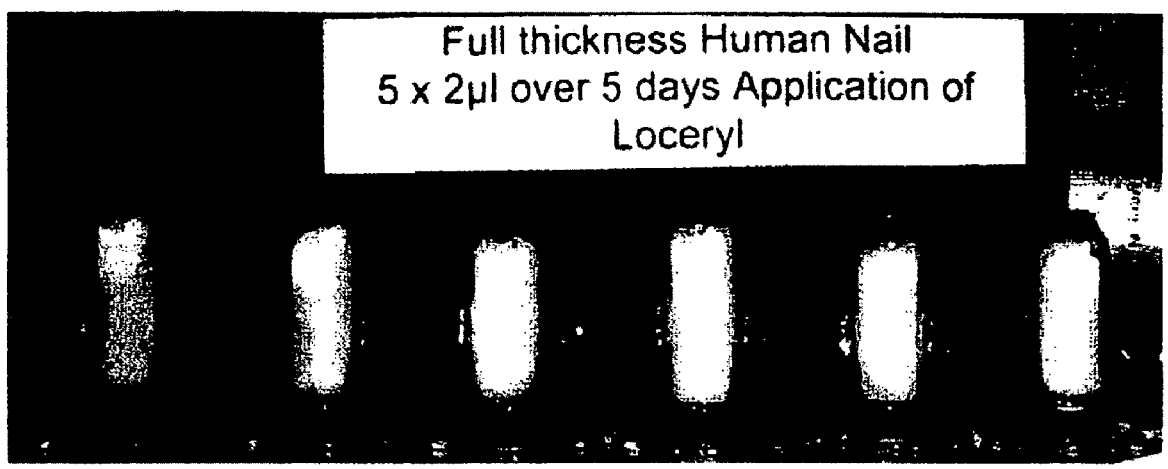
FIG. 9 displays the results of a 40 μL/cm² aliquot of 5% amorolfine w/v in commercial lacquer applied per day over five days. No zone of inhibition observed; full carpet growth of T. rubrum.

FIGS. 5-9 show the results obtained from the TurChub zone of inhibition assays. It can be observed that C10 is a potent antifungal agent, which can penetrate through a full thickness nail to elicit its effect against the target organism *T. rubrum*. No zones of inhibition were observed with reference formulations Y and Z or with the placebo for C10. The experiment using C10 was repeated for a second time to confirm the result and it can be observed from FIGS. 6 and 7 that C10 shows zones of inhibition of 100%, 67%, 46%, 57%, 38% and 71% in the first experiment and 74%, 86%, 100%, 82%, 100% and 84% in the second experiment. The measurement was taken from the nail to the first point of growth observed.

From the results obtained using MedPharm's TurChub zone of inhibition assay as a test system, the test item C10 was found to be a powerful antifungal agent and demonstrated superior results vs. the commercial reference formulations Y and Z. From these experiments it appears that the compound is permeating through a full thickness nail barrier to exhibit the antifungal activity.

Example 20

Determination of Penetration of C10 into the Human Nail

Dose Response

The optimal dose-response range for penetration into the human nail was determined to be between 1% and 15%. The experiments to determine the optimal dose-response was conducted as follows.

Tests at different test compound concentrations were conducted on nails derived from the same cadaver. Cadaver nails were hydrated overnight, cut into 4 equally sized squares and placed onto individual poloxomer supports. Test articles were formulated in a lacquer at 1%, 2.5%, 5%, 7.5%, 10% and 15% w/v. A 40 μL/cm$^2$ dose is applied to the center of the nail piece and the nails are left for 24 hrs. Nails are removed from the poloxomer support. Poloxomer support is analyzed for quantity of compound using LC/MS/MS.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of treating an infection in an animal, said method comprising administering to the animal a therapeutically effective amount of 1,3-dihydro-5-fluoro-1-hydroxy-2,1-benzoxaborole, or a pharmaceutically acceptable salt thereof, sufficient to treat said infection.

2. The method of claim 1, wherein said infection is a member selected from a systemic infection, a cutaneous infection, and an ungual or periungual infection.

3. The method of claim 1, wherein said infection is a member selected from chloronychia, paronychias, erysipeloid, onychorrhexis, gonorrhea, swimming-pool granuloma, larva migrans, leprosy, Orf nodule, milkers' nodules, herpetic whitlow, acute bacterial perionyxis, chronic perionyxis, sporotrichosis, syphilis, tuberculosis verrucosa cutis, tularemia, tungiasis, peri- and subungual warts, zona, nail dystrophy (trachyonychia), dermatological diseases, psoriasis, pustular psoriasis, alopecia aerata, parakeratosis pustulosa, contact dermatosis, Reiter's syndrome, psoriasiform acral dermatitis, lichen planus, idiopathy atrophy in the nails, lichin nitidus, lichen striatus, inflammatory linear verrucous epidermal naevus (ILVEN), alopecia, pemphigus, bullous pemphigoid, acquired epidermolysis bullosa, Darier's disease, pityriasis rubra pilaris, palmoplantar keratoderma, contact eczema, polymorphic erythema, scabies, Bazex syndrome, systemic scleroderma, systemic lupus erythematosus, chronic lupus erythematosus, dermatomyositus, Sporotrichosis, Mycotic keratitis, Extension oculomycosis, Endogenous oculomycosis, Lobomycosis, Mycetoma, Piedra, Pityriasis versicolor, Tinea corporis, Tinea cruris, Tinea pedis, Tinea barbae, Tinea capitis, Tinea nigra, Otomycosis, Tinea favosa, Chromomycosis, and Tinea Imbricata.

4. The method of claim 1, wherein said infection is onychomycosis.

5. The method of claim 1, wherein said animal is a member selected from a human, cattle, goat, pig, sheep, horse, cow, bull, dog, guinea pig, gerbil, rabbit, cat, chicken and turkey.

6. The method of claim 4, wherein said onychomycosis is tinea unguium.

7. The method of claim 1, wherein said animal is a human.

8. The method of claim 1, wherein the administering is at a site which is a member selected from the skin, nail, hair, hoof and claw.

9. The method of claim 8, wherein said skin is the skin surrounding the nail, hair, hoof or claw.

10. The method of claim 1, wherein said infection is a fungal infection.

11. A method of treating onychomycosis in a human, said method comprising administering to the human a therapeutically effective amount of 1,3-dihydro-5-fluoro-1-hydroxy-2,1-benzoxaborole, or a pharmaceutically acceptable salt thereof, sufficient to treat said onychomycosis.

12. A method of inhibiting the growth of a fungus in a human, said method comprising administering to the human a therapeutically effective amount of 1,3-dihydro-5-fluoro-1-hydroxy-2,1-benzoxaborole, or a pharmaceutically acceptable salt thereof.

* * * * *

UNITED STATES PATENT AND TRADEMARK OFFICE
CERTIFICATE OF CORRECTION

| | | |
|---|---|---|
| PATENT NO. | : 7,582,621 B2 | Page 1 of 1 |
| APPLICATION NO. | : 11/357687 | |
| DATED | : September 1, 2009 | |
| INVENTOR(S) | : Baker et al. | |

It is certified that error appears in the above-identified patent and that said Letters Patent is hereby corrected as shown below:

On the Title Page

Item [*] Notice:   Subject to any disclaimer, the term of this patent is extended or adjusted under 35 U.S.C. 154(b) by 267 days Delete the phrase "by 267 days" and insert -- by 464 days --

Signed and Sealed this

First Day of June, 2010

David J. Kappos
*Director of the United States Patent and Trademark Office*

UNITED STATES PATENT AND TRADEMARK OFFICE
Certificate

Patent No. 7,582,621 B2                                                        Patented: September 1, 2009

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Stephen J. Baker, Mountain View, CA (US); Tsutomu Akama, Sunnyvale, CA (US); Vincent S. Hernandez, Watsonville, CA (US); Karin M. Hold, Belmont, CA (US); James J. Leyden, Malvern, PA (US); Jacob J. Plattner, Berkeley, CA (US); Virginia Sanders, San Francisco, CA (US); and Yong-Kang Zhang, San Jose, CA (US).

Signed and Sealed this Sixteenth Day of July 2013.

BRANDON FETTEROLF
*Supervisory Patent Examiner*
Art Unit 1628
Technology Center 1600